United States Patent
Davis-Ward et al.

(10) Patent No.: US 7,514,446 B2
(45) Date of Patent: Apr. 7, 2009

(54) PYRIMIDINE COMPOUNDS

(75) Inventors: Ronda Davis-Ward, Durham, NC (US); Robert Anthony Mook, Jr., Durham, NC (US); Michael J Neeb, King of Prussia, PA (US); James M Salovich, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 415 days.

(21) Appl. No.: 10/545,352

(22) PCT Filed: Feb. 11, 2004

(86) PCT No.: PCT/US2004/004197

§ 371 (c)(1),
(2), (4) Date: Jan. 31, 2006

(87) PCT Pub. No.: WO2004/074244

PCT Pub. Date: Sep. 2, 2004

(65) Prior Publication Data

US 2007/0010668 A1      Jan. 11, 2007

Related U.S. Application Data

(60) Provisional application No. 60/448,795, filed on Feb. 20, 2003.

(51) Int. Cl.
*A61K 31/505* (2006.01)
*C07D 239/24* (2006.01)

(52) U.S. Cl. .................. 514/275; 544/224; 544/242; 544/297; 514/247; 514/256

(58) Field of Classification Search ............... 544/224, 544/242, 297; 514/247, 256, 275
See application file for complete search history.

(56) References Cited

U.S. PATENT DOCUMENTS

| 7,105,530 B2 | 9/2006 | Boloor et al. |
| 2005/0261295 A1 | 11/2005 | Stadtmueller et al. |

FOREIGN PATENT DOCUMENTS

| EP | 0945443 A1 | 9/1999 |
| WO | WO 97/19065 | 5/1997 |
| WO | WO-98/18782 A | 5/1998 |
| WO | WO-00/12485 A | 3/2000 |
| WO | WO 00/27825 | 5/2000 |
| WO | WO 00/39101 | 7/2000 |
| WO | WO-01/60816 A | 8/2001 |
| WO | WO-01/64653 A | 9/2001 |
| WO | WO 01/64654 | 9/2001 |
| WO | WO-01/64654 A | 9/2001 |
| WO | WO 01/64655 | 9/2001 |
| WO | WO 01/64656 | 9/2001 |
| WO | WO-02/102783 A | 12/2002 |
| WO | WO 03/030909 | 4/2003 |
| WO | WO 03/032997 | 4/2003 |
| WO | WO 03/063794 | 8/2003 |
| WO | WO 03/078404 | 9/2003 |
| WO | 2004/050068 A | 6/2004 |

OTHER PUBLICATIONS

European Patent Office Communication Pursuant to Article 96(2) EPC, dated Dec. 28, 2006 in corresponding EP Application No. 04 710 264.5-2101.
CAS Registry No. 260045-05-4.
CAS Registry No. 280578-89-4.
CAS Registry No. 280578-95-2.
CAS Registry No. 280579-03-5.
CAS Registry No. 300719-17-9.
CAS Registry No. 304883-98-5.
Abdel-Fattah, et al.; J. Chemical Res. Synopses; 1994: 11: 412-413.
CAS Registry No. 321727-18-8.
CAS Registry No. 331971-38-1.
CAS Registry No. 89450-92-0.
J. Chan; The New World Health Organization Clasificalion of Lymphomas: The Past. The Present and The Future; Hematological Oncology: Jul. 2001; 19; 129-150; John Wiley & Sons Ltd.
M. Whitfield, et al.; Common Markers of Proliferation; Nature Reviews, Cancer, Feb. 2006; 6; 99-106; Nature Publishing Group.
N. Lee Harris, et al.; World Health Organization Classification of Neoplastic Diseases of the Hematopoietic and Lymphoid Tissues: Report of the Clinical Advisory Committee Meeting—Airlie House, VA, Nov. 1997; J. Clin. Oncology; Dec. 1999; 17(12): 3638-3649; American Soc. of Clin. Onc.
Ghosh, D.; J. Indian Chemical Society; May 1981; LVIII; 512-513.
Karp, V.K., et al. "Synthesis and anti-inflammatory properties of p-carboxphenyl aminopyrimidines." Khimiko-Farmatsevticheskii Zhurnal, 17(11), 1304-7, 1983.

*Primary Examiner*—Golam M Shameem
(74) *Attorney, Agent, or Firm*—Bonnie L. Deppenbrock

(57) ABSTRACT

The present invention provides compounds of formula (I):

wherein all variables are as defined herein, pharmaceutical compositions containing the same, processes for preparing the same and their use as pharmaceutical agents.

14 Claims, No Drawings

PYRIMIDINE COMPOUNDS

This Application is filed pursuant to 35 U.S.C. §371 as a United States National Phase Application of International Application No. PCT/US2004/004197, filed 11 Feb. 2004, which claims priority to U.S. Provisional Patent Application Ser. No. 60/448,795, filed 20 Feb. 2003.

BACKGROUND OF THE INVENTION

The present invention relates to novel compounds, pharmaceutical formulations comprising these compounds, and the use of these compounds in therapy. More particularly, the present invention relates to novel compounds and methods for treating conditions mediated by Polo-like Kinase, susceptible neoplasms, and other conditions.

Polo-like kinases ("PLK") are evolutionarily conserved serine/threonine kinases that play critical roles in regulating processes in the cell cycle. PLK plays a role in the entry into and the exit from mitosis in diverse organisms from yeast to mammalian cells. PLK includes PLK1, PLK2, and PLK3.

Polo-like kinases are known to be essential for mitosis in yeast, *Drosophila*, and *Xenopus*. For example, mutants of the homologous PLK genes in these organisms result in disordered mitotic spindles, and in *Drosophila* mutations can be embryonic lethal. RNA interference experiments on *Drosophila* polo have shown that ablation of polo in S2 cells results in G2/M arrest and apoptosis. PLK1 is the human homolog of *Drosophila* polo. It is believed to be involved in the entry into mitosis through the activation of cdk1 by phosphorylating and activating the phosphatase cdc25C, which in turn removes inhibitory phosphates from cdk1. This sets up an activation loop for cdk1 that leads to mitotic entry. PLK1 also phosphorylates cyclin B1, the cyclin partner of cdk1, resulting in nuclear localization. During mitosis, PLK1 has been shown to play roles in centrosome maturation and microtubule dynamics involved in formation of the mitotic spindle. PLK1 is also involved in the exit of cells from mitosis by phosphorylating and activating subunits of the anaphase-promoting complex (cdc16 and cdc27). PLK1 also phosphorylates cohesin proteins that hold sister chromatids together, exposing separase cleavage sites, and allowing separation of sister chromatids during anaphase. PLK1 may also play a role in cytokinesis through phosphorylation of the kinesin-like motor protein MKLP1. Inhibition of PLK1 thus has the potential to interfere with several stages of mitosis. Expression and activity of PLK protein increases during the cell cycle, reaching its peak during mitosis when it is also maximally phosphorylated. PLK1 mRNA is highly expressed in cells with a high mitotic index. PLK2 (serum-inducible kinase, SNK) and PLK3 (Fibroblast Growth Factor-inducible kinase, FNK) were originally identified as immediate-early genes. PLK2 is not very well characterized, but PLK3 appears to be involved in regulation of cell cycle progression through M phase but functions differently from PLK1. Recent published work suggests that PLK3 plays an important role in the regulation of microtubule dynamics and function of the centrosome during mitosis.

Overexpression of PLK1 appears to be strongly associated with neoplastic cells (including cancers). A published study has shown high levels of PLK1 RNA expression in >80% of lung and breast tumors, with little to no expression in adjacent normal tissue. Several studies have shown correlations between PLK expression, histological grade, and prognosis in several types of cancer. Significant correlations were found between percentages of PLK-positive cells and histological grade of ovarian and endometrial cancer (P<0.001). These studies noted that PLK is strongly expressed in invading endometrial carcinoma cells and that this could reflect the degree of malignancy and proliferation in endometrial carcinoma. Using RT-PCR analysis, PLK overexpression was detected in 97% of esophageal carcinomas and 73% of gastric carcinomas as compared to the corresponding normal tissues. Further, patients with high levels of PLK overexpression in esophageal carcinoma represented a significantly poorer prognosis group than those with low levels of PLK overexpression. In head and neck cancers, elevated mRNA expression of PLK1 was observed in most tumors; a Kaplan-Meier analysis showed that those patients with moderate levels of PLK1 expression survived longer than those with high levels of PLK1 expression. Analysis of patients with non-small cell lung carcinoma showed similar outcomes related to PLK1 expression.

Disruption of mitosis with anti-microtubule drugs has been a successful approach in cancer chemotherapy. The taxanes and vinca alkaloids have been effectively used in the clinic, but they have undesirable side effects. In addition, many tumors appear to have weakened G2/M cell cycle checkpoints; in response to mitotic disruption these tumors attempt to bypass mitosis, leading to mitotic catastrophe and cell death. Several studies suggest that the disruption of mitosis by targeting PLK may be a feasible approach to selective tumor cell destruction. There remains a need in the art for new approaches to the treatment of neoplasms.

BRIEF SUMMARY OF THE INVENTION

According to a first aspect of the invention there is provided a compound of formula (I):

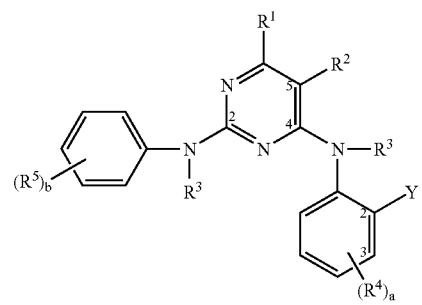

wherein:

$R^1$ is selected from the group consisting of H, halo, alkyl, alkenyl, alkynyl;

$R^2$ is selected from the group consisting of halo, alkyl, alkenyl, alkynyl, cycloalkyl, cycloalkenyl, —$(R^7)_g$—C(O)$R^6$, —$(R^7)_g$—CO$_2R^6$, —$(R^7)_g$—C(O)N$(R^6)_2$, —$(R^7)_g$—OR$^6$, —O—$(R^7)_g$-Ay, —$(R^7)_g$—S(O)$_eR^6$, —$(R^7)_g$—N$(R^6)_2$, —$(R^7)_g$—N$(R^6)$C(O)$R^6$, —$(R^7)_g$—CN, —$(R^7)_g$—SCN, —NO$_2$, —N$_3$, Ay and 5- to 9-membered heteroaryl containing 1 or 2 heteroatoms selected from N, O and S;

each $R^3$ is the same or different and is independently H or alkyl;

Y is selected from the group consisting of —C(O)$R^8$, —C(S)$R^8$, —S(O)$_eR^9$, —S(O)$_eN(R^9)_2$, —N$(R^9)_2$, N$(R^9)$—S(O)$_eR^9$, —N$(R^9)$—C(O)$R^9$, —N$(R^9)$—CO$_2R^9$, and —N$(R^9)$—C(O)N$(R^9)_2$, or Y, together with C-2 and C-3 form a fused ring system of formula A:

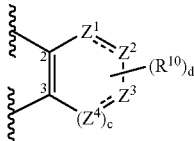

wherein $R^8$ is selected from the group consisting of alkyl, alkenyl, alkynyl, cycloalkyl, cycloalkenyl, Ay, Het, —$OR^6$, —O—$(R^7)_g$-Ay, —O—$(R^7)_g$-Het, —$N(R^6)_2$, —$N(R^6)$—$(R^7)_g$-Ay, —$N(R^6)$—$(R^7)_g$-Het, —$N(R^6)$—$(R^7)_g$—$OR^6$, —$N(R^6)$—$(R^7)_g$—$C(O)R^6$, —$N(R^6)$—$(R^7)_g$—$CO_2R^6$, —$N(R^6)$—$(R^7)_g$—$SO_2R^6$, and —$N(R^6)$—$(R^7)_g$—$N(R^6)_2$;

each $R^9$ is the same or different and is independently selected from the group consisting of H, alkyl, alkenyl, alkynyl, cycloalkyl, cycloalkenyl, Ay and Het;

c is 0 or 1;

$Z^1$, $Z^2$, $Z^3$ and $Z^4$ are each independently selected from the group consisting of C, O, S and N, wherein when c is 0, at least one of $Z^1$, $Z^2$ and $Z^3$ is C and wherein when c is 1, at least two of $Z^1$, $Z^2$, $Z^3$ and $Z^4$ are C;

each dashed line represents an optional double bond;

d is 0, 1 or 2;

each $R^{10}$ is the same or different and is independently selected from the group consisting of halo, alkyl, oxo, hydroxy, mercapto and amino;

a is 0, 1, 2 or 3;

each $R^4$ is the same or different and is independently selected from the group consisting of halo, alkyl alkenyl, alkynyl, —$(R^7)_g$-cycloalkyl, —$(R^7)_g$-cycloalkenyl, —$(R^7)_g$-Ay, —$(R^7)_g$-Het, —$(R^7)_g$—$C(O)R^6$, —$(R^7)_g$—$C(O)$Ay, —$(R^7)_g$—$C(O)$Het, —$(R^7)_g$—$CO_2R^6$, —$(R^7)_g$—$CO_2$Ay, —$(R^7)_g$—$CO_2$Het, —$(R^7)_g$—$C(O)N(R^6)_2$, —$(R^7)_g$—$OR^6$, —$(R^7)_g$—$O$Ay, —$(R^7)_g$—$O$Het, —$(R^7)_g$—$OC(O)R^6$, —$(R^7)_g$—$OC(O)$Ay, —$(R^7)_g$—$OC(O)$ Het, —$(R^7)_g$—$S(O)_eR^6$, —$(R^7)$, —$S(O)_e$Ay —$(R^7)_g$—$S(O)_e$Het, —$(R^7)_g$—$S(O)_eN(R^6)_2$, —$(R^7)_g$—$S(O)_eN(R^6)$Ay, —$(R^7)_g$—$S(O)_eN(R^6)$Het, —$(R^7)_g$—$N(R^6)_2$, —$(R^7)_g$—$N(R^6)$Ay, —$(R^7)_g$—$N(R^6)$Het, —$(R^7)_g$—$N(R^6)C(O)R^6$, —$(R^7)_g$—$N(R^6)C(O)$Ay, —$(R^7)_g$—$N(R^6)C(O)$Het, —$(R^7)_g$—$N(R^6)C(O)N(R^6)_2$, —$(R^7)_g$—$N(R^6)S(O)_eR^6$, —$(R^7)_g$—$N(R^6)S(O)_e$Ay, —$(R^7)_g$—$N(R^6)S(O)_e$Het, —$NO_2$, —CN, —SCN and —$N_3$, or two adjacent $R^4$ groups together with the carbon atoms to which they are bonded form a phenyl or a 5- or 6-membered heterocycle or heteroaryl containing 1 or 2 heteroatoms selected from the group consisting of O, N and S;

each e is the same or different and is independently 0, 1 or 2;

b is 0, 1, 2, 3, 4 or 5;

each $R^5$ is the same or different and is a group of formula $(R^7)_g$—$R^{11}$, or two adjacent $R^5$ groups are each the same or different and are independently selected from the group consisting of alkyl, alkenyl, —$OR^6$, —$S(O)_eR^6$ and —$N(R^6)_2$ and, together with the carbon atoms to which they are bonded, they form a $C_{5-6}$cycloalkyl, $C_{5-6}$cycloalkenyl or a 5- or 6-membered heterocycle or heteroaryl containing 1 or 2 heteroatoms selected from the group consisting of N, O and S;

each $R^6$ is the same or different and is independently selected from the group consisting of H, alkyl, alkenyl, alkynyl, cycloalkyl and cycloalkenyl;

g is 0 or 1;

$R^7$ is alkylene or alkenylene;

Ay is aryl;

Het is a 5- or 6-membered heterocycle or heteroaryl containing 1, 2 or 3 heteroatoms selected from the group consisting of N, O and S;

$R^{11}$ is selected from the group consisting of halo, alkyl, alkenyl, alkynyl, cycloalkyl, cycloalkenyl, Ay, Het, —$C(O)R^6$, —$C(O)$Ay, —$C(O)$Het, —$CO_2R^6$, —$CO_2$Ay, —$CO_2$Het, —$C(O)$—$R^7$—$OR^6$, —$C(O)$—$R^7$—$O$Ay, —$C(O)$—$R^7$—$O$Het, —$C(O)N(R^6)_2$, —$C(O)N(R^6)$Ay, —$C(O)N(R^6)$Het, —$C(O)N(R^6)$—$(R^7)_g$—$N(R^6)_2$, —$C(O)N(R^6)$—$(R^7)_g$—$CO_2R^6$, —$C(O)N(R^6)$—$(R^7)_g$—$S(O)_eR^6$, —$OR^6$, —$OC(O)R^6$, —O—$(R^7)_g$-Ay, —$OC(O)$Ay, —O—$(R^7)_g$-Het, —$OC(O)$Het, —O—$R^7$—$OR^6$, —O—$R^7$—$N(R^6)_2$, —$S(O)_eR^6$, —$S(O)_e$—$(R^7)_g$-Ay, —$S(O)_e$—$(R^7)_g$-Het, —$S(O)_e$—$(R^7)_g$—$N(R^6)_2$, —$S(O)_e$—$(Re)_g$—$N(R^6)$Ay, —$S(O)_e$—$(R^7)_g$—$N(R^6)$Het, —$S(O)_eN(R^6)$—$(R^7)_g$—$C(O)R^6$, —$S(O)_eN(R^6)$—$(R^7)_g$—$C(O)$Ay, —$S(O)_eN(R^6)$—$(R^7)_g$—$C(O)$Het, —$N(R^6)_2$, —$N(R^6)$—$(R^7)_g$-Ay, —$N(R^6)$—$(R^7)_g$-Het, —$N(R^6)$—$(R^7)_g$—$C(O)R^6$, —$N(R^6)$—$C(O)$—$(R^7)_g$-Ay, —$N(R^6)$—$C(O)$—$(R^7)_g$-Het, —$N(R^6)$—$C(O)$—$(R^7)_g$—$N(R^6)_2$, —$N(R^6)$—$C(O)$—$(R^7)_g$—$N(R^6)$Ay, —$N(R^6)$—$C(O)$—$(R^7)_g$—$N(R^6)$Het, —$N(R^6)$—$C(O)$—$(R^7)_g$—$N(R^6)$—$(R^7$—$O)_h$—$N(R^6)$—$CO_2R^6$, —$N(R^6)$—$(R^7)_g$—$S(O)_eR^6$, —$N(R^6)$—$(R^7)_g$—$S(O)_e$Ay, —$N(R^6)$—$(R^7)_g$—$S(O)_e$Het, —$N(R^6)$—$R^7$—$N(R^6)_2$, —$N(R^6)$—$R^7$—$OR^6$, —CN, —SCN, —$NO_2$, and —$N_3$; and h is 1-20;

wherein when $R^1$ is —$CH_3$, $R^2$ is Br or $NO_2$, both $R^3$ are H, a is 0 and b is 0 or 1 wherein $R^5$ is —$CO_2H$, then Y is not —$CO_2H$ or a pharmaceutically acceptable salt, solvate or physiologically functional derivative thereof.

In another aspect of the invention there is provided a pharmaceutical composition comprising a compound of formula (I). In one embodiment, the pharmaceutical composition further comprises a pharmaceutically acceptable carrier, diluent or excipient.

In a third aspect of the invention, there is provided a method for treating a condition mediated by PLK in an animal. The method comprises administering to the animal a therapeutically effective amount of a compound of formula (I) or a pharmaceutically acceptable salt, solvate or physiologically functional derivative thereof.

In a fourth aspect of the invention, there is provided a method for treating a susceptible neoplasm in an animal. The method comprises administering to the animal a therapeutically effective amount of a compound of formula (I) or a pharmaceutically acceptable salt, solvate or physiologically functional derivative thereof. The susceptible neoplasm may be selected from the group consisting of breast cancer, colon cancer, lung cancer, prostate cancer, lymphoma, leukemia, endometrial cancer, melanoma, pancreatic cancer, ovarian cancer, squamous carcinoma, carcinoma of the head and neck, and esophageal carcinoma.

In a fifth aspect of the invention, there is provided a method for treating a condition characterized by inappropriate cellular proliferation. The method comprises contacting the cell with a therapeutically effective amount of a compound of formula (I) or a pharmaceutically acceptable salt, solvate or physiologically functional derivative thereof.

In a sixth aspect, the present invention provides a method for inhibiting proliferation of a cell. The method comprises contacting the cell with an amount of a compound of formula (I) or a pharmaceutically acceptable salt, solvate or physiologically functional derivative thereof sufficient to inhibit proliferation of the cell.

In another aspect, the present invention provides a method for inhibiting mitosis in a cell. The method comprises administering to the cell an amount of a compound of formula (I) or a pharmaceutically acceptable salt, solvate or physiologically functional derivative thereof sufficient to inhibit mitosis in the cell.

In another aspect, there is provided a process for preparing a compound of formula (I) comprising reacting a compound of formula (IV):

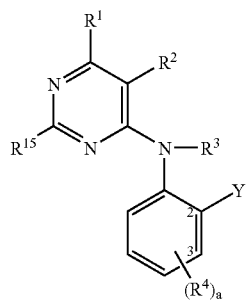

wherein $R^{15}$ is selected from the group consisting of halo and $—S(O)_eR^6$; with a compound of formula (V):

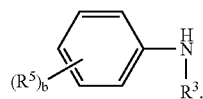

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

In another aspect, the present invention provides a compound of formula (I) or a pharmaceutically acceptable salt, solvate or physiologically functional derivative thereof for use in therapy.

In yet another aspect, the present invention provides a compound of formula (I) or a pharmaceutically acceptable salt, solvate or physiologically functional derivative thereof for use in the treatment of a condition mediated by PLK in an animal.

In yet another aspect, the present invention provides a compound of formula (I) or a pharmaceutically acceptable salt, solvate or physiologically functional derivative thereof for use in the treatment of a susceptible neoplasm in an animal.

In another aspect, the present invention provides a compound of formula (I) or a pharmaceutically acceptable salt, solvate or physiologically functional derivative thereof for use in the treatment of a condition characterized by inappropriate cellular proliferation.

In yet another aspect, the present invention provides a compound of formula (I) or a pharmaceutically acceptable salt, solvate or physiologically functional derivative thereof for use in inhibiting proliferation of a cell.

In yet another aspect, the present invention provides a compound of formula (I) or a pharmaceutically acceptable salt, solvate or physiologically functional derivative thereof for use in inhibiting mitosis in a cell.

In yet another aspect, the present invention provides the use of a compound of formula (I) or a pharmaceutically acceptable salt, solvate or physiologically functional derivative thereof for the preparation of a medicament for the treatment of condition mediated by PLK in an animal.

In yet another aspect, the present invention provides the use of a compound of formula (I) or a pharmaceutically acceptable salt, solvate or physiologically functional derivative thereof for the preparation of a medicament for the treatment of a susceptible neoplasm in an animal.

In yet another aspect, the present invention provides the use of a compound of formula (I) or a pharmaceutically acceptable salt, solvate or physiologically functional derivative thereof for the preparation of a medicament for the treatment of a condition characterized by inappropriate cellular proliferation in an animal.

In yet another aspect, the present invention provides the use of a compound of formula (I) or a pharmaceutically acceptable salt, solvate or physiologically functional derivative thereof for the preparation of a medicament for inhibiting proliferation of a cell.

In yet another aspect, the present invention provides the use of a compound of formula (I) or a pharmaceutically acceptable salt, solvate or physiologically functional derivative thereof for the preparation of a medicament for inhibiting mitosis in a cell.

In yet another aspect, the present invention provides a pharmaceutical composition comprising a compound of formula (I) for use in the treatment of a susceptible neoplasm in an animal.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example compounds of formula (IV) the phrase "a compound of formula (number)" means a compound having that formula or a pharmaceutically acceptable salt, solvate or physiologically functional derivative thereof.

As used herein, the terms "alkyl" (and "alkylene") refer to straight or branched hydrocarbon chains containing from 1 to 8 carbon atoms. Examples of "alkyl" as used herein Include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" and "alkylene" also include substituted alkyl and substituted alkylene. The alkyl or alkylene groups may be optionally substituted one or more times with halogen or cyano. Thus, the term "alkyl" includes trifluoromethyl and trifluoroethyl, among other halogenated alkyls.

As used herein, the term "alkenyl" refers to straight or branched hydrocarbon chains containing from 2 to 8 carbon atoms (unless a different number of atoms is specified) and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted one or more times with a halogen or cyano.

As used herein, the term "alkynyl" refers to straight or branched hydrocarbon chains containing from 2 to 8 carbon atoms (unless a different number of atoms is specified) and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted one or more times with a halogen or cyano.

As used herein, the term "cycloalkyl" refers to non-aromatic monocyclic carbocyclic rings having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, alkyl (including haloalkyl, e.g., perfluoroalkyl), alkenyl, alkynyl, hydroxyl, oxo, carboxyl, alkyl carboxyl, alkylether, mercapto, sulfonyl, sulfinyl, alkylsulfonyl, sulfonamido, amino, alkylamino, dialkylamino, acetylamino, amino sulfonamide and cyano. Particular cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms (unless a different number of atoms is specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from the group consisting of halo, alkyl (including haloalkyl, e.g., perfluoroalkyl), alkenyl, alkynyl, hydroxyl, oxo, carboxyl, alkylcarboxyl, alkylether, mercapto, sulfonyl, sulfinyl, alkylsulfonyl, sulfonamido, amino, alkylamino, dialkylamino, acetylamino, amino sulfonamide and cyano.

The terms "halo" and "halogen" refer to fluorine, chlorine, bromine and iodine.

The term "aryl" refers to monocyclic carbocyclic groups and fused bicyclic carbocyclic groups having from 6 to 13 carbon atoms (unless a different number of atoms is specified) and having at least one aromatic ring. Examples of particular aryl groups include but are not limited to phenyl and naphthyl. "Aryl" also includes substituted aryl. The aryl may optionally be substituted on any available carbon with one or more substituents selected from the group consisting of halo, alkyl, alkenyl, alkynyl, hydroxyl, carboxyl, alkylcarboxyl, alkylether, mercapto, sulfonyl, sulfinyl, alkylsulfonyl, sulfonamido, amino, alkylamino, dialkylamino, acetylamino, amino sulfonamide and cyano. Particular aryl groups according to the invention include phenyl and substituted phenyl.

The terms "heterocycle" and "heterocyclic" refer to monocyclic saturated or unsaturated non-aromatic groups and fused bicyclic saturated or unsaturated non-aromatic groups, having the specified number of members and containing 1, 2, 3 or 4 heteroatoms selected from N, O and S (unless a different number of heteroatoms is specified). Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. The heterocycle may optionally be substituted on any available carbon or heteroatom with one or more substituents selected from the group consisting of halo, alkyl, alkenyl, alkynyl, oxo, hydroxyl, carboxyl, alkylcarboxyl, alkylether, mercapto, sulfonyl, sulfinyl, alkylsulfonyl, sulfonamido, amino, alkylamino, dialkylamino, acetylamino, amino sulfonamide and cyano.

The term "heteroaryl" refers to aromatic monocyclic groups and fused bicyclic groups wherein at least one ring is aromatic, having the specified number of members and containing 1, 2, 3, or 4 heteroatoms selected from N, O and S (unless a different number of heteroatoms is specified). Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. The heteroaryl may optionally be substituted on any available carbon or heteroatom with one or more substituents selected from the group consisting of halo, alkyl, alkenyl, alkynyl, oxo, hydroxyl, carboxyl, alkylcarboxyl, alkylether, mercapto, sulfonyl, sulfinyl, alkylsulfonyl, sulfonamido, amino, alkylamino, dialkylamino, acetylamino, amino sulfonamide and cyano.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

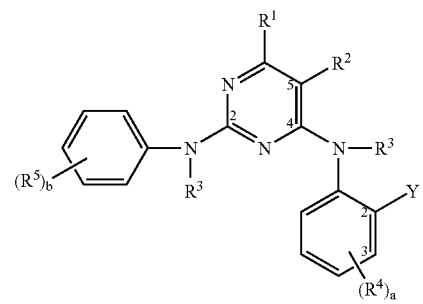

I wherein:

$R^1$ is selected from the group consisting of H, halo, alkyl, alkenyl, alkynyl;

$R^2$ is selected from the group consisting of halo, alkyl, alkenyl, alkynyl, cycloalkyl, cycloalkenyl, —$(R^7)_g$—C(O)$R^6$, —$(R^7)_g$—CO$_2R^6$, —$(R^7)_g$—C(O)N$(R^6)_2$, —$(R^7)_g$—OR$^6$, —O—$(R^7)_g$-Ay, —$(R^7)_g$—S(O)$_eR^6$, —$(R^7)_g$—N$(R^6)_2$, —$(R^7)_g$—N$(R^6)$C(O)$R^6$, —$(R^7)_g$—CN, —$(R^7)_g$—SCN, —NO$_2$, —N$_3$, Ay and 5- to 9-membered heteroaryl containing 1 or 2 heteroatoms selected from N, O and S;

each $R^3$ is the same or different and is independently H or alkyl;

Y is selected from the group consisting of —C(O)R$^8$, —C(S)R$^8$, —S(O)$_e$R$^9$, —S(O)$_e$N(R$^9$)$_2$, —N(R$^9$)$_2$, —N(R$^9$)—S(O)$_e$R$^9$, —N(R$^9$)—C(O)R$^9$, —N(R$^9$)—CO$_2$R$^9$, and —N(R$^9$)—C(O)N(R$^9$)$_2$, or Y, together with C-2 and C-3 form a fused ring system of formula A:

$$\text{A}$$

wherein
R$^8$ is selected from the group consisting of alkyl, alkenyl, alkynyl, cycloalkyl, cycloalkenyl, Ay, Het, —OR$^6$—O—(R$^7$)$_g$-Ay, —O—(R$^7$)$_g$-Het, —N(R$^6$)$_2$, —N(R$^6$)—(R$^7$)$_g$-Ay, —N(R$^6$)—(R$^7$)$_g$-Het, —N(R$^6$)—(R$^7$)$_g$—OR$^6$—N(R$^6$)—(R$^7$)$_g$—C(O)R$^6$—N(R$^6$)—(R$^6$)$_g$—CO$_2$R$^6$, —N(R$^6$)—(R$^7$)$_g$—SO$_2$R$^6$, and —N(R$^6$)—(R$^7$)$_g$—N(R$^6$)$_2$;

each R$^9$ is the same or different and is independently selected from the group consisting of H, alkyl, alkenyl, alkynyl, cycloalkyl, cycloalkenyl, Ay and Het;

c is 0 or 1;

Z$^1$, Z$^2$, Z$^3$ and Z$^4$ are each independently selected from the group consisting of C, O, S and N, wherein when c is 0, at least one of Z$^1$, Z$^2$ and Z$^3$ is C and wherein when c is 1, at least two of Z$^1$, Z$^2$ Z$^3$ and Z$^4$ are C;

each dashed line represents an optional double bond;

d is 0, 1 or 2;

each R$^{10}$ is the same or different and is independently selected from the group consisting of halo, alkyl, oxo, hydroxy, mercapto and amino;

a is 0, 1, 2 or 3;

each R$^4$ is the same or different and is independently selected from the group consisting of halo, alkyl, alkenyl, alkynyl, —(R$^7$)$_g$-cycloalkyl, —(R$^7$)$_g$-cycloalkenyl, —(R$^7$)$_g$-Ay, —(R$^7$)$_g$-Het, —(R$^7$)$_g$—C(O)R$^6$, —(R$^7$)$_g$—C(O)Ay, —(R$^7$)$_g$—C(O)Het, —(R$^7$)$_g$—CO$_2$R$^6$, —(R$^7$)$_g$—CO$_2$Ay, —(R$^7$)$_g$—CO$_2$Het, —(R$^7$)$_g$—C(O)N(R$^6$)$_2$, —(R$^7$)$_g$—OR$^6$, —(R$^7$)$_g$—OAy, —(R$^7$)$_g$—OHet, —(R$^7$)$_g$—OC(O)R$^6$, —(R$^7$)$_g$—OC(O)Ay, —(R$^7$)$_g$—OC(O)Het, —(R$^7$)$_g$—S(O)$_e$R$^6$, —(R$^7$)$_g$—S(O)$_e$Ay, —(R$^7$)$_g$—S(O)$_e$Het, —(R$^7$)$_g$—S(O)$_e$N(R$^6$)$_2$, —(R$^7$)$_g$—S(O)$_e$N(R$^6$)Ay, —(R$^7$)$_g$—S(O)$_e$N(R$^6$)Het, —(R$^7$)$_g$—N(R$^6$)$_2$, —(R$^7$)$_g$—N(R$^6$)Ay, —(R$^7$)$_g$—N(R$^6$)Het, —(R$^7$)$_g$—N(R$^6$)C(O)R$^6$, —(R$^7$)$_g$—N(R$^6$)C(O)Ay, —(R$^7$)$_g$—N(R$^6$)C(O)Het, —(R$^7$)$_g$—N(R$^6$)C(O)N(R$^6$)$_2$, —(R$^7$)$_g$—N(R$^6$)S(O)$_e$R$^6$, —(R$^7$)$_g$—N(R$^6$)S(O)$_e$Ay, —(R$^7$)$_g$—N(R$^6$)S(O)$_e$Het, —NO$_2$, —CN, —SCN and —N$_3$, or two adjacent R$^4$ groups together with the carbon atoms to which they are bonded form a phenyl or a 5- or 6-membered heterocycle or heteroaryl containing 1 or 2 heteroatoms selected from the group consisting of O, N and S;

each e is the same or different and is independently 0, 1 or 2;

b is 0, 1, 2, 3, 4 or 5;

each R$^5$ is the same or different and is a group of formula (R$^7$)$_g$—R$^{11}$, or two adjacent R$^5$ groups are each the same or different and are independently selected from the group consisting of alkyl, alkenyl, —OR$^6$, —S(O)$_e$R$^6$ and —N(R$^6$)$_2$ and, together with the carbon atoms to which they are bonded, they form a C$_{5-6}$cycloalkyl, C$_{5-6}$cycloalkenyl or a 5- or 6-membered heterocycle or heteroaryl containing 1 or 2 heteroatoms selected from the group consisting of N, O and S;

each R$^6$ is the same or different and is independently selected from the group consisting of H, alkyl, alkenyl, alkynyl, cycloalkyl and cycloalkenyl;

g is 0 or 1;

R$^7$ is alkylene or alkenylene;

Ay is aryl;

Het is a 5- or 6-membered heterocycle or heteroaryl containing 1, 2 or 3 heteroatoms selected from the group consisting of N, O and S;

R$^{11}$ is selected from the group consisting of halo, alkyl, alkenyl, alkynyl, cycloalkyl, cycloalkenyl, Ay, Het, —C(O)R$^6$, —C(O)Ay, —C(O)Het, —CO$_2$R$^6$, —CO$_2$Ay, —CO$_2$Het, —C(O)—R$^7$—OR$^6$, —C(O)—R$^7$—OAy, —C(O)—R$^7$—OHet, —C(O)N(R$^6$)$_2$, —C(O)N(R$^6$)Ay, —C(O)N(R$^6$)Het, —C(O)N(R$^6$)—(R$^7$)$_g$—N(R$^6$)$_2$, —C(O)N(R$^6$)—(R$^7$)$_g$—CO$_2$R$^6$, —C(O)N(R$^6$)—(R$^7$)$_g$—S(O)$_e$R$^6$, —OR$^6$—OC(O)R$^6$, —O—(R$^7$)$_g$-Ay, —OC(O)Ay, —O—(R$^7$)$_g$-Het, —OC(O)Het, —O—R$^7$—OR$^6$, —O—R$^7$—N(R$^6$)$_2$, —S(O)$_e$R$^6$, —S(O)$_e$—(R$^7$)$_g$-Ay, —S(O)$_e$—(R$^7$)$_g$-Het, —S(O)$_e$—(R$^7$)$_g$—N(R$^6$)$_2$, S(O)$_e$—(R$^7$)$_g$—N(R$^6$)Ay, —S(O)$_e$—(R$^7$)$_g$—N(R$^6$)Het, —S(O)$_e$N(R$^6$)—(R$^7$)$_g$—C(O)R$^6$—S(O)$_e$N(R$^6$)—(R$^7$)$_g$—C(O)Ay, —S(O)$_e$N(R$^6$)—(R$^7$)$_g$—C(O)Het, —N(R$^6$)$_2$, —N(R$^6$)—(R$^7$)$_g$-Ay, —N(R$^6$)—(R$^7$)$_g$-Het, —N(R$^6$)—(R$^7$)$_g$—C(O)R$^6$, —N(R$^6$)—C(O)—(R$^7$)$_g$-Ay, —N(R$^6$)—C(O)—(R$^7$)$_g$-Het, —N(R$^6$)—C(O)—(R$^7$)$_g$—N(R$^6$)$_2$, —N(R$^6$)—C(O)—(R$^7$)$_g$—N(R$^6$)Ay, —N(R$^6$)—C(O)—(R$^7$)$_g$—N(R$^6$)Het, —N(R$^6$)—C(O)—(R$^7$)$_g$—N(R$^6$)—(R$^7$—O)$_h$—N(R$^6$)—CO$_2$R$^6$, —N(R$^6$)—(R$^7$)$_g$—S(O)$_e$R$^6$, —N(R$^6$)—(R$^7$)$_g$—S(O)$_e$Ay, —N(R$^6$)—(R$^7$)$_g$—S(O)$_e$Het, —N(R$^6$)—R$^7$—N(R$^6$)$_2$, —N(R$^6$)—R$^7$—OR$^6$, —CN, —SCN, —NO$_2$, and —N$_3$; and h is 1-20;

wherein when R$^1$ is CH$_3$, R$^2$ is Br or NO$_2$, both R$^3$ are H, a is 0 and b is 0 or 1 wherein R$^5$ is —CO$_2$H, then Y is not —CO$_2$H or a pharmaceutically acceptable salt, solvate or physiologically functional derivative thereof.

In one embodiment, the compounds of formula (I) are defined wherein R$^1$ is selected from the group consisting of H, halo and alkyl, or any subset thereof. In one particular embodiment, R$^1$ is selected from the group consisting of H and alkyl, or any subset thereof. In one embodiment, R$^1$ is H. Specific examples of groups defining R$^1$ include but are not limited to H, fluoro, chloro, bromo, methyl, ethyl, propyl and isopropyl. In one particular embodiment, R$^1$ is selected from the group consisting of H, fluoro, chloro and methyl.

In one embodiment, the compounds of formula (I) are defined wherein R$^2$ is selected from the group consisting of halo, alkyl, alkenyl, —(R$^7$)$_g$—C(O)R$^6$, —(R$^7$)$_g$—C(O)N(R$^6$)$_2$, —(R$^7$)$_g$—CN and —NO$_2$, or any subset thereof. In one embodiment, R$^2$ is selected from the group consisting of halo, alkyl, alkenyl, —(R$^7$)$_g$—C(O)N(R$^6$)$_2$, —(R$^7$), —CN and —NO$_2$, or any subset thereof. In one particular embodiment, R$^2$ is —NO$_2$. Specific examples of groups defining R$^2$ include but are not limited to fluoro, chloro, bromo, methyl, ethyl, —C(O)H, —C(O)CH$_3$, —CH=CH$_2$, —CH=CHC(O)NH$_2$, —NO$_2$ and —CN.

In one embodiment, the compounds of formula (I) are defined wherein each R$^3$ is the same or different and is independently H or methyl. In one embodiment, one R$^3$ is methyl and one R$^3$ is H. In one embodiment, each R$^3$ is H.

In one embodiment, the compounds of formula (I) are defined wherein Y is selected from the group consisting of —C(O)R$^8$, —C(S)R$^8$, —S(O)$_e$R$^9$, —S(O)$_e$N(R$^9$)$_2$, —N(R$^9$)$_2$ and —N(R$^9$)—S(O)$_e$R$^9$, or any subset thereof. In one embodiment, Y is selected from the group consisting of —C(O)R$^8$, —S(O)$_e$R$^9$, —S(O)$_e$N(R$^9$)$_2$, —N(R$^9$)$_2$ and —N(R$^9$)—S(O)$_e$R$^9$, or any subset thereof. In one particular embodiment, Y is —C(O)R$^8$.

In one embodiment of the present invention wherein Y is —C(O)R$^8$ or —C(S)R$^8$, R$^8$ is selected from the group consisting of R$^8$ is selected from the group consisting of alkyl, cycloalkyl, cycloalkenyl, Ay, —OR$^6$, —O—(R$^7$)$_g$-Ay, —N(R$^6$)$_2$ and —N(R$^6$)—(R$^7$)$_g$-Ay, or any subset thereof. In one embodiment, R$^8$ is selected from the group consisting of alkyl, cycloalkyl, Ay, —OR$^6$ and —N(R$^6$)$_2$, or any subset thereof. In one particular embodiment, R$^8$ is selected from the group consisting of alkyl, Ay, —OR$^6$ and —N(R$^6$)$_2$, or any subset thereof. In one embodiment, Y is —C(O)R$^8$ and R$^8$ is —OR$^6$ or —N(R$^6$)$_2$.

Specific examples of some groups defining R$^8$ include but are not limited to methyl, ethyl, propyl, isopropyl, butyl, isobutyl, t-butyl, ethenyl, propenyl, cyclopentyl, cyclohexyl, phenyl, —OH, —O-methyl, —O-ethyl, —O-propyl, —O-isopropyl, —O-butyl, —O-isobutyl, —O-t-butyl, —O-cyclopentyl, —O-cyclohexyl, —O-phenyl, —O—CH$_2$-phenyl, —NH$_2$, —N(H)alkyl, —N(alkyl)$_2$, —N(H)cycloalkyl, —N(alkyl)cycloalkyl, —N(H)phenyl, —N(alkyl)phenyl, —N(H)CH$_2$-phenyl, —N(H)CH$_2$—CO$_2$H and —N(H)(CH$_2$)$_2$—OCH$_3$ and optionally substitued variants thereof consistent with the definitions of terms provided above.

In one embodiment of the present invention wherein Y is selected from the group consisting of —S(O)$_e$R$^9$, —S(O)$_e$N(R$^9$)$_2$, —N(R$^9$)$_2$ and —N(R$^9$)—S(O)$_e$R$^9$, each R$^9$ is the same or different and is independently selected from H, alkyl, alkenyl, cycloalkyl, Ay and Het, or any subset thereof. In one embodiment, each R$^9$ is the same or different and is Independently selected from the group consisting of H, alkyl and cycloalkyl, or any subset thereof. In one particular embodiment, each R$^9$ is the same or different and is independently selected from the group consisting of H and alkyl, or any subset thereof. Specific examples of some groups defining R$^9$ include but are not limited to H, methyl, ethyl, propyl, isopropyl, butyl, isobutyl, t-butyl, ethenyl, propenyl, cyclopentyl, cyclohexyl and phenyl, and optionally substitued variants thereof consistent with the definitions of terms provided above.

In another embodiment, Y together with C-2 and C-3 form a fused ring system of formula A:

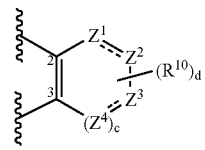

A wherein
c is 0 or 1;
Z$^1$, Z$^2$/Z$^3$ and Z$^4$ are each independently selected from the group consisting of C, O, S and N, wherein when c is 0, at least one of Z$^1$, Z$^2$ and Z$^3$ is C (carbon) and wherein when c is 1, at least two of Z$^1$, Z$^2$, Z$^3$ and Z$^4$ are C (carbon);
each dashed line represents an optional double bond;
d is 0, 1 or 2;

each R$^{10}$ is the same or different and is independently selected from the group consisting of halo, alkyl, oxo, hydroxy, mercapto and amino.

In the embodiment wherein Y together with C-2 and C-3 form a fused ring system of formula A and c is 0, the fused ring system of formula A is a five-membered ring fused at C-2 and C-3. When the fused ring system of formula A is a five-membered ring, typically, at least one of Z$^1$, Z$^2$ and Z$^3$ is carbon; and in one particular embodiment, at least two of Z$^1$, Z$^2$ and Z$^3$ are carbon.

In the embodiment wherein Y together with C-2 and C-3 form a fused ring system of formula A and c is 1, the fused ring system of formula A is a six-membered ring fused at C-2 and C-3. When the fused ring system of formula A is a six-membered ring, typically, at least two of Z$^1$, Z$^2$, Z$^3$ and Z$^4$ is carbon.

In one particular embodiment wherein Y together with C-2 and C-3 form a fused ring system of formula A, at least one of Z$^1$, Z$^2$, Z$^3$ and Z$^4$ is selected from the group consisting of N, O and S. In another particular embodiment, at least two of Z$^1$, Z$^2$, Z$^3$ and Z$^4$ is selected from the group consisting of N, O and S.

Specific examples of particular fused ring systems of formula A, defining Y include but are not limited to:

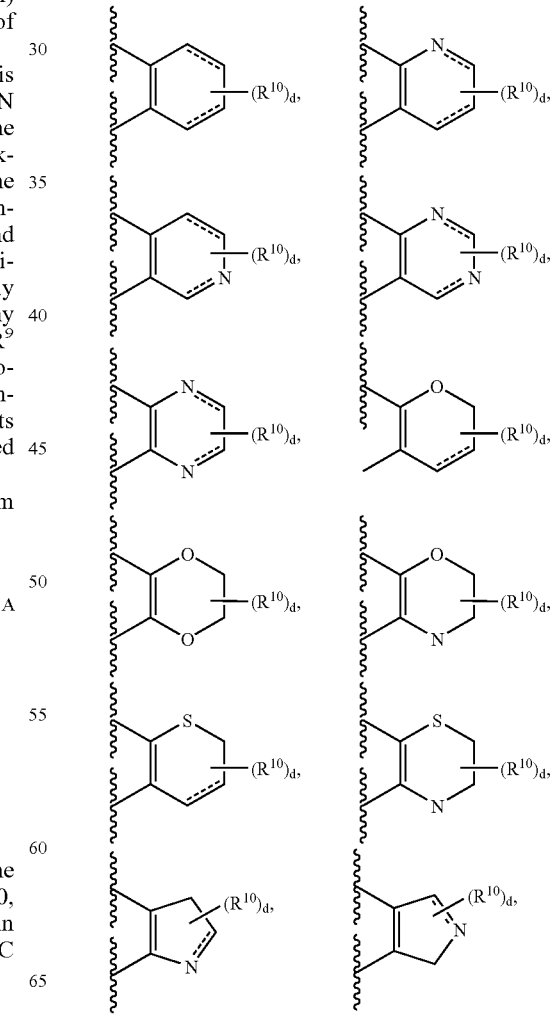

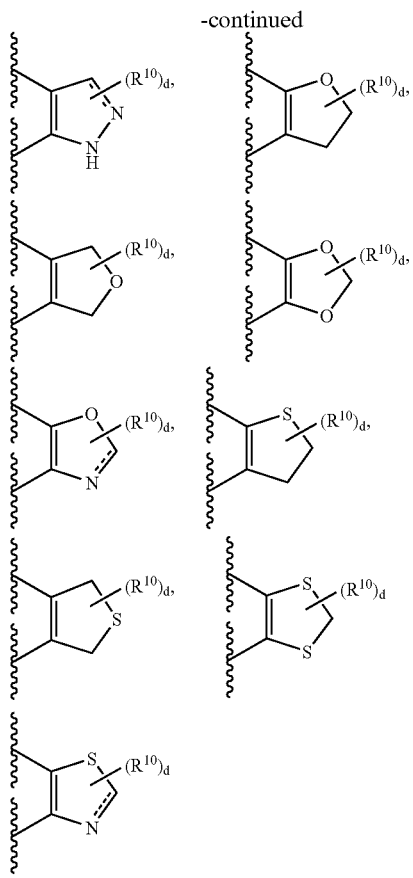

or any subset thereof, wherein d and $R^{10}$ are as defined above and each dashed line represents an optional double bond. The foregoing is intended to encompass both orientations of the moeity, i.e.,

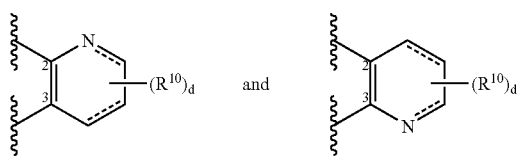

Based on the foregoing examples one skilled in the art can readily ascertain other possible fused ring systems of formula A which are contemplated by the present invention.

In one embodiment of the present invention, when Y together with C-2 and C-3 form a fused ring system of formula A, d is 0 or 1. In one particular embodiment, d is 0. In one particular embodiment, d is 1.

In the embodiment of the present invention wherein Y together with C-2 and C-3 form a fused ring system of formula A and d is 1 or 2, each $R^{10}$ is the same or different and is independently selected from halo, alkyl, oxo, hydroxyl, mercapto and amino. In such embodiments, each $R^{10}$ may be bound to any available atom $Z^1$, $Z^2$, $Z^3$, or $Z^4$ (when c is 1), including any available heteroatom, consistent with the particular choice of substituent $R^{10}$. According to one embodiment wherein d is 1 or 2, each $R^{10}$ is the same or different and is independently selected from halo, alkyl, oxo and hydroxyl. In one embodiment, each $R^{10}$ is the same or different and is halo or alkyl. Specific examples of groups defining $R^{10}$ include but are not limited to hydroxyl, oxo, chloro, bromo, methyl, ethyl, propyl and isopropyl.

In one embodiment of the present invention, the compounds of formula (I) are defined wherein Y is selected from the group consisting of —C(O)alkyl, —C(O)NH$_2$, —C(O)N(H)alkyl, —C(O)N(H)cycloalkyl, —C(O)N(alkyl)$_2$, —C(O)phenyl, —C(O)N(H)phenyl, —CO$_2$H, —CO$_2$alkyl, —CO$_2$cycloalkyl, —CO$_2$phenyl, —S-alkyl, —NH$_2$, —N(H)alkyl, —N(alkyl)$_2$, —N(H)cycloalkyl, —N(H)phenyl, consistent with the definitions of terms provided above; or Y together with C-2 and C-3 form a fused ring system selected from the group consisting of:

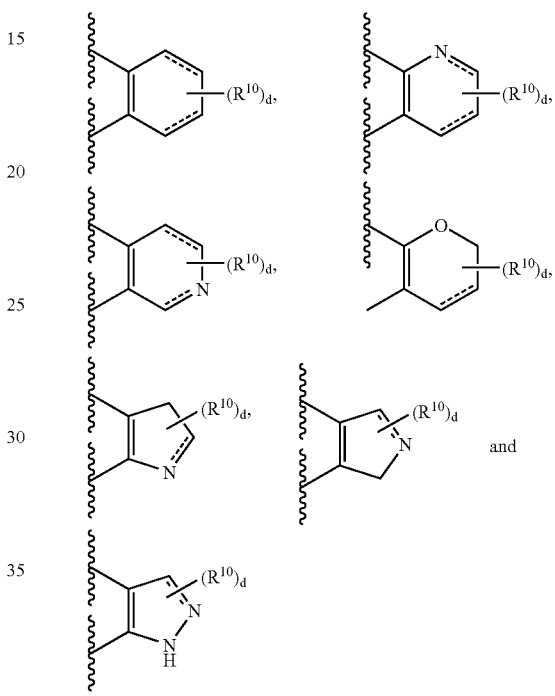

or any subset thereof, wherein d and $R^{10}$ are as defined above and each dashed line represents an optional double bond.

In one embodiment, wherein Y is a fused ring system of formula A, it is not

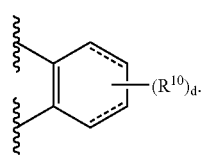

In one embodiment wherein Y is a fused ring system of formula A, it is not

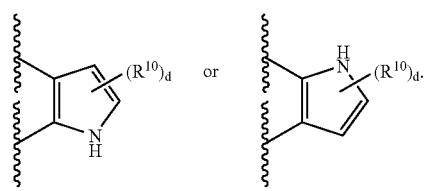

In one embodiment, the compounds of formula (I) are defined wherein a is 0 or 1. In one particular embodiment, a is 1. In another particular embodiment, a is 0. In those embodiments wherein Y together with C-2 and C-3 form a fused ring system of formula A, typically a is 0.

In those embodiments of the present invention wherein a is 1 or more, each $R^4$ is the same or different and is independently selected from the group consisting of halo, alkyl, alkenyl, alkynyl, —$(R^7)_g$-cycloalkyl, —$(R^7)_g$-cycloalkenyl, —$(R^7)_g$-Ay, —$(R^7)_g$-Het, —$(R^7)_g$—C(O)$R^6$, —$(R^7)_g$—C(O)Ay, —$(R^7)_g$—C(O)Het, —$(R^7)_g$—CO$_2R^6$, —$(R^7)_g$—CO$_2$Ay, —$(R^7)_g$—CO$_2$Het, —$(R^7)_g$—C(O)N$(R^6)_2$, —$(R^7)_g$—OR$^6$, —$(R^7)_g$—OAy, —$(R^7)_g$—OHet, —$(R^7)_g$—OC(O)R$^6$, —$(R^7)_g$—OC(O)Ay, —$(R^7)_g$—OC(O)Het, —$(R^7)_g$—S(O)$_eR^6$, —$(R^7)_g$—S(O)$_e$Ay, —$(R^7)_g$—S(O)$_e$Het, —$(R^7)_g$—S(O)$_e$N$(R^6)_2$, —$(R^7)_g$—S(O)$_e$N$(R^6)$Ay, —$(R^7)_g$—S(O)$_e$N$(R^6)$Het, —$(R^7)_g$—N$(R^6)_2$, —$(R^7)_g$—N$(R^6)$Ay, —$(R^7)_g$—N$(R^6)$Het, —$(R^7)_g$—N$(R^6)$C(O)$R^6$, —$(R^7)_g$—N$(R^6)$C(O)Ay, —$(R^7)_g$—N$(R^6)$C(O)Het, —$(R^7)_g$—N$(R^6)$C(O)N$(R^6)_2$, —$(R^7)_g$—N$(R^6)$S(O)$_eR^6$, —$(R^7)_g$—N$(R^6)$S(O)$_e$Ay —$(R^7)_g$—N$(R^6)$S(O)$_e$Het, —NO$_2$, —CN, —SCN and —N$_3$, or two adjacent $R^4$ groups together with the carbon atoms to which they are bonded form a phenyl or a 5- or 6-membered heterocycle or heteroaryl containing 1 or 2 heteroatoms selected from the group consisting of O, N and S.

In one embodiment, $R^4$ is defined wherein $R^7$ is $C_{1-3}$alkyl. In one embodiment, $R^4$ is defined wherein g is 0.

By "two adjacent $R^4$ groups" is meant two $R^4$ groups bonded to adjacent carbon atoms of the phenyl ring. One example of two adjacent $R^4$ groups is one $R^4$ group bonded to C-3 and one $R^4$ group bonded to C-4. In one embodiment, two adjacent $R^4$ groups together with the carbon atoms to which they are bonded form a phenyl or a 5 or 6-membered heterocycle containing 1 or 2 heteroatoms. In those embodiments, wherein two adjacent $R^4$ groups together with the carbon atoms to which they are bonded form a phenyl or a or a 5- or 6-membered heterocycle or heteroaryl containing 1 or 2 heteroatoms selected from the group consisting of O, N and S, each $R^4$ is the same or different and is typically selected from the group consisting of alkyl, alkenyl, —$(R^7)_g$—OR$^6$, —$(R^7)_g$—S(O)$_eR^6$, and —$(R^7)_g$—N$(R^6)_2$, where in one embodiment, g is 0. For example, in one embodiment two adjacent $R^4$ groups are —OR$^6$ and together with the carbon atoms to which they are bonded, they form a heterocyclic group such as:

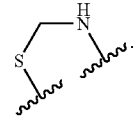

In another embodiment, two adjacent $R^4$ groups are alkenyl and together with the carbon atoms to which they are bonded, they form a phenyl.

In another embodiment two adjacent $R^4$ groups are defined as —OR$^6$ and —$(R^7)_g$—N$(R^6)_2$ respectively, and together with the carbon atoms to which they are bonded, they form a heterocyclic group such as:

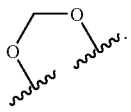

In another embodiment two adjacent $R^4$ groups are defined as —$(R^7)_g$—S(O)$_eR^6$ and —$(R^7)_g$—N$(R^6)_2$ respectively, and together with the carbon atoms to which they are bonded, they form a heterocyclic group such as:

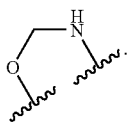

From these examples, additional embodiments can be readily ascertained by those skilled in the art.

In the embodiment wherein two adjacent $R^4$ groups bonded at C-3 and C-4 of the phenyl ring together with the carbon atoms form a phenyl or 5- or 6-membered heterocycle or heteroaryl ring, then Y, together with C-2 and C-3 do not form a fused ring system of formula A.

In one particular embodiment, two adjacent $R^4$ groups together with the carbon atoms to which they are bonded do not form a phenyl or a 5- or 6-membered heterocycle or heteroaryl containing 1 or 2 heteroatoms selected from the group consisting of O, N and S.

In one embodiment, each $R^4$ is the same or different and is independently selected from the group consisting of halo, alkyl, alkenyl, alkynyl, —$(R^7)_g$-cycloalkyl, —$(R^7)_g$-cycloalkenyl, —$(R^7)_g$-Ay, —$(R^7)_g$-Het, —$(R^7)_g$—C(O)$R^6$, —$(R^7)_g$—C(O)Ay, —$(R^7)_g$—C(O)Het, —$(R^7)_g$—CO$_2R^6$, —$(R^7)_g$—CO$_2$Ay, —$(R^7)_g$—CO$_2$Het, —$(R^7)_g$—C(O)N$(R^6)_2$, —$(R^7)_g$—OR$^6$, —$(R^7)_g$—OAy, —$(R^7)_g$—OHet, —$(R^7)_g$—OC(O)$R^6$, —$(R^7)_g$—OC(O)Ay, —$(R^7)_g$—OC(O)Het, —$(R^7)_g$—S(O)$_eR^6$, —$(R^7)_g$—S(O)$_e$Ay, —$(R^7)_g$—S(O)$_e$N$(R^6)_2$, —$(R^7)_g$—S(O)$_e$N$(R^6)$Ay, —$(R^7)_g$—S(O)$_e$N$(R^6)$Het, —$(R^7)_g$—N$(R^6)_2$, —$(R^7)_g$—N$(R^6)$Ay, —$(R^7)_g$—N$(R^6)$Het, —$(R^7)_g$—N$(R^6)$C(O)$R^6$, —$(R^7)_g$N$(R^6)$C(O)N$(R^6)_2$, —NO$_2$, —CN, —SCN and —N$_3$, or any subset thereof. More particularly, in one embodiment, each $R^4$ is the same or different and is independently selected from the group consisting of halo, alkyl, —$(R^7)_g$-cycloalkyl, —$(R^7)_g$—C(O)$R^6$, —$(R^7)_g$—CO$_2R^6)_2$, —$(R^7)_g$—C(O)N$(R^6)_2$, —$(R^7)_g$—OR$^6$, —$(R^7)_g$—S(O)$_eR^6$, —$(R^7)_g$—N$(R^6)_2$ and —$(R^7)_g$—N$(R^6)$C(O)$R^6$, or any subset thereof. In one embodiment, each $R^4$ is the same or different and is independently selected from the group consisting of halo, alkyl and —$(R^7)_g$—OR$^6$, or any subset thereof.

Specific examples of particular groups defining $R^4$ include but are not limited to fluoro, chloro, bromo, methyl, ethyl, propyl, isopropyl, butyl, isobutyl, t-butyl, hydroxy, —NHC(O)CH$_3$, —NHSO$_2$CH$_3$ and —SO$_2$NH$_2$.

In one embodiment of the present invention, b is 0, 1, 2 or 3. In one embodiment of the invention, b is 1, 2 or 3. In one particular embodiment, b is 2 or 3. In one particular embodiment, b is 3.

In those embodiments of the present invention wherein b is 1 or more, each $R^5$ is the same or different and is a group of formula $(R^7)_g$—$R^{11}$, or two adjacent $R^5$ groups are each the same or different and are independently selected from the group consisting of alkyl, alkenyl, —OR$^6$, —S(O)$_eR^6$ and —N$(R^6)_2$ and, together with the carbon atoms to which they are bonded, they form a $C_{5-6}$cycloalkyl, $C_{5-6}$cycloalkenyl or a 5- or 6-membered heterocycle or heteroaryl containing 1 or 2 heteroatoms selected from the group consisting of N, O and S. Specific examples of embodiments wherein two adjacent $R^5$ groups together with the carbon atoms to which they are bonded form a $C_{5-6}$cycloalkyl, $C_{5-6}$cycloalkenyl or 5- or 6-membered heterocycle or heteroaryl containing 1 or 2 heteroatoms selected from N, O and S are described above in connection with the description of two adjacent $R^4$ groups forming similar rings.

In one particular embodiment two adjacent $R^5$ groups together with the carbon atoms to which they are bonded do not form a $C_{5-6}$cycloalkyl, $C_{5-6}$cycloalkenyl or 5- or 6-membered heterocycle or heteroaryl containing 1 or 2 heteroatoms selected from N, O and S.

In one embodiment of the present invention, each $R^5$ is the same or different and is a group of formula $(R^7)_g$—$R^{11}$, wherein g is 0. In one embodiment, each $R^5$ is the same or different and is a group of formula $(R^7)_g$—$R^{11}$, wherein g is 1. In one embodiment, each $R^5$ is the same or different and is a group of formula $(R^7)_g$—$R^{11}$, wherein g is 1 and $R^7$ is $C_{1-3}$alkyl.

In one particular embodiment of the present invention, $R^5$ is $(R^7)_g$—$R^{11}$ wherein $R^{11}$ is selected from the group consisting of halo, alkyl, alkenyl, alkynyl, Ay, Het, —C(O)Het, —CO$_2R^6$, —CO$_2$Ay, —CO$_2$Het, —C(O)N(R$^6$)$_2$, —C(O)N(R$^6$)Ay, —C(O)N(R$^6$)Het, —C(O)N(R$^6$)—(R$^7$)$_g$—N(R$^6$)$_2$, —C(O)N(R$^6$)—(R$^7$)$_g$—CO$_2R^6$, —C(O)N(R$^6$)—(R$^7$)$_g$—S(O)$_e$R$^6$, —OR$^6$, —O—(R$^7$)$_g$-Ay, —O—(R$^7$)$_g$-Het, —O—R$^7$—OR$^6$, —O—R$^7$—N(R$^6$)$_2$, —S(O)$_e$R$^6$, —S(O)$_e$—(R$^7$)$_g$-Het, —S(O)$_e$—(R$^7$)$_g$—N(R$^6$)$_2$, —S(O)$_e$—(R$^7$)$_g$—N(R$^6$)Het, —S(O)$_e$N(R$^6$)—(R$^7$)$_g$—C(O)Het, —N(R$^6$)$_2$, —N(R$^6$)—(R$^7$)$_g$-Ay, —N(R$^6$)—(R$^7$)$_g$-Het, —N(R$^6$)—(R$^7$)$_g$—C(O)R$^6$, —N(R$^6$)—C(O)—(R$^7$)$_g$-Het, —N(R$^6$)—C(O)—(R$^7$)$_g$—N(R$^6$)$_2$, —N(R$^6$)—C(O)—(R$^7$)$_g$—N(R$^6$)Het, —N(R$^6$)—C(O)—(R$^7$)$_g$—N(R$^6$)—(R$^7$—O)$_h$—N(R$^6$)—CO$_2R^{61}$—N(R$^6$)—(R$^7$)$_g$—S(O)$_e$R$^6$, —N(R$^6$)—(R$^7$)$_g$—S(O)$_e$Het, —N(R$^6$)—R$^7$—N(R$^6$)$_2$, —N(R$^6$)—R$^7$—OR$^6$, —CN and —N$_3$, or any subset thereof.

More particularly, in one embodiment, $R^{11}$ is selected from the group consisting of halo, alkyl, Ay, Het, —CO$_2R^6$, —C(O)N(R$^6$)$_2$, —OR$^6$, —O—(R$^7$)$_g$-Ay, —O—(R$^7$)$_g$-Het, —S(O)$_e$R$^6$, —S(O)$_e$—(R$^7$)$_g$—N(R$^6$)$_2$, —N(R$^6$)$_2$, —N(R$^6$)—(R$^7$)$_g$-Ay, —N(R$^6$)—(R$^7$)$_g$-Het, —N(R$^6$)—(R$^7$)$_g$—C(O)R$^6$, —N(R$^6$)—C(O)—(R$^7$)$_g$—N(R$^6$)$_2$, —N(R$^6$)—C(O)—(R$^7$)$_g$—N(R$^6$)—(R$^7$—O)$_h$—N(R$^6$)—CO$_2R^6$, —N(R$^6$)—(R$^7$)$_g$—S(O)$_e$R$^6$, —N(R$^6$)—R$^7$—N(R$^6$)$_2$, —CN and —N$_3$, or any subset thereof. In one particular embodiment, $R^{11}$ is selected from the group consisting of alkyl, Het, —OR$^6$, —S(O)$_e$R$^6$, S(O)$_e$—(R$^7$)$_g$—N(R$^6$)$_2$, —N(R$^6$)$_2$, —N(R$^6$)—(R$^7$)$_g$—C(O)R$^6$ and —N(R$^6$)—C(O)—(R$^7$)$_g$—N(R$^6$)$_2$.

Specific examples of particular groups defining $R^{11}$ include but are not limited to —OR$^6$, —S(O)$_2R^6$, —S(O)$_2$—N(R$^6$)$_2$, —N(R$^6$)—C(O)R$^6$, —N(R$^6$)—C(O)—N(R$^6$)$_2$, —N(R$^6$)—SO$_2R^6$ and —N(R$^6$)—SO$_2$Het. More particularly, groups defining $R^{11}$ include but are not limited to —OR$^6$, —S(O)$_2R^6$, —S(O)$_2$—N(R$^6$)$_2$, —N(H)—C(O)R$^6$, —N(H)—C(O)—N(R$^6$)$_2$, —N(H)—SO$_2R^6$ and —N(H)—SO$_2$Het. More specifically, in one embodiment each $R^{11}$ is the same or different and is independently selected from the group consisting of —H, —OCH$_3$, —SO$_2$CH$_3$, —SO$_2$CH$_2$CH$_3$, —SO$_2$N(H)CH$_3$, —SO$_2$CH$_2$CH$_3$, —N(H)—C(O)CH$_3$, —N(H)—C(O)—N(H)(CH$_3$) and —N(H)SO$_2$CH$_3$.

It is to be understood that the present invention includes all combinations and subsets of the particular groups defined hereinabove.

Specific compounds of formula (I) include but are not limited to:

2-({5-nitro-2-[(3,4,5-trimethoxyphenyl)amino]pyrimidin-4-yl}amino)benzoic acid hydrochloride;
2-({5-nitro-2-[(3,4,5-trimethoxyphenyl)amino]pyrimidin-4-yl}amino)benzamide hydrochloride;
N-(tert-butyl)-2-({5-nitro-2-[(3,4,5-trimethoxyphenyl)amino]pyrimidin-4 yl}amino)benzamide hydrochloride;
N-[4-({4-[(2-benzoylphenyl)amino]-5-nitropyrimidin-2-yl}amino)phenyl]acetamide hydrochloride;
8-({5-nitro-2-[(3,4,5-trimethoxyphenyl)amino]pyrimidin-4-yl}amino)-3,4-dihydronaphthalen-1(2H)-one hydrochloride;
1-[2-({5-bromo-2-[(3,4,5-trimethoxyphenyl)amino]pyrimidin-4-yl}amino)phenyl]ethanone hydrochloride;
2-[(2-{[4-(acetylamino)phenyl]amino}-5-nitropyrimidin-4-yl)amino]-N-methylbenzamide hydrochloride;
$N^4$-(1H-indol-4-yl)-5-nitro-$N^2$-(3,4,5-trimethoxyphenyl)pyrimidine-2,4-diamine hydrochloride;
Methyl 2-({5-nitro-2-[(3,4,5-trimethoxyphenyl)amino]pyrimidin-4-yl}amino)benzoate hydrochloride;
$N^4$-(2,3-dihydro-1,4-benzodioxin-5-yl)-5-nitro-$N^2$-(3,4,5-trimethoxyphenyl)pyrimidine-2,4-diamine hydrochloride;
Cyclohexyl 2-[(2-{[4-(acetylamino)phenyl]amino}-5-nitropyrimidin-4-yl)amino]benzoate hydrochloride;
5-Hydroxy-2-({5-nitro-2-[(3,4,5-trimethoxyphenyl)amino]pyrimidin-4-yl}amino)benzoic acid hydrochloride;
2-[(2-{[4-(Acetylamino)phenyl]amino}-5-nitropyrimidin-4-yl)amino]benzoic acid hydrochloride;
N-[4-({4-[(2-Acetylphenyl)amino]-5-bromopyrimidin-2-yl}amino)phenyl]acetamide hydrochloride;
N-[4-({5-Bromo-4-[(2-morpholin-+ylphenyl)amino]pyrimidin-2-yl}amino)phenyl]acetamide hydrochloride;
5-[(5-Bromo-4-{[2-(methylthio)phenyl]amino}pyrimidin-2-yl)amino]-1,3-dihydro-2H-benzimidazol-2-one hydrochloride;
5-Bromo-$N^4$-(2-morpholin-4-ylphenyl)-$N^2$-(3,4,5-trimethoxyphenyl)pyrimidine-2,4-diamine hydrochloride;
N-[4-({5-Bromo-4-[(3,4,5-trimethoxyphenyl)amino]pyrimidin-2-yl}amino)phenyl]acetamide hydrochloride;
Dimethyl 2-[(2-{[4-(acetylamino)phenyl]amino}-5-nitropyrimidin-4-yl)amino]terephthalate hydrochloride;
Benzyl 2-[(2-{[4-(acetylamino)phenyl]amino}-5-nitropyrimidin-4-yl)amino]benzoate hydrochloride;
Methyl 2-[(2-{[4-(acetylamino)phenyl]amino}-5-nitropyrimidin-4-yl)amino]-6-methylbenzoate hydrochloride;
Isobutyl 2-[(2-{[4-(acetylamino)phenyl]amino}-5-nitropyrimidin-4-yl)amino]benzoate hydrochloride;
2-[(2-{[4-(Acetylamino)phenyl]amino}-5-nitropyrimidin-4-yl)amino]-6-methylbenzoic acid hydrochloride;
N-Cyclohexyl-2-({5-nitro-2-[(3,4,5-trimethoxyphenyl)amino]pyrimidin-4-yl}amino)benzamide hydrochloride;
1-[2-({5-Nitro-2-[(3,4,5-trimethoxyphenyl)amino]pyrimidin-4-yl}amino)phenyl]ethanone hydrochloride;
[5-Chloro-2-({5-nitro-2-[(3,4,5-trimethoxyphenyl)amino]pyrimidin-4-yl}amino)phenyl](2-fluorophenyl)methanone hydrochloride;
8-({5-Nitro-2-[(3,4,5-trimethoxyphenyl)amino]pyrimidin-4-yl}amino)-2-naphthol hydrochloride;
N-(tert-butyl)-2-({5-methyl ketone-2-[(3,4,5-trimethoxyphenyl)amino]pyrimidin-4-yl}amino)benzamide;
4-{[2-(4-Methylbenzoyl)phenyl]amino}-2-[(3,4,5-tri methoxyphenyl)amino]-pyrimidine-5-carbonitrile and pharmaceutically acceptable salts, solvates and physiologically functional derivatives thereof.

It will be appreciated by those skilled in the art that the compounds of the present invention may also be utilized in the form of a pharmaceutically acceptable salt or solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like.

Other acids such as oxalic, while not in themselves pharmaceutically acceptable, may be useful in the preparation of salts which are useful as intermediates in obtaining the compounds of the invention or pharmaceutically acceptable salts thereof. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Certain compounds of formula (I) may be prepared as a mixture of regioisomers. The present invention covers both the mixture of regioisomers as well as the individual compounds. Likewise, it is understood that compounds of formula (I) may exist in tautomeric forms other than that shown in the formula and these are also included within the scope of the present invention.

The compounds of the present invention are typically inhibitors of PLK. By "PLK inhibitor" is meant a compound which exhibits $pIC_{50}$ greater than 4 in the PLK Inhibition assay described below in the examples or an $IC_{50}$ less than 100 μM in the Methylene Blue Growth Inhibition assay described below in the examples; more particularly a PLK inhibitor is a compound which exhibits a $pIC_{50}$ greater than 5 or an $IC_{50}$ less than 10 μM using the methods described in the examples below.

The present invention further provides compounds of formula (I) for use in medical therapy in an animal, e.g. a mammal such as a human. In particular, the present invention provides compounds of formula (I) for use in the treatment of a condition mediated by PLK. The present invention also provides compounds of formula (I) for use in the treatment of a susceptible neoplasm. The present invention provides compounds of formula (I) for use in treating a condition characterized by inappropriate cellular proliferation. The present invention also provides compounds of formula (I) for use in inhibiting proliferation of a cell. The present invention also provides compounds of formula (I) for use in inhibiting mitosis in a cell.

The present invention provides methods for the treatment of several conditions or diseases, all of which comprise the step of administering a therapeutically effective amount of a compound of formula (I). As used herein, the term "treatment" refers to alleviating the specified condition, eliminating or reducing the symptoms of the condition, slowing or eliminating the progression of the condition and preventing or delaying the reoccurrance of the condition in a previously afflicted subject.

As used herein, the term "therapeutically effective amount" means an amount of a compound of formula (I) which is sufficient, in the subject to which it is administered, to elicit the biological or medical response of a cell culture, tissue, system, animal (including human) that is being sought, for instance, by a researcher or clinician. For example, a therapeutically effective amount of a compound of formula (I) for the treatment of a condition mediated by PLK is an amount sufficient to treat the PLK mediated condition in the subject. Similarly, a therapeutically effective amount of a compound of formula (I) for the treatment of a susceptible neoplasm is an amount sufficient to treat the susceptible neoplasm in the subject. In one embodiment of the present invention, the therapeutically effective amount of a compound of formula (I) is an amount sufficient to inhibit cell mitosis. In one embodiment of the present invention, a therapeutically effective amount of a compound of formula (I) is an amount sufficient to regulate, modulate, bind or inhibit PLK.

The precise therapeutically effective amount of the compounds of formula (I) will depend on a number of factors including, but not limited to, the age and weight of the subject being treated, the precise disorder requiring treatment and its severity, the nature of the formulation, and the route of administration, and will ultimately be at the discretion of the attendant physcian or veternarian. Typically, the compound of formula (I) will be given for treatment In the range of 0.1 to 200 mg/kg body weight of recipient (animal) per day and more usually in the range of 1 to 100 mg/kg body weight per day. Acceptable daily dosages, may be from about 0.1 to about 2000 mg/day, and preferably from about 0.1 to about 100 mg/day.

As one aspect, the present invention provides methods of regulating, modulating, binding, or inhibiting PLK for the treatment of conditions mediated by PLK. "Regulating, modulating, binding or inhibiting PLK" refers to regulating, modulating, binding or inhibiting PLK activity, as well as regulating, modulating, binding or inhibiting overexpression of PLK. Such conditions include certain neoplasms (including cancers and tumors) which have been associated with PLK and conditions characterized by inappropriate cellular proliferation.

The present invention provides a method for treating a condition mediated by PLK in an animal such as a mammal (e.g., a human), which method comprises administering to the animal a therapeutically effective amount of the compound of formula (I). Conditions which are mediated by PLK are known in the art and include but are not limited to neoplasms and conditions characterized by inappropriate cellular proliferation.

The present invention also provides a method for treating a susceptible neoplasm (cancer or tumor) in an animal such as a mammal (e.g., a human), which method comprises administering to the animal a therapeutically effective amount of the compound of formula (I). "Susceptible neoplasm" as used herein refers to neoplasms which are susceptible to treatment with a PLK inhibitor. Neoplasms which have been associated with PLK and are therefore susceptible to treatment with a PLK inhibitor are known in the art, and include both primary and metastatic tumors and cancers. For example, susceptible neoplasms within the scope of the present invention include but are not limited to breast cancer, colon cancer, lung cancer (including small cell lung cancer and non-small cell lung cancer), prostate cancer, lymphoma, leukemia, endometrial cancer, melanoma, ovarian cancer, pancreatic cancer, squamous carcinoma, carcinoma of the head and neck, and esophageal carcinoma. The compounds of formula (I) can be used alone in the treatment of such susceptible neoplasms or can be used to provide additive or synergistic effects with certain existing chemotherapies, and/or be used to restore effectiveness of certain existing chemotherapies and radiation.

The present invention also provides a method for treating a condition characterized by inappropriate cellular proliferation. By "inapproriate cellular proliferation" is meant cellular proliferation resulting from inappropriate cell growth, cellular proliferation resulting from excessive cell division, cellular proliferation resulting from cell division at an accelerated rate, cellular proliferation resulting from inappropriate cell survival, and/or cellular proliferation in a normal cell occurring at a normal rate, which is neverthless undesired. Conditions characterized by inappropriate cellular proliferation include but are not limited to neoplasms, blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, malignant nephrosclerosis, thrombotic microangiopathy syndromes, organ transplant rejection and glomerulopathies. Metabolic disorders include psoriasis, chronic wound healing, inflammation and neurodegenerative diseases. Osteoarthritis and other osteoclast proliferation dependent diseases of excess bone resorbtion are examples of conditions characterized by inapproprate cellular proliferation in which the cellular proliferation occurs in normal cells at a normal rate, but is nevertheless undesired.

The present invention also provides a method for inhibiting proliferation of a cell, which method comprises contacting the cell with an amount of a compound of formula (I) sufficient to inhibit proliferation of the cell. In one particular embodiment, the cell is a neoplastic cell. In one particular embodiment, the cell is an inappropriately proliferative cell. The term "inappropriately proliferative cell" as used herein refers to cells that grow inappropriately (abnormally), cells that divide excessively or at an accelerated rate, cells that inappropriately (abnormally) survive and/or normal cells that proliferate at a normal rate but for which proliferation is undesired.

Neoplastic cells (including cancer cells) are an example of inappropriately proliferative cells but are not the only inappropriately proliferative cells.

PLK is essential for cellular mitosis and accordingly, the compounds of formula (I) are effective for inhibiting mitosis. "Inhibiting mitosis" refers to inhibiting the entry into the M phase of the cell cycle, inhibiting the normal progression of the M phase of the cell cycle once M phase has been entered and inhibiting the normal exit from the M phase of the cell cycle. Thus, the compounds of the present invention may inhibit mitosis by inhibiting the cell's entry into mitosis, by inhibiting the cell's progression through mitosis or by inhibiting the cell's exit from mitosis. As one aspect, the present invention provides a method for inhibiting mitosis in a cell, which method comprises administering to the cell an amount of a compound of formula (I) sufficient to inhibit mitosis. In one particular embodiment, the cell is a neoplastic cell. In one particular embodiment, the cell is an inappropriately proliferative cell.

The present invention also provides the use of a compound of formula (I) for the preparation of a medicament for the treatment of condition mediated by PLK in an animal, such as a mammal (e.g., a human). The present invention further provides the use of a compound of formula (I) for the preparation of a medicament for the treatment of a susceptible neoplasm in an animal. The present invention further provides the use of a compound of formula (I) for the preparation of a medicament for the treatment of a condition characterized by inappropriate cellular proliferation. The present invention further provides the use of a compound of formula (I) for the preparation of a medicament for Inhibiting proliferation of a cell. The present invention further provides the use of a compound of formula (I) for the preparation of a medicament for inhibiting mitosis in a cell.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers, diluents and/or excipients.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders Include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be delivered by the use of monoclonal antibodies as individual carriers to which the compound molecules are coupled. The compounds may also be coupled with soluble polymers as targetable drug carriers. Such polymers can include peptides, polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile Injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. In particular, in methods of treating conditions mediated by PLK and methods of treating susceptible neoplasms, combination with other chemotherapeutic, hormonal and/or antibody agents is envisaged as well as combination with surgical therapy and radiotherapy. The term "chemotherapeutic" as used herein refers to any chemical agent having a therapeutic effect on the subject to which it is administered. "Chemotherapeutic" agents include but are not limited to anti-neoplastic agents, analgesics and anti-emetics. As used herein, "anti-neoplastic agents" include both cytostatic and cytotoxic agents, Combination therapies according to the present invention thus comprise the administration of at least one compound of formula (I) and the use of at least one other cancer treatment method. In one embodiment, combination therapies according to the present invention comprise the administration of at least one compound of formula (I) and at least one other chemotherapeutic agent. In one particular embodiment, the present invention comprises the administration of at least one compound of formula (I) and at least one anti-neoplastic agent. As an additional aspect, the present invention provides the methods of treatment and uses as described above, which comprise administering a compound of formula (I) together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

Typically, any chemotherapeutic agent that has activity versus a susceptible neoplasm being treated may be utilized in combination with the compounds of formula (I), provided that the particular agent is clinically compatible with therapy employing a compound of formula (I). Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine.

Platinum coordination complexes are non-phase specific anti-neoplastic agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Alkylating agents are non-phase anti-neoplastic specific agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine and thioguanine. Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin.

Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorti-costeroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr, ErbB2 and ErbB4,), platelet derived growth factor receptor (PDGFr), vascular endothelial growth factor receptor (VEGFR), tyrosine kinase with immunoglobulin-like and epidermal growth factor homology domains (TIE-2), insulin growth factor-I receptor (IGF-I), macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth Factor Receptors as Targets", New Molecular Targets for Cancer Chemotherapy, Ed. Workman, Paul and Kerr, David, CRC Press 1994, London.

Tyrosine kinases, which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases Including MAP kinase cascade blockers which include blockers of Raf kinases (Raf), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; and Martinez-Iacaci, L., et al, Int. J. Cancer (2000), 88(1), 44-52.

Inhibitors of Phosphotidyl Inositol-3 Kinase family members including blockers of PI3-kinase, ATM, DNA-PK, and Ku are also useful in combination with the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9(2)99-102; and BioChim. Biophys. Acta, (1989) 1423(3):19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer:ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124).

Receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with PLK inhibitors.

Agents used in immunotherapeutic regimens may also be useful in combination with the compounds of formula (I).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., *J. Clin, Oncol.* 18:1812-1823 (2000); and Kitada S et al., *Antisense Res. Dev.* 4:71-79 (1994).

Cell cycle signaling inhibitors inhibit molecules involved in the control of the cell cycle. Cyclin dependent kinases (CDKs) and their interaction cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin. Ther. Patents* 10(2):215-230 (2000).

In one embodiment, the methods of the present invention comprise administering to the animal a compound of formula (I) in combination with a signal transduction pathway inhibitor, particularly gefitinib (IRESSA®).

The methods and uses employing these combinations may comprise the administration of the compound of formula (I) and the other chemotherapeutic/anti-neoplastic agent either sequentially in any order or simultaneously in separate or combined pharmaceutical compositions. When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a chemotherapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendent clinician.

Compounds of formula (I) may be conveniently prepared by the process outlined in Scheme 1 below.

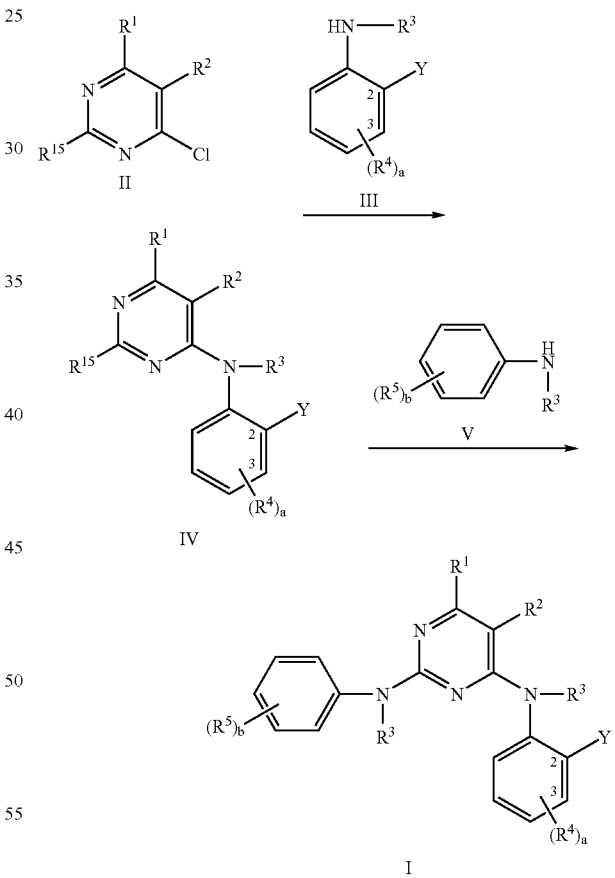

wherein:
R$^1$ is selected from the group consisting of H, halo, alkyl, alkenyl, alkynyl;
R$^2$ is selected from the group consisting of halo, alkyl, alkenyl, alkynyl, cycloalkyl, cycloalkenyl, —(R$^7$)$_g$—C(O)R$^6$, —(R$^7$)$_g$—CO$_2$R$^6$, —(R$^7$)$_g$—C(O)N(R$^6$)$_2$, —(R$^7$)$_g$—OR$^6$, —O—(R$^7$)$_g$-Ay, —(R$^7$)$_g$—S(O)$_e$R$^6$, —(R$^7$)$_g$—N(R$^6$)$_2$, —(R$^7$)$_g$—N(R$^6$)C(O)R$^6$, —(R$^7$)$_g$—CN, —(R$^7$)$_g$—SCN, —$NO_2$, —$N_3$, Ay and 5- to 9-membered heteroaryl containing 1 or 2 heteroatoms selected from N, O and S;

each $R^3$ is the same or different and is independently H or alkyl;

Y is selected from the group consisting of —$C(O)R^8$, —$C(S)R^8$, —$S(O)_eR^9$, —$S(O)_eN(R^9)_2$, —$N(R^9)_2$, —$N(R^9)$—$S(O)_eR^9$, —$N(R^9)$—$C(O)R^9$, —$N(R^9)$—$CO_2R^9$, and —$N(R^9)$—$C(O)N(R^9)_2$, or Y, together with C-2 and C-3 form a fused ring system of formula A:

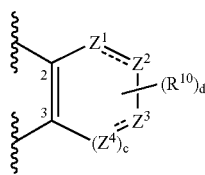

wherein $R^8$ is selected from the group consisting of alkyl, alkenyl, alkynyl, cycloalkyl, cycloalkenyl, Ay, Het, —$OR^6$, —O—$(R^7)_g$-Ay, —O—$(R^7)_g$-Het, —$N(R^6)_2$, —$N(R^6)$—$(R^7)_g$-Ay, —$N(R^6)$—$(R^7)_g$-Het, —$N(R^6)$—$(R^7)_g$—$OR^6$, —$N(R^6)$—$(R^7)_g$—$C(O)R^6$, —$N(R^6)$—$(R^7)_g$—$CO_2R^6$, —$N(R^6)$—$(R^7)_g$—$SO_2R^6$, and —$N(R^6)$—$(R^7)_g$—$N(Re)_2$;

each $R^9$ is the same or different and is independently selected from the group consisting of H, alkyl, alkenyl, alkynyl, cycloalkyl, cycloalkenyl, Ay and Het;

c is 0 or 1;

$Z^1$, $Z^2$, $Z^3$ and $Z^4$ are each independently selected from the group consisting of C, O, S and N, wherein when c is 0, at least one of $Z^1$, $Z^2$ and $Z^3$ is C and wherein when c is 1, at least two of $Z^1$, $Z^2$, $Z^3$ and $Z^4$ are C;

each dashed line represents an optional double bond;

d is 0, 1 or 2;

each $R^{10}$ is the same or different and is independently selected from the group consisting of halo, alkyl, oxo, hydroxy, mercapto and amino;

a is 0, 1, 2 or 3;

each $R^4$ is the same or different and is independently selected from the group consisting of halo, alkyl, alkenyl, alkynyl, —$(R^7)_g$-cycloalkyl, —$(R^7)_g$-cycloalkenyl, —$(R^7)_g$-Ay, —$(R^7)_g$-Het, —$(R^7)_g$—$C(O)R^6$, —$(R^7)_g$—$C(O)Ay$, —$(R^7)_g$—$C(O)Het$, —$(R^7)_g$—$CO_2R^6$, —$(R^7)_g$—$CO_2Ay$, —$(R^7)_g$—$CO_2Het$, —$(R^7)_g$—$C(O)N(R^6)_2$, —$(R^7)_g$—$OR^6$, —$(R^7)_g$—$OAy$, —$(R^7)_g$—$OHet$, —$(R^7)_g$—$OC(O)R^6$, —$(R^7)_g$—$OC(O)Ay$, —$(R^7)_g$—$OC(O)Het$, —$(R^7)_g$—$S(O)_eR^6$, —$(R^7)_g$—$S(O)_eAy$, —$(R^7)_g$—$S(O)_eHet$, —$(R^7)_g$—$S(O)_eN(R^6)_2$, —$(R^7)_g$—$S(O)_eN(R^6)Ay$, —$(R^7)_g$—$S(O)_eN(R^6)Het$, —$(R^7)_g$—$N(R^6)_2$, —$(R^7)_g$—$N(R^6)Ay$, —$(R^7)_g$—$N(R^6)Het$, —$(R^7)_g$—$N(R^6)C(O)R^6$, —$(R^7)_g$—$N(R^6)C(O)Ay$, —$(R^7)_g$—$N(R^6)C(O)Het$, —$(R^7)_g$—$N(R^6)C(O)N(R^6)_2$, —$(R^7)_g$—$N(R^6)S(O)_eR^6$, —$(R^7)_g$—$N(R^6)S(O)_eAy$, —$(R^7)_g$—$N(R^6)S(O)_eHet$, —$NO_2$, —CN, —SCN and —$N_3$, or two adjacent $R^4$ groups together with the carbon atoms to which they are bonded form a phenyl or a 5- or 6-membered heterocycle or heteroaryl containing 1 or 2 heteroatoms selected from the group consisting of O, N and S;

each e is the same or different and is independently 0, 1 or 2;

b is 0, 1, 2, 3, 4 or 5;

each $R^5$ is the same or different and is a group of formula $(R^7)_g$—$R^{11}$, or two adjacent $R^5$ groups are each the same or different and are independently selected from the group consisting of alkyl, alkenyl, —$OR^6$, —$S(O)_eR^6$ and —$N(R^6)_2$ and, together with the carbon atoms to which they are bonded, they form a $C_{5-6}$cycloalkyl, $C_{5-6}$cycloalkenyl or a 5- or 6-membered heterocycle or heteroaryl containing 1 or 2 heteroatoms selected from the group consisting of N, O and S;

each $R^6$ is the same or different and is independently selected from the group consisting of H, alkyl, alkenyl, alkynyl, cycloalkyl and cycloalkenyl;

g is 0 or 1;

$R^7$ is alkylene or alkenylene;

Ay is aryl;

Het is a 5- or 6-membered heterocycle or heteroaryl containing 1, 2 or 3 heteroatoms selected from the group consisting of N, O and S;

$R^{11}$ is selected from the group consisting of halo, alkyl, alkenyl, alkynyl, cycloalkyl, cycloalkenyl, Ay, Het, —$C(O)R^6$, —$C(O)Ay$, —$C(O)Het$, —$CO_2R^6$, —$CO_2Ay$, —$CO_2Het$, —$C(O)$—$R^7$—$OR^6$, —$C(O)$—$R^7$—$OAy$, —$C(O)$—$R^7$—$OHet$, —$C(O)N(R^6)_2$, —$C(O)N(R^6)Ay$, —$C(O)N(R^6)Het$, —$C(O)N(R^6)$—$(R^7)_g$—$N(R^6)_2$, —$C(O)N(R^6)$—$(R^7)_g$—$CO_2R^6$, —$C(O)N(R^6)$—$(R^7)_g$—$S(O)_eR^6$, —$OR^6$, —$OC(O)R^6$, —O—$(R^7)_g$-Ay, —$OC(O)Ay$, —O—$(R^7)_g$-Het, —$OC(O)Het$, —O—$R^7$—$OR^6$, —O—$R^7$—$N(R^6)_2$, —$S(O)_eR^6$, —$S(O)_e$—$(R^7)_g$-Ay, —$S(O)_e$—$(R^7)_g$-Het, —$S(O)_e$—$(R^7)_g$—$N(R^6)_2$, —$S(O)_e$—$(R^7)_g$—$N(R^6)Ay$, —$S(O)_e$—$(R^7)_g$—$N(R^6)Het$, —$S(O)_eN(R^6)$—$(R^7)_g$—$C(O)R^6$, —$S(O)_eN(R^6)$—$(R^7)_g$—$C(O)Ay$, —$S(O)_eN(R^6)$—$(R^7)_g$—$C(O)Het$, —$N(R^6)_2$, —$N(R^6)$—$(R^7)_g$-Ay, —$N(R^6)$—$(R^7)_g$-Het, —$N(R^6)$—$(R^7)_g$—$C(O)R^6$, —$N(R^6)$—$C(O)$—$(R^7)_g$-Ay, —$N(R^6)$—$C(O)$—$(R^7)_g$-Het, —$N(R^6)$—$C(O)$—$(R^7)_g$—$N(R^6)_2$, —$N(R^6)$—$C(O)$—$(R^7)_g$—$N(R^6)Ay$, —$N(R^6)$—$C(O)$—$(R^7)_g$—$N(R^6)Het$, —$N(R^6)$—$C(O)$—$(R^7)_g$—$N(R^6)$—$(R^7$—$O)_h$—$N(R^6)$—$CO_2R^6$, —$N(R^6)$—$(R^7)_g$—$S(O)_eR^6$, —$N(R^6)$—$(R^7)_g$—$S(O)_eAy$, —$N(R^6)$—$(R^7)_g$—$S(O)_eHet$, —$N(R^6)$—$R^7$—$N(R^6)_2$, —$N(R^6)$—$R^7$—$OR^6$, —CN, —SCN, —$NO_2$, and —$N_3$;

h is 1-20; and $R^{15}$ is selected from the group consisting of halo and —$S(O)_eR^6$.

Generally, compounds of formula (I) can be prepared a process comprising:

a) reacting a compound of formula (II) with a compound of formula (III) to prepare a compound of formula (IV); and b) reacting a compound of formula (IV) with a compound of formula (V) to prepare a compound of formula (I).

More specifically, a compound of formula (I) may be prepared by reacting a compound of formula (IV) with a compound of formula (V).

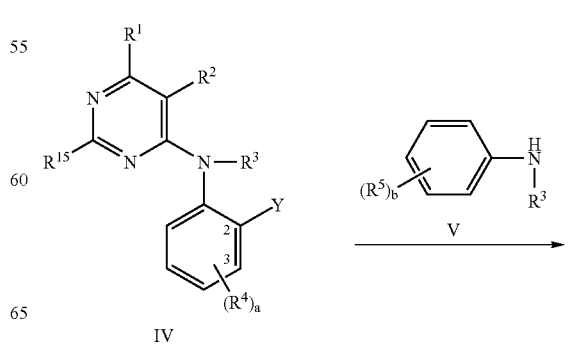

-continued

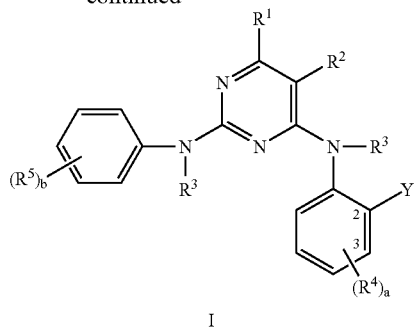

I

The reaction may be carried out in an inert solvent, in the presence of an acid catalyst. The reaction may be optionally heated to from about 50 to about 150° C. In one embodiment, the reaction is carried out at about 90° C. In one embodiment, the reaction is carried out using equimolar amounts of the aniline compound of formula (V) and the compound of formula (IV). However, the reaction may also be performed in the presence of an excess of the compound of formula (V). The acid catalyst is typically present in an amount of 10-30 mol % compared to the compound of formula (IV). An example of a suitable acid catalyst is hydrochloric acid although other acids may be employed as will be appreciated by those skilled in the art. Suitable inert solvents include but are not limited to isopropyl alcohol, ethanol, dioxane, tetrahydrofuran, dichloromethane and N,N-dimethylformamide. The aniline compounds of formula (V) may be obtained from commercial sources or prepared as discreet isolated compounds using methods known to those skilled in the art.

In certain embodiments, it may be advantageous to oxidize the compound of formula (IV) prior to reacting with the compound of formula (V). For example, in the embodiment wherein the compound of formula (IV) is defined wherein $R^{15}$ is S-alkyl (i.e., a compound of formula (IV-A) below), the compound of formula (IV-A) may be oxidized to a compound of formula (IV-B), wherein $R^{15}$ is $S(O)_2$-alkyl.

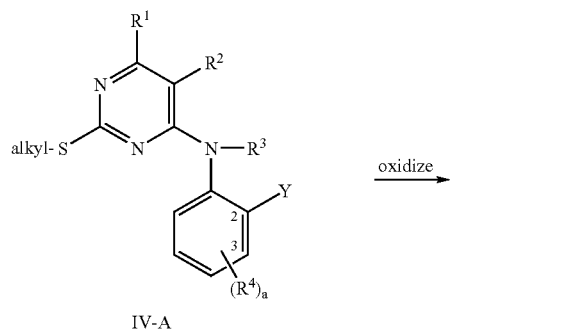

Such oxidation may be carried out using conventional techniques and oxidizing agents, such as 3-chloroperoxybenzoic acid, oxone, hydrogen peroxide, potassium permanganate, and the like. The oxidation may be carried out in a suitable solvent, such as dichlormethane, chloroform, carbontetrachloride, aqueous acidic acid, or the like. Based upon this specific example and general principles of organic synthesis, one skilled in the art will appreciate other specific instances wherein the oxidation of a compound of formula (IV) may be desired prior to reacting with the compound of formula (V) and will similarly appreciate appropriate reaction conditions for carry-out such oxidations for other specific compounds.

A compound of formula (IV) may be prepared by reacting a compound of formula (II) with a compound of formula (III).

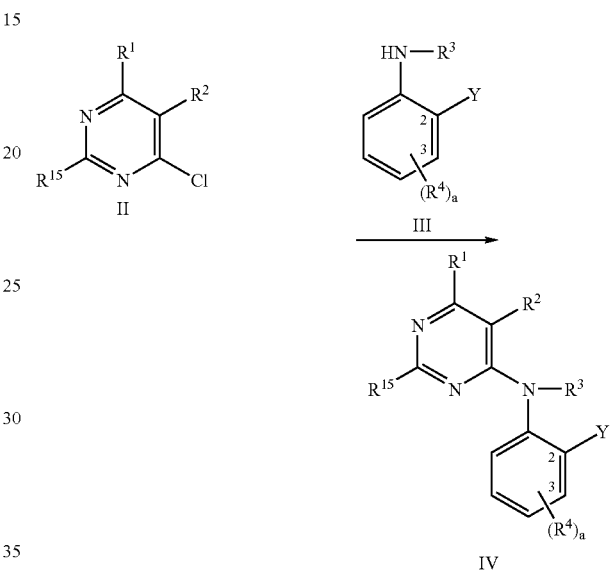

The reaction may be carried out in an inert solvent, in the presence of a base. The reaction temperature will vary from up to about 100° C., depending upon the particular compounds of formula (II) and (III) employed. In one embodiment, the reaction is carried out at reduced temperature, e.g., about −78° C. In another embodiment, the reaction is carried out at elevated temperature, e.g., from about 50 to about 80° C. In one embodiment, the reaction is carried out using equimolar amounts of the compound of formula (II) and the compound of formula (III). However, the reaction may also be preformed in the presence of an excess amount of the compound of the formula (II). The base is typically present in a proportion equivalent to, or greater than, that of the compound of formula (II). Examples of suitable bases include but are not limited to diisopropylethylamine, triethylamine, sodium carbonate and sodium bicarbonate. The reaction may be carried out in a suitable solvent. Examples of suitable solvents include but are not limited to ethanol, isopropyl alcohol, dioxane and tetrahydrofuran. The compounds of formula (III) may be obtained from commercial sources or prepared as discreet isolated compounds using methods known to those skilled in the art.

The compounds of formula (II) may be obtained from commercial sources or prepared as discreet isolated compounds using conventional organic synthesis techniques. For example, a compound of formula (II-A), wherein $R^2$ is $-NO_2$ or $-CO_2H$, and $R^{15}$ is Cl, may be prepared by chlorinating a compound of formula (X).

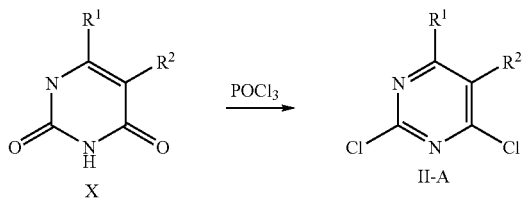

This chlorination can be carried out by treating the compound of formula (X) with phosphorous oxychloride in the presence of a base. Typical bases include but are not limited to N,N-dimethylaniline and pyridine. The reaction may be heated from 30-115° C. Compounds of formula (X) are commercially available.

If desired, the compound of formula (II-A) may be further converted into another compound of formula (II) before proceeding with the reaction with the compound of formula (III). For example, a compound of formula (II-A) wherein $R^2$ is —$CO_2H$, may be converted to a compound of formula (II-B) wherein $R^2$ is —C(O)Cl, which may in turn be converted to a compound of formula (II-C), wherein $R^2$ is —$CO_2R^6$ as follows.

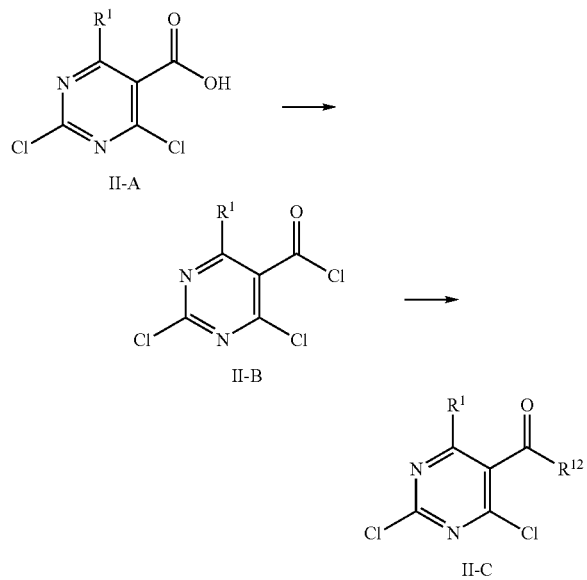

wherein $R^{12}$ is selected from the group consisting of —$R^6$ and —$N(R^6)_2$, and all other variables are as defined above.

A compound of formula (II-A) may be converted to a compound of formula (II-B) by a chlorination procedure. Typically the chlorination reaction is carried out by subjecting the compound of formula (II-A) to an appropriate inorganic acid halide reagent in a suitable solvent. Suitable inorganic acid halide reagents include but are not limited to thionyl chloride, and oxalyl choride. Suitable solvents include, for example tetrahydrofuran, benzene, dichloromethane, and the like.

The compound of formula (II-B) may be further converted to a compound of formula (II-C) by reacting with an alcohol of formula HO—$R^6$ or an amine of formula $HN(R^6)_2$, depending upon whether the ester or amide compound of formula (II-C) is desired. The reaction may be carried out in an inert solvent in the presence of a base and optionally cooled from −78° C. to room temperature. Typically, the reaction is performed by reacting equimolar amounts of the compound of formula (II-B) with the alcohol or amine. The reaction is more conveniently carried out by adding a base in a proportion equivalent to or greater than, that of the compound of formula (II-B).

Suitable bases include but are not limited to pyridine, triethylamine, and diisopropylethylamine. Suitable solvents include but are not limited to dichloromethane, benzene, pyridine and tetrahydrofuran. The alcohol and amine compounds may be obtained from commercial sources or prepared as discreet isolated compounds using methods known to those skilled in the art. (See e.g., Choi, V. *Org. Lett.* 2002 4, 589.)

As another example, a compound of formula (II-D), wherein $R^2$ is CN and $R^{15}$ is alkyl-S, may be prepared by chlorinating a compound of formula (XI).

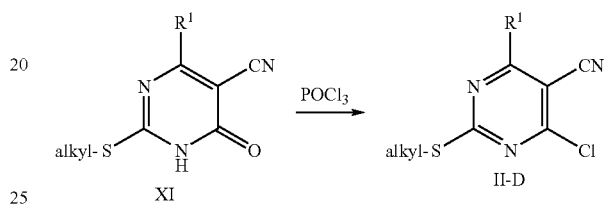

This chlorination can be carried out by treating the compound of formula (XI) with phosphorous oxychloride. The reaction may be heated from 30-115° C. Compounds of formula (XI) are commercially available or can be prepared using conventional techniques. See, e.g., A. Santilli, *J. Heterocycl. Chem.* 8:445 (1971).

As another example, 2,4,6-trichloropyrimidine may be converted to a compound of formula (II-E) (i.e., a compound of formula (II) wherein $R^1$ is alkyl, alkenyl or alkynyl, by reacting with a suitable boronic acid.

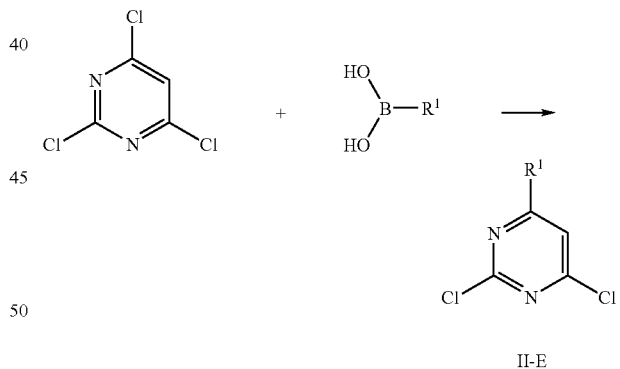

The reaction may be carried out in an inert solvent, in the presence of a palladium (0) catalyst and a base. The reaction may optionally be heated to a temperature of from about 65 to about 100° C. Preferably the reaction is performed by reacting equimolar amounts of 2,4,6-trichloropyrimidine and a boronic acid of the foregoing formula. The palladium catalyst is typically present in 3-10 mol % compared to the pyrimidine. Examples of suitable palladium catalysts include but are not limited to tetrakis(tri-phenylphosphine)palladium (0), and dichlorobis(triphenylphosphine)palladium (II). Suitable bases include but are not limited to potassium carbonate, sodium hydroxide and cesium carbonate. Suitable solvents include but are not limited to tetrahydrofuran, 1,4-doxane and 1,2-dimethoxyethane. Boronic acids having the foregoing formula may be obtained from commercial sources or prepared as discreet isolated compounds using methods known to one skilled in the art. See, Molander G. *Tetrahedron* 2002, 58, 1465; Shiota, T. *J. Org. Chem.* 1999, 64, 453; and Organ, M. G. *Tet. Lett.* 2000, 41, 6945).

Compounds of formula (II) wherein $R^1$ is alkynyl may also be prepared by reacting 2,4,6-trichloropyrimidine with an alkyne. The reaction may be carried out in an inert solvent, in the presence of a palladium (0) catalyst, copper iodide and a base. The reaction may optionally be heated to a temperature of from about 65 to about 100° C. Typically, the reaction is performed by reacting equimolar amounts of trichloropyrimidine and the alkyne. The palladium catalyst is preferably present in 4-10 mol % compared to trichloropyrimidine. Examples of suitable palladium catalysts include but are not limited to tetrakis(triphenylphosphine)palladium (0), and dichlorobis(triphenyl-phosphine)palladium (II). The copper iodide is typically present in 30-40 mol % compared to trichloropyrimidine. Suitable bases include diisopropylamine, diethylamine and triethylamine. Suitable solvents include but are not limited to N,N-dimethylformamide, N-methylpyrrolidinone and 1,4-dioxane.

In addition to processes for preparing a compound of formula (I), the present invention also provides intermediates useful in processes for preparing compounds of formula (I). Such intermediates are depicted in Scheme 1 above and include, for example, compounds of formula (IV).

As will be apparent to those skilled in the art, a compound of formula (I) may be converted to another compound of formula (I) using techniques well known in the art. Similarly, an isolatable intermediate used in the process of preparing a compound of formula (I), such as a compound of formula (II), (IV), or (V) may be converted into a different compound having that same formula. For example, a compound of formula (I-A) above may optionally be converted to a compound of formula (I-B).

A compound of formula (I-A) may be converted to a compound of formula (I-B) by reading a compound of formula (I-A) with an alkylborane compound, such as an alkyl borane compound of formula (XII):

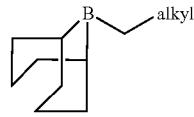

XII

The reaction may be carried out in an inert solvent, in the presence of a palladium (0) catalyst and a base. The reaction may optionally be heated to from about 65 to about 100° C. In one embodiment, the reaction is carried out by reacting equimolar amounts of a compound of formula (I-A) and the alkylborane, but the reaction may also be performed in the presence of an excess of alkylborane. The palladium catalyst is typically present in an amount of from about 1 to about 10 mol % compared to the compound of formula (I-A). Examples of suitable palladium catalysts include but are not limited to tetrakis(triphenylphosphine)palladium (0), dichlorobis(triphenyl-phosphine)palladium (II), and palladium acetate (II) with 2-(di-tert-butylphosphino)biphenyl. The base is typically present in a proportion equivalent to or greater than 200 mol % of the compound of formula (I-A). Suitable bases include but are not limited to potassium phosphate, potassium carbonate, sodium hydroxide and cesium carbonate. Suitable inert solvents include but are not limited to toluene, N,N-dimethylformamide, and tetrahydrofuran. Alkylborane can conveniently be generated in situ using methods known to one skilled in the art. See, De Lera, Angel R. *Tetrahedron* 2001, 57, 3125). This same conversion may be employed to convert a compound of formula (IV) wherein $R^2$ is Br to a compound of formula (IV) wherein $R^2$ is alkyl.

As a second example, a compound of formula (I-A) may be converted to a compound of formula (I-C).

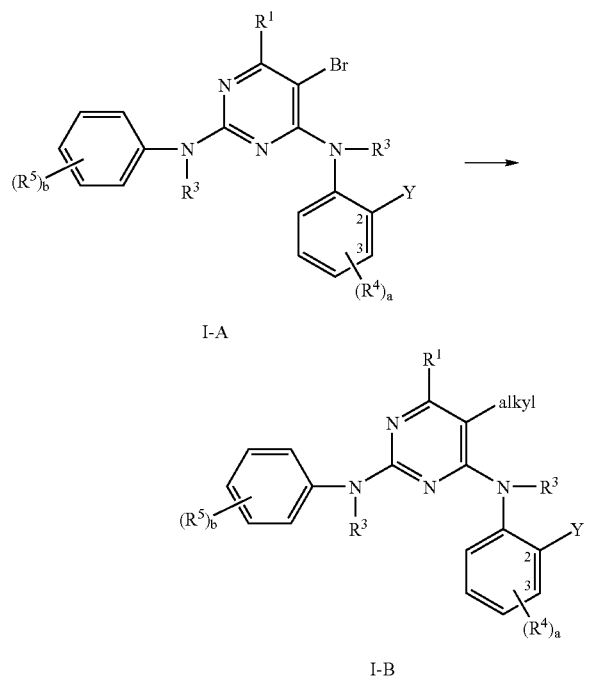

I-A

I-B

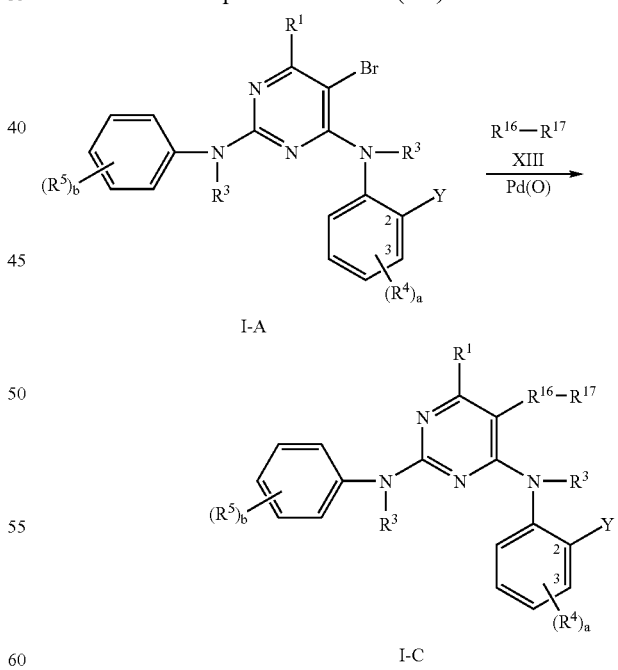

I-A

I-C wherein all variables are as defined above.

wherein:

$R^{16}$ is alkenyl or alkynyl;

$R^{17}$ is selected from the group consisting of $R^2$ is selected from the group consisting of alkyl, —C(O)$R^6$, —CO$_2R^6$, —C(O)N($R^6$)$_2$, —OR$^6$, —S(O)$_eR^6$, —N ($R^6$)$_2$, —N($R^6$)COR$^6$, —CN, —SCN, Ay and 5- to 9-membered heteroaryl containing 1 or 2 heteroatoms selected from N, O and S;

and all other variables are as defined above.

Compounds of formula (I-C) can be prepared by reacting a compound of formula (I-A) with a compound of formula (XIII): $R^{16}$—$R^7$, wherein $R^{16}$ and $R^{17}$ are as defined above.

The reaction may be carried out in an inert solvent, in the presence of a palladium (0) catalyst and a base. The reaction may optionally be heated to a temperature of from about 65 to about 100° C. In one embodiment, the reaction is carried out by reacting equimolar amounts of a compound of formula (I-A) and the compound of formula (XIII). However, the reaction may also be performed in the presence of an excess of compound of the formula (XIII). The palladium catalyst is typically present in 1-20 mol % compared to the compound of formula (I-A). Examples of suitable palladium catalysts include but are not limited to tetrakis(triphenylphosphine) palladium (0), tris(dibenzylideneacetone)dipalladium (0), dichlorobis(triphenyl-phosphine)palladium (II), and palladium acetate (II) with triphenylphosphine. In one embodiment, the palladium catalyst is complexed with copper iodide, wherein the coper iodide is present in an amount of 200 mol % compared to the palladium catalyst. The base is typically present in a proportion equivalent to or greater than 400 mol % of the compound of formula (I-A). Suitable bases include but are not limited to potassium carbonate, potassium acetate, triethylamine, diethylamine, diisopropylamine, and cesium carbonate. Suitable solvents include but are not limited to dioxane, toluene, N,N-dimethylformamide, and tetrahydrofuran. Compounds of formula (XIII) may be obtained from commercial sources or prepared as discreet isolated compounds using methods known to one skilled in the art. See, S. Rosenblum, *Tetrahedron* 56:5735 (2000).

If desired a compound of formula (I-C) may be hydrogenated to provide an lkylene linker to —$R^{17}$.

In yet another example a compound of formula (I-A) may be converted to a compound of formula (I-D).

Compounds of formula (I-D) can be prepared by reacting a compound of formula (I-A) with a compound of formula (XIV). The reaction may be carried out in an inert solvent, in the presence of a palladium (0) catalyst and copper bromide. The reaction may optionally be heated to about 65-100° C. Typically, the reaction is performed by reacting equimolar amounts of a compound of formula (XIV) and the tributyltin compound of formula (XIV), but the reaction may also be performed in the presence of an excess of compound of the formula (XIV). The palladium catalyst is preferably present in 5-20 mol % compared to the compound of formula (I-A). Examples of suitable palladium catalysts include but are not limited to dichlorobis(triphenyl-phosphine)palladium (II) and palladium acetate (II) with triphenylphosphine, and tris (dibenzylideneacetone)dipalladium (0). The palladium catalyst is typically complexed with copper bromide. The copper bromide is preferably present in 200 mol % compared to the palladium catalyst. Suitable solvents include but are not limited to dioxane, N,N-dimethylformamide, and tetrahydrofuran. The compounds of formula (XIV) may be obtained from commercial sources or prepared as discreet isolated compounds using methods known to one skilled in the art. (Kukla, M. J. *Bioorg. Med. Chem. Let.* 2001, 11, 2235; Yamada, K. *J. Med. Chem.* 2001, 44, 3355).

A compound of formula (I-D) may be further converted to a compound of formula (I-E) by oxidation.

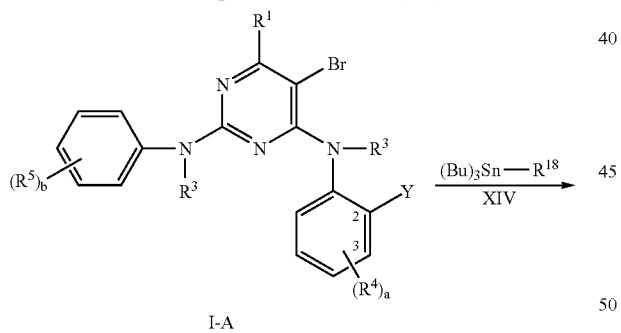

wherein $R^{18}$ is alkenyl, Ay or 5- to 9-membered heteroaryl containing 1 or 2 heteroatoms selected from N, O and S and all other variables are as defined above.

Conventional oxidizing agents and conditions may be employed. Examples of suitable oxidizing agents include but are not limited to mixtures of osmium tetroxide with sodium periodate, osmium tetroxide with N-methylmorpholine N-oxide, ozone with dimethyl sulfide, and potassium permanganate. The oxidation may be carried out in a suitable solvent, such as aqueous tetrahydrofuran, dichloromethane, ether, ethanol or the like. (See, Kasibhatla, S. R. *J. Med. Chem.* 2000, 43, 1508).

In yet another embodiment, a compound of formula (I-A) may be converted to a compound of formula (I-F), which may in turn be oxidized to a compound of formula (I-G).

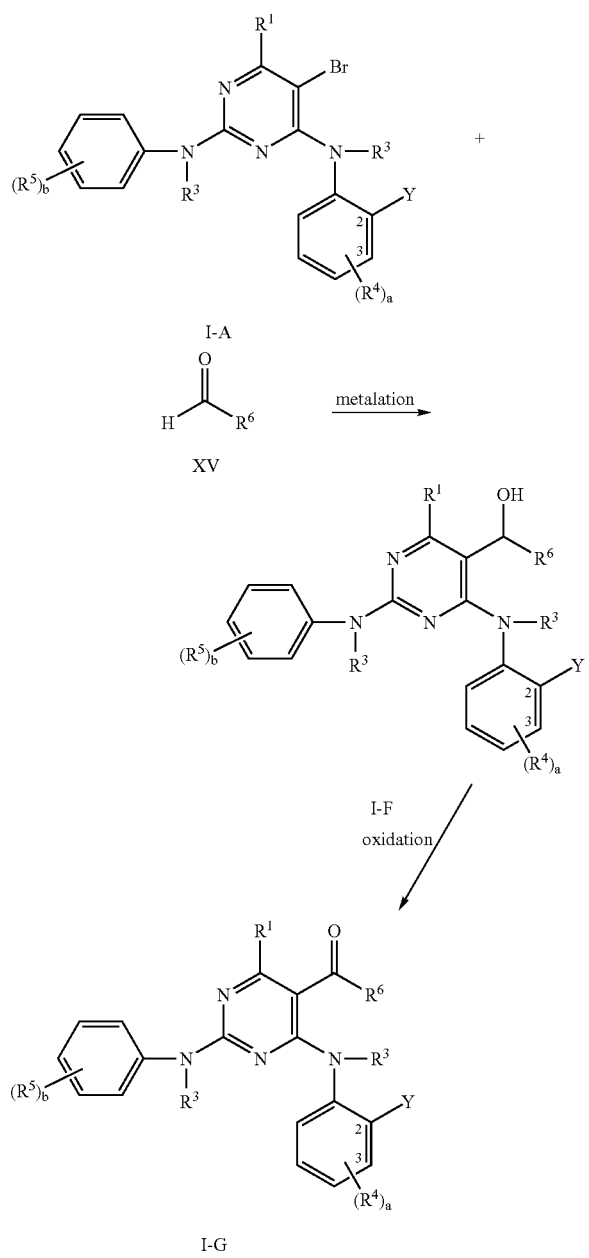

I-A

XV

I-F

I-G wherein R³ is other than H and all other variables are as defined above.

Compounds of formula (I-F) can be prepared by reacting a compound of formula (I-A) with a compound of formula (XV). The reaction may be carried out in an inert solvent, such as tetrahydrofuran, with an appropriate metalating agent such as lithium metal. The reaction may optionally be sonicated at room temperature. Typically, the reaction is performed by reacting equimolar amounts of the compound formula (I-A) with the aldehyde of formula (XV), but the reaction may also be performed in the presence of an excess of compound of the formula (XV). Aldehyde compounds of formula (XV) may be obtained from commercial sources or prepared as discreet isolated compounds using methods known to one skilled in the art. A compound of formula (I-F) may be converted to a compound of formula (I-G) by oxidation using conventional reagents and conditions. Suitable oxidizing agents include but are not limited to pyrimidinium chlorochromate, magnesium dioxide, and 2,3-dichloro-5,6-dicyano-1,4-benzoquinone and the like. Suitable solvents include dichloromethane, benzene, tetrahydrofuran, dioxane and the like.

A compound of formula (I-A) may also be converted to a compound of formula (I-H).

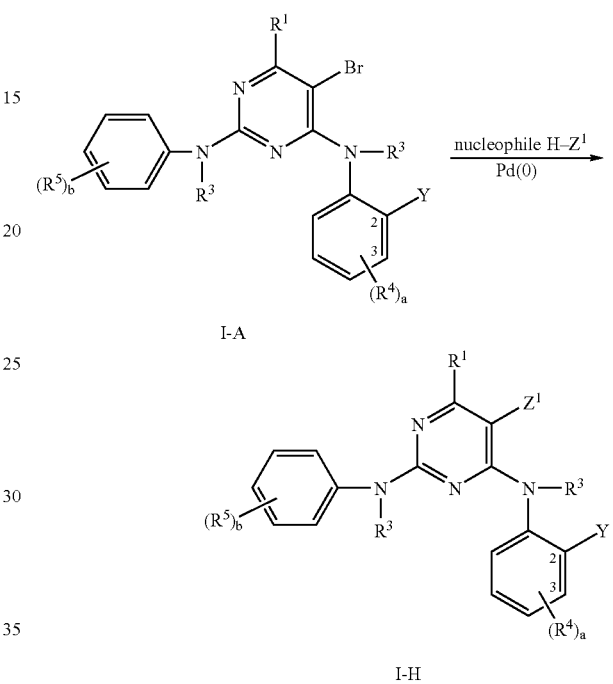

I-A

I-H wherein $Z^1$ is selected from the group consisting of —OR⁶, —OAy, —OR⁷-Ay, —(R⁷)$_g$—N(R⁶)$_2$, and —(R⁷)$_g$—N(R⁶)COR⁶, and all other variables are as defined above.

The reaction may be carried out in an inert solvent, in the presence of a palladium(0) catalyst and a base. The reaction may optionally be heated to a temperature of from about 23 to about 100° C. Typically, the reaction is performed by reacting equimolar amounts of a compound of formula (I-A) and the nucleophile but may also be performed in the presence of an excess of the nucloephile. The palladium catalyst is typically present in an amount of about 1 to about 5 mol % compared to the compound of formula (I-A). Examples of suitable palladium catalysts include but are not limited to tris(dibenzylideneacetone)dipalladium(0) coupled with Xantphos, palladium acetate (II) coupled with Xantphos, palladium acetate (II) coupled with 2-N,N-dimethylamino-2'-diphenylphosphino-biphenyl, 2-(di-tert-butylphosphino)-biphenyl, 1-(2-Di-tert-butylphosphinophenyl)-2-isopropyl-naphthalene and the like. Suitable bases include but are not limited to cesium carbonate, potassium tert-butoxide, sodium tert-butoxide, potassium carbonate and the like. Suitable solvents for this reaction include but are not limited to toluene, tetrahydrofuran, 1,4-dioxane, and the like. The nucleophiles may be obtained from commercial sources or prepared as discreet isolated compounds using methods known to one skilled in the art. (See, Buchwald, S. L. *J. Am. Chem. Soc.* 2001, 123, 10770; Buchwald, *Org. Letters.* 2000, 8, 1101; and Buchwald, *J. Org. Chem.* 1999, 64, 6019).

As will be apparent to those skilled in the art, a compound of formula (I-H) wherein $Z^1$ is O-benzyl may be further converted to a compound of formula (I-H) wherein $Z^1$ is —OH, by hydrogenolysis using conventional techniques. Suitable catalysts for the hydrogenolysis reaction include but are not limited to 5-15% palladium on carbon, palladium on barium sulfate, platinum and nickel. Suitable solvents include but are not limited to ethyl acetate, tetrahydrofuran, ethanol and methanol. (See, Goswami, A. *Tetrahedron Asymmetry* 2001, 12, 3343).

A compound of formula (I-A) may also be converted to a compound of formula (I-K).

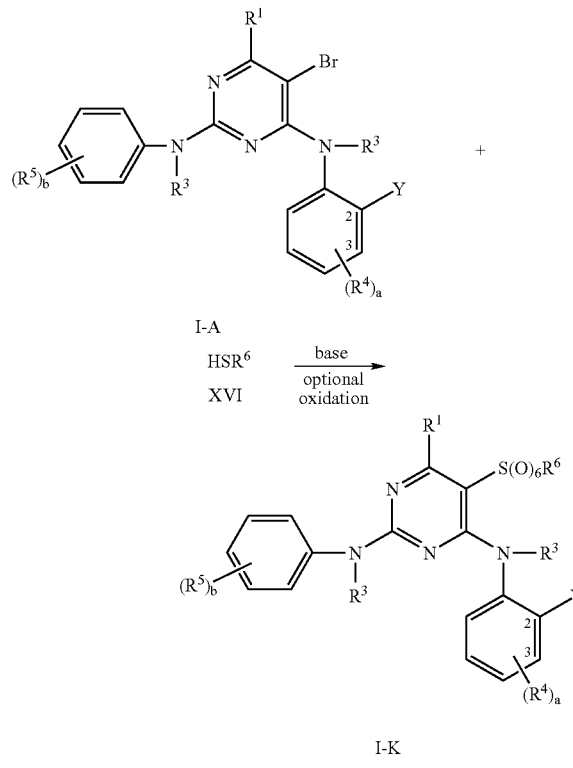

wherein all variables are as defined above.

Compounds of formula (I-K) can be prepared by reacting a compound of formula (I-A) with a compound of formula (XVI). The reaction may be carried out in an inert solvent, in the presence of a base. The reaction may be optionally heated to a temperature of from about 23 to about 150° C. Typically, the reaction is preformed by reacting equimolar amounts of the thio compound of formula (XVI) with the compound of formula (I-A), but may also be performed in the presence of an excess of compound of the formula (XVI). The base is typically present in an amount of about 10 to about 30 mol % compared to the compound of formula (I-A). Examples of suitable bases include but are not limited to sodium hydride, potassium hydroxide, sodium methoxide, potassium carbonate and the like. Suitable solvents include but are not limited to dimethylformamide, pyridine, methanol, ethanol, and hexamethylphosphoric acid triamide. Optionally the reaction may be catalyzed with copper oxide (I). Thio compounds of formula (XVI) may be obtained from commercial sources or prepared as discreet isolated compounds using methods known to those skilled in the art. (See, Ng, Dennis, K. P. *Tetraltderon*. 2000, 56, 3881).

Optionally, the thiol compounds of formula (I-K) may be subjected to an oxidation procedure to prepare the sulfonyl or sulfinyl compounds of formula (I-K). Typically the oxidation reaction is carried out by subjecting the thiol compound of formula (I-K) to an oxidizing agent in a suitable solvent. Suitable oxidizing agents include but are not limited to 3-chloroperoxybenzoic acid, oxone, hydrogen peroxide, potassium permanganate, and the like. Suitable solvents include but are not limited to dichlormethane, chloroform, carbontetrachloride, aqueous acidic acid. (See, Cushman, M. *J. Med. Chem.* 2001, 44, 3915).

A compound of formula (I-A) may also be converted to a compound of formula (I-L) or a compound of formula (I-M) using conventional metallation techniques.

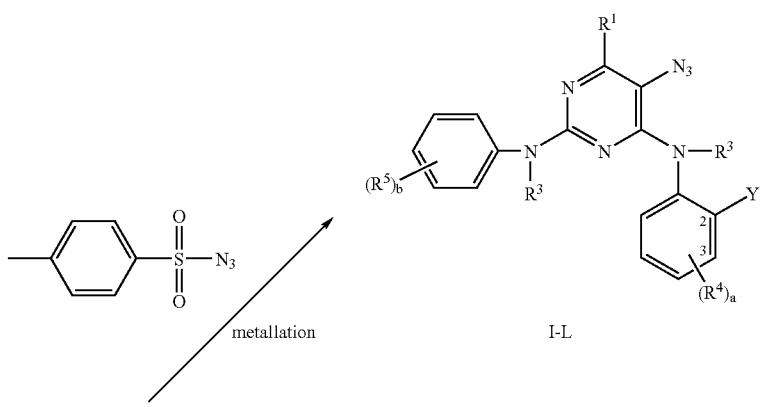

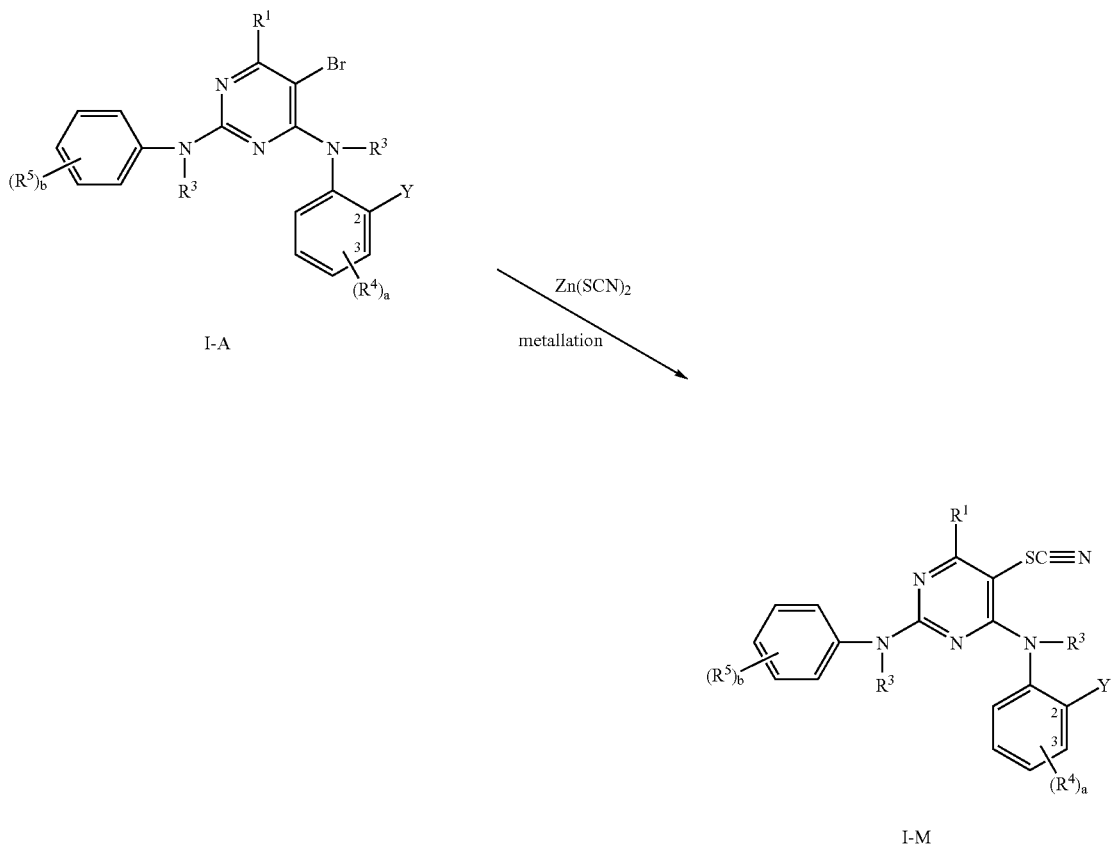

wherein all variables are defined as above with the proviso that when $R^3$ is H, Fe and $R^5$ are not halo.

Compounds of formula (I-L) or (I-M) can be prepared by treating a compound of formula (I-A) with a lithium metal followed by either the azide compound or the thiocyanate compound together with N-chlorosuccinimide, respectively. The reaction maybe carried out in an inert solvent. Typically, the reaction is cooled to a temperature of between about −78° and about 0° C. The reaction is conveniently reacting equimolar amounts of the compound formula (I-A) with the azide or thiocyanate and N-chlorosuccinimide, but the reaction may also be performed in the presence of an excess of the azide or thiocyanate. Suitable lithium metal reagents include but are not limited to, n-butyl-lithium and tert-butyl-lithium. Suitable solvents include but are not limited to tetrahydrofuran, ether, pentane and hexane. (See, Creary, X. *J, Org. Chem.* 1999, 64, 5634 and Takagi, K. *J. Org. Chem.* 1995, 60, 6552).

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I) and solid-support-bound versions thereof. Radiolabeled compounds of formula (I) and biotinylated compounds of formula (I) can be prepared using conventional techniques.

For example, radiolabeled compounds of formula (I) can be prepared by reacting the compound of formula (I) with tritium gas in the presence of an appropriate catalyst to produce radiolabeled compounds of formula (I).

In one embodiment, the compounds of formula (I) are tritiated.

The radiolabeled compounds of formula (I) and biotinylated compounds of formula (I) are useful in assays for the identification of compounds which inhibit PLK, for the identification of compounds for the treatment of a condition mediated by PLK, for the treatment of susceptible neoplasms, for the treatment of conditions characterized by inappropriate proliferation, for the inhibition of proliferation of a cell and for the inhitibion of mitosis in a cell. Accordingly, the present invention provides an assay method for identifying such compounds, which method comprises the step of specifically binding the radiolabeled compound of formula (I) or the biotinylated compound of formula (I) to the target protein or cellular homogenates. More specifically, suitable assay methods will include competition binding assays. The radiolabeled compounds of formula (I) and biotinylated compounds of formula (I) and solid-support-bound verstions thereof, can be employed in assays according to the methods conventional in the art.

The following examples are intended for illustration only and are not intended to limit the scope of the invention in any way, the invention being defined by the claims which follow.

Reagents are commercially available or are prepared according to procedures in the literature.

EXAMPLE 1

2-({5-nitro-2-[(3,4,5-trimethoxyphenyl)amino]pyrimidin-4-yl}amino)benzoic acid hydrochloride

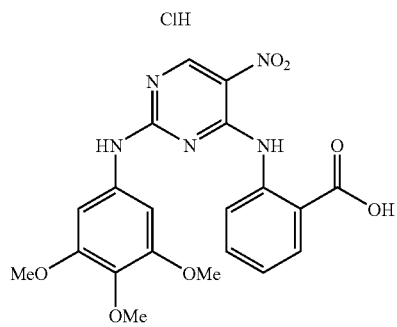

To a mixture of 2-[(2-chloro-5-nitropyrimidin-4-yl)amino]benzoic acid (52 mg, 0.178 mmol) and 3,4,5-trimethoxyaniline (34 mg, 0.185 mmol) in 2-propanol (2 mL) was added 1N HCl in diethyl ether (50 uL, 0.05 mmol). The reaction mixture was heated at 90° C. for 30 hours. After the reaction was cooled to room temperature the mixture was filtered, and the solid was washed with 2-propanol, hexane, and ethyl acetate. The solid was then dried under vacuum to give 2-({5-nitro-2-[(3,4,5-trimethoxyphenyl)-amino]pyrimidin-4-yl}amino)benzoic acid hydrochloride (53 mg, 63%) as a dirty orange solid. $^1$H NMR (DMSO-$d_6$/$D_2O$): δ 9.14 (s, 1H), 8.47 (m, 1 H), 8.02 (d, 1 H), 7.46 (m, 1 H), 7.26 (t, 1 H), 6.95 (s, 2 H), 3.69 (s, 3 H), 3.63 (s, 6 H); MS m/z 441 (M+1).

EXAMPLE 2

2-2-[(2-chloro-5-nitropyrimidin-4-yl)amino]benzoic acid

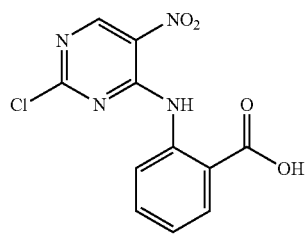

To a cooled (−78° C.) solution of 2,4-dichloro-5-nitropyrimidine (0.53 g, 2.75 mmol) in THF (2 mL) was added a solution of anthranilic acid (0.37 g, 2.50 mmol) and N,N-diisopropylethylamine (0.5 mL, 3.0 mmol) in THF (2.0 mL). The reaction was stirred for 2.0 hours. The reaction was then poured onto ice and allowed to warm to room temperature then was filtered. The isolated solid was dried under vacuum, then recrystallized from hot ethyl acetate and cold hexane to give 2-[(2-chloro-5-nitropyrimidin-4-yl)amino]benzoic acid (307 mg, 42%) as a yellow solid. $^1$H NMR (DMSO-$d_6$/$D_2O$): δ 9.20 (s, 1H), 8.36 (d, 1H), 8.07 (d, 1 H), 7.70 (t, 1 H), 7.37 (t, 1 H). MS m/z 294 (M+1).

EXAMPLE 3

2-({5-nitro-2-[(3,4,5-trimethoxyphenyl)amino]pyrimidin-4-yl}amino)benzamide hydrochloride

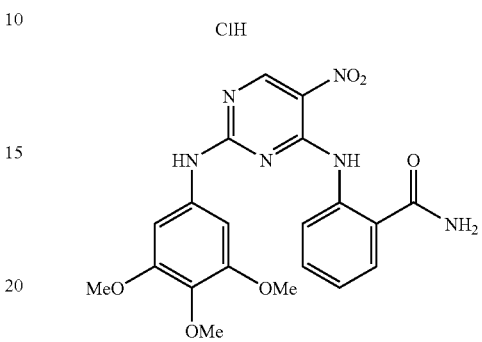

To a mixture of 2-[(2-chloro-5-nitropyrimidin-4-yl)amino]benzamide (52 mg, 0.178 mmol) and 3,4,5-trimethoxyaniline (34 mg, 0.185 mmol) in 2-propanol (2 mL) was added 1N HCl in diethyl ether (50 uL, 0.05 mmol). The reaction mixture was heated at 90° C. for approx. 18 hours. After the reaction was cooled to room temperature cold diethyl ether was added to precipitate out the product. The precipitate was filtered and washed with cold diethyl ether, then dried under vacuum to give 2-({5-nitro-2-[(3,4,5-trimethoxyphenyl)amino]pyrimidin-4-yl}amino)benzamide hydrochloride (30 mg, 35%) as a dark brown solid. $^1$H NMR (DMSO-$d_6$/$D_2O$): δ 9.07 (s, 1H), 8.26 (m, 1 H), 7.69 (d, 1 H), 7.34 (t, 1 H), 7.19 (t, 1 H), 6.92 (s, 2 H), 3.77 (s, 3 H), 3.59 (s, 6 H). MS m/z 440 (M+1).

EXAMPLE 4

2-[(2-chloro-5-nitropyrimidin-4-yl)amino]benzamide

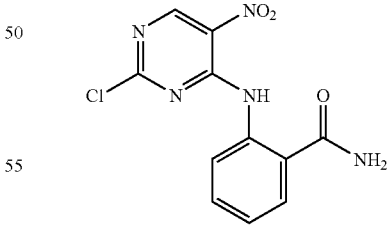

In a similar manner as described in Example 2 from 2-aminobenzamide (0.34 g, 2.50 mmol) was obtained 2-[(2-chloro-5-nitropyrimidin-4-yl)amino]benzamide (437 mg, 60%) as a yellow solid. $^1$H NMR (DMSO-$d_6$/$D_2O$): δ 9.17(s, 1H), 8.24 (d, 1H), 7.80 (d, 1 H), 7.60 (t, 1 H), 7.33 (t, 1 H). MS m/z 293 (M+1).

EXAMPLE 5

N-(tert-butyl)-2-({5-nitro-2-[(3,4,5-trimethoxyphenyl)amino]pyrimidin-4-yl}amino)benzamide hydrochloride

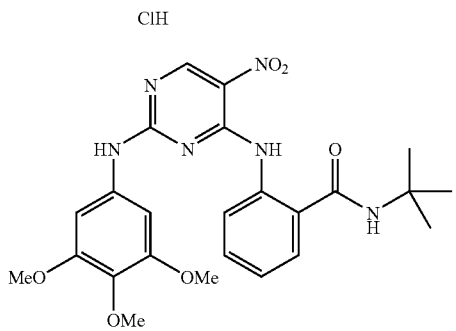

In a similar manner as described in Example 3 from N-(tert-butyl)-2-[(2-chloro-5-nitropyrimidin-4-yl)amino]benzamide (62 mg, 0.178 mmol) was obtained N-(tert-butyl)-2-({5-nitro-2-[(3,4,5-trimethoxyphenyl)amino]pyrimidin-4-yl}amino)-benzamide hydrochloride (35 mg, 37%) as a tan solid. $^1$H NMR (DMSO-$d_6$/$D_2O$): δ 9.07 (s, 1H), 8.09 (d, 1H), 7.52 (d, 1 H), 7.33 (t, 1 H), 7.21 (t, 1 H), 6.90 (s, 2 H), 3.64 (s, 3 H), 3.59 (s, 6 H), 1.32 (s, 9 H). MS m/z 496 (M+1).

EXAMPLE 6

N-(tert-Butyl)-2-[(2-chloro-5-nitropyrimidin-4-yl)amino]benzamide

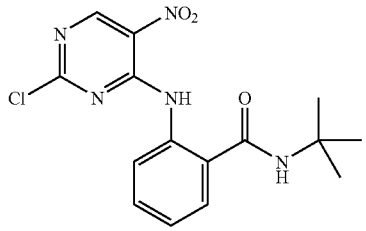

In a similar manner as described in Example 2 from 2-amino-N-(tert-butyl)benzamide (0.48 g, 2.50 mmol) was obtained: N-(tert-butyl)-2-[(2-chloro-5-nitropyrimidin-4-yl)amino]benzamide (630 mg, 72%) as a yellow solid. $^1$H NMR (DMSO-$d_6$/$D_2O$): δ 9.13 (s, 1H), 8.02 (d, 1 H), 7.60 (d, 1 H), 7.52 (t, 1 H), 7.30 (t, 1 H), 1.33 (s, 9 H). MS m/z 349 (M+1).

EXAMPLE 7

N-[4-({4-[(2-benzoylphenyl)amino]-5-nitropyrimidin-2-yl}amino)phenyl]acetamide hydrochloride

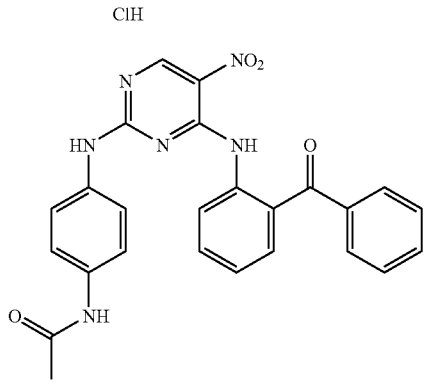

To a mixture of {2-[(2-chloro-5-nitropyrimidin-4-yl)amino]phenyl}(phenyl)-methanone (63 mg, 0.178 mmol) and N-(4-aminophenyl)acetamide (28 mg, 0.185 mmol) in 2-propanol (2 mL) was added 1N HCl in diethyl ether (50 uL, 0.05 mmol). The reaction mixture was heated at 90° C. for approx. 18 hours. After the reaction was cooled to room temperature cold diethyl ether was added to precipitate out the product. The precipitate was filtered and washed with cold diethyl ether, then dried under vacuum to give N-[4-({4-[(2-benzoylphenyl)amino]-5-nitropyrimidin-2-yl}amino)phenyl]acetamide hydrochloride (12 mg, 13%) as a tan solid. $^1$H NMR (DMSO-$d_6$/$D_2O$): δ 8.98 (s, 1H), 8.12 (m, 1H), 7.69-7.43 (m, 12 H), 2.05 (s, 3 H). MS m/z 468 (M+1).

EXAMPLE 8

{2-[(2-chloro-5-nitropyrimidin-4-yl)amino]phenyl}(phenyl)methanone

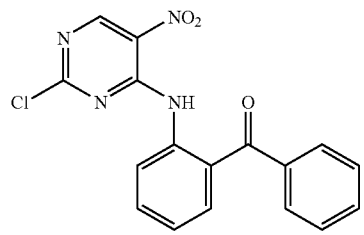

To a cooled (−78° C.) solution of 2,4-dichloro-5-nitropyrimidine (0.53 g, 2.75 mmol) in THF (3 mL) was added a solution of (2-aminophenyl)(phenyl)methanone (0.30 g, 1.55 mmol) and N,N-diisopropylethylamine (0.5 mL, 3.0 mmol) in THF (2.0 mL). The reaction was stirred for 2.0 hours. The reaction was then poured onto ice and allowed to warm to room temperature then was filtered, washing the solid with water. The isolated solid was dried under vacuum to give {2-[(2-chloro-5-nitropyrimidin-4-yl)amino]phenyl}(phenyl)methanone (496 mg, 90%) as a yellow solid. $^1$H NMR (DMSO-$d_6$/$D_2O$): δ 9.06 (s, 1H), 7.96 (d, 1H), 7.76-7.44 (m, 8 H). MS m/z 354 (M+1).

EXAMPLE 9

8-({5-nitro-2-[(3,4,5-trimethoxyphenyl)amino]pyrimidin-4-yl}amino)-3,4-dihydronaphthalen-1(2H)-one hydrochloride

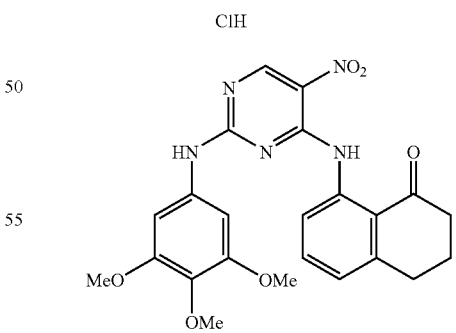

In a similar manner as described in Example 3 from 8-[(2-chloro-5-nitropyrimidin-4-yl)amino]-3,4-dihydronaphthalen-1(2H)-one (56 mg, 0.178 mmol) was obtained 8-({5-nitro-2-[(3,4,5-trimethoxyphenyl)amino]pyrimidin-4-yl}amino)-3,4-dihydronaphthalen-1(2H)-one hydrochloride (75 mg, 85%) as a maroon solid. $^1$H NMR (DMSO-$d_6$/$D_2O$): δ 9.09 (s, 1H), 8.37 (m, 1H), 7.32 (m, 1 H), 7.09 (d, 1 H) 6.91

(s, 2 H), 3.66 (s, 3 H), 3.62 (s, 6 H), 2.94 (t, 2 H), 2.65 (t, 2 H), 1.99 (m, 2 H). MS m/z 465 (M+1).

EXAMPLE 10

8-[(2-chloro-5-nitropyrimidin-4-yl)amino]-3,4-dihydronaphthalen-1(2H)-one

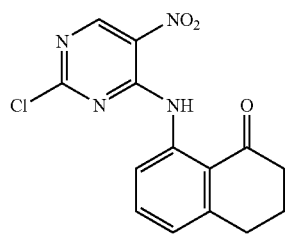

In a similar manner as described in Example 8 from 8-amino-3,4-dihydronaphthalen-1(2H)-one (0.187 g, 1.16 mmol) was obtained 8-[(2-chloro-5-nitropyrimidin-4-yl)amino]-3,4-dihydronaphthalen-[(2H)-one (313 mg, 85%) as a light tan solid. $^1$H NMR (DMSO-d$_6$/D$_2$O): δ 9.21 (s, 1H), 8.32 (d, 1H), 7.62 (t, 1 H), 7.24 (d, 1 H) 3.02 (t, 2 H), 2.72 (t, 2 H), 2.06 (m, 2 H). MS m/z 318 (M+1).

EXAMPLE 11

1-[2-({5-bromo-2-[(3,4,5-trimethoxyphenyl)amino]pyrimidin-4-yl}amino)phenylethanone hydrochloride

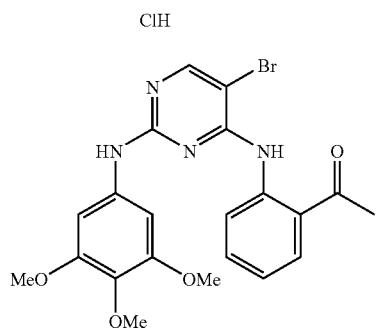

In a similar manner as described in Example 1 from 1-{2-[(5-bromo-2-chloropyrimidin-4-yl)amino]phenyl}ethanone (58 mg, 0.178 mmol) was obtained 1-[2-({5-bromo-2-[(3,4,5-trimethoxyphenyl)amino]pyrimidin-4-yl}amino)phenyl]ethanone hydrochloride (68 mg, 75%) as an off white solid. $^1$H NMR (DMSO-d$_6$/D$_2$O): δ 8.75 (d, 1H), 8.30 (s, 1H), 8.06 (d, 1H), 7.50 (t, 1H), 7.20 (t, 1H), 6.92 (s, 2H), 3.67 (s, 6H), 3.65 (s, 3H), 2.65 (s, 3H). MS m/z 473 (M+1).

EXAMPLE 12

1-{2-[(5-bromo-2-chloropyrimidin-4-yl)amino]phenyl}ethanone

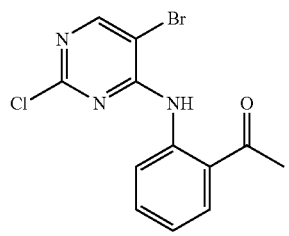

A mixture of 5-bromo-2,4-dichloropyrimidine (1.25 g, 5.5 mmol) and 1-(2-aminophenyl)ethanone (675 mg, 5.0 mmol) with sodium bicarbonate (1.26 g, 15.0 mmol) in 4:1 EtOH/THF (7.5 mL) was stirred at 80° C. for 14 hours. The reaction was cooled to room temperature and the resulting mixture was filtered, washing the solid with cold EtOH. The collected solid was stirred in hot water, filtered, and the resulting solid washed with cold EtOH. The solid was then dried under vacuum to give 1-{2-[(5-bromo-2-chloropyrimidin-4-yl)amino]phenyl}ethanone (761 mg, 47%) as a yellow solid. $^1$H NMR (DMSO-d$_6$): δ 11.91 (s, 1H), 8.60-8.64 (m, 2H), 8.15 (d, 1 H), 7.74 (t, 1 H), 7.31 (t, 1 H), 2.72 (s, 3 H). MS m/z 326 (M+1).

EXAMPLE 13

2-[(2-{[4-(acetylamino)phenyl]amino}-5-nitropyrimidin-4-yl)amino]-N-methylbenzamide hydrochloride

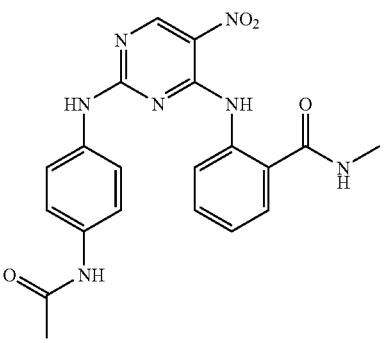

To a mixture of 2-[(2-chloro-5-nitropyrimidin-4-yl)amino]-N-methylbenzamide (54 mg, 0.178 mmol) and N-(4-aminophenyl)acetamide (28 mg, 0.185 mmol) in 2-propanol (2 mL) was added 1N HCl in diethyl ether (50 uL, 0.05 mmol). The reaction mixture was heated at 90° C. for 30 hours. After the reaction was cooled to room temperature the mixture was filtered, and the solid was washed with 2-propanol, hexane, and ethyl acetate. The solid was then dried under vacuum to give 2-[(2-{[4-(acetylamino)phenyl]amino}-5-nitropyrimidin-4-yl)amino]-N-methylbenzamide hydrochloride (58 mg, 71%) as a yellow tan solid. $^1$H NMR (DMSO-d$_6$/D$_2$O): δ 9.05 (s, 1H), 8.20 (m, 1H), 7.59 (d, 1 H), 7.40-7.50 (m, 5 H), 7.24 (t, 1 H), 2.76 (s, 3 H), 2.02 (s, 3H). MS m/z 421 (M+1).

EXAMPLE 14

2-[(2-chloro-5-nitropyrimidin-4-yl)amino]-N-methylbenzamide

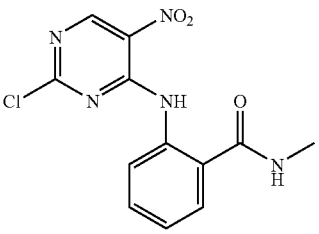

In a similar manner as described in Example 2 from 2-amino-N-methylbenzamide (0.37 g, 2.50 mmol) was obtained 2-[(2-chloro-5-nitropyrimidin-4-yl)amino]-N-methylbenzamide (685 mg, 89%) as a yellow solid. $^1$H NMR (DMSO-d$_6$/D$_2$O): δ 9.13 (s, 1 H), 8.12 (d, 1 H), 7.66 (d, 1 H), 7.55 (t, 1 H), 7.30 (t, 1 H), 2.77 (sr 3 H). MS m/z 307 (M+1).

EXAMPLE 15

N⁴-(1H-indol-4-yl)-5-nitro-N²-(3,4,5-trimethoxyphenyl)pyrimidine-2,4-diamine hydrochloride

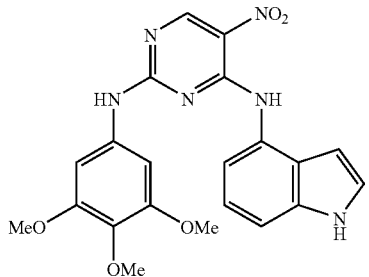

In a similar manner as described in Example 1 from N-(2-chloro-5-nitropyrimidin-4-yl)-1H-indol-4-amine (51 mg, 0.178 mmol) was obtained N⁴-(1H-indol-4-yl)-5-nitro-N²-(3,4,5-trimethoxyphenyl)pyrimidine-2,4-diamine hydrochloride (72 mg, 86%) as a brown solid. ¹H NMR (DMSO-$d_6$/$D_2O$): δ 9.10 (s, 1 H), 7.67 (m, 1 H), 7.28-7.34 (m, 2 H), 7.03 (t, 1 H), 6.90 (s, 3 H), 3.62 (s, 3 H), 3.49 (s, 6 H). MS m/z 436 (M+1).

EXAMPLE 16

N-(2-chloro-5-nitropyrimidin-4-yl)-1H-indol-4-amine

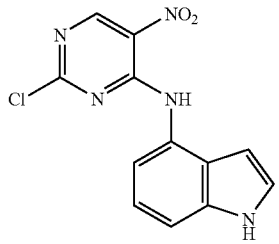

In a similar manner as described in Example 2 from 1H-indol-4-amine (0.33 g, 2.50 mmol) was obtained A*(2-chloro-5-nitropyrimidin-4-yl)-1H/indol-4-amine (556 mg, 77%) as a maroon solid. ¹H NMR (DMSO-$d_6$): δ 11.17 (s, 1 H), 10.45 (s, 1 H), 9.14 (s, 1 H), 7.37-7.42 (m, 3 H), 7.16 (t, 1 H), 6.40 (s, 1 H). MS m/z 289 (M+1).

EXAMPLE 17

Methyl 2-({5-nitro-2-[(3,4,5-trimethoxyphenyl)amino]pyrimidin-4-yl}amino)benzoate hydrochloride

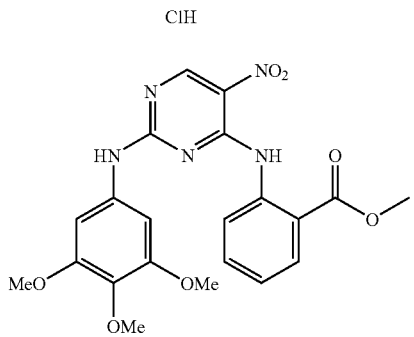

In a similar manner as described in Example 1 from methyl 2-[(2-chloro-5-nitropyrimidin-4-yl)amino]benzoate (55 mg, 0.178 mmol) was obtained methyl 2-({5-nitro-2-[(3,4,5-trimethoxyphenyl)amino]pyrimidin-4-yl}amino)benzoate hydrochloride (60 mg, 69%) as a tan solid. ¹H NMR (DMSO-$d_6$/$D_2O$): δ 9.10 (s, 1 H), 8.37 (m, 1 H), 7.96 (d, 1 H), 7.46 (t, 1 H), 7.26 (t, 1 H), 6.90 (s, 2 H), 3.87 (s, 3 H), 3.65 (s, 3 H), 3.58 (s, 6 H)3+. MS m/z 455 (M+1).

EXAMPLE 18

Methyl 2-[(2-chloro-5-nitropyrimidin-4-yl)amino]benzoate

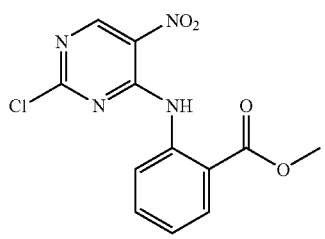

In a similar manner as described in Example 2 from methyl 2-aminobenzoate (0.37 g, 2.50 mmol) was obtained Methyl 2-[(2-chloro-5-nitropyrimidin-4-yl)amino]benzoate (486 mg, 63%) as a yellow solid. ¹H NMR (DMSO-$d_6$): δ 9.17 (s, 1 H), 8.19 (d, 1 H), 8.00 (d, 1 H), 7.69 (t, 1 H), 7.37 (t, 1 H), 3.87 (s, 3 H). MS m/z 308 (M+1).

EXAMPLE 19

N⁴-(2,3-dihydro-1,4-benzodioxin-5-yl)-5-nitro-N²-(3,4,5-trimethoxyphenyl)pyrimidine-2,4-diamine hydrochloride

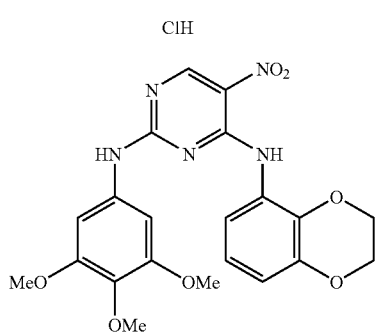

In a similar manner as described in Example 3 from 2-chloro-N-(2,3-dihydro-1,4-benzodioxin-5-yl)-5-nitropyrimidin-4-amine (55 mg, 0.178 mmol) was obtained N⁴-(2,3-dihydro-1,4-benzodioxin-5-yl)-5-nitro-N²-(3,4,5-trimethoxyphenyl)pyrimidine-2,4-diamine hydrochloride (60 mg, 69%) as a tan solid. ¹H NMR (DMSO-$d_6$/$D_2O$): δ 9.07 (s, 1 H), 7.80 (m, 1 H), 6.92 (s, 2 H), 6.67-6.71 (m, 2 H), 4.31-4.33 (m, 2 H), 4.22-4.26 (m, 2 H), 3.75 (s, 3 H), 3.64 (s, 6 H). MS m/z 455 (M+1).

EXAMPLE 20

2-chloro-N-(2,3-dihydro-1,4-benzodioxin-5-yl)-5-nitropyrimidin-4-amine

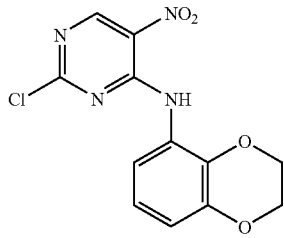

In a similar manner as described in Example 8 from 2,3-dihydro-1,4-benzodioxin-5-amine (187 mg, 1.87 mmol) was obtained 2-chloro-N-(2,3-dihydro-1,4-benzodioxin-5-yl)-5-nitropyrimidin-4-amine (209 mg, 68%) as a yellow solid. $^1$H NMR (DMSO-$d_6$): δ 9.13 (s, 1 H), 7.57 (d, 1 H), 6.77-6.92 (m, 2 H), 4.26-4.38 (m, 4 H). MS m/z 308 (M+1).

EXAMPLE 21

Cyclohexyl 2-[(2-{[4-(acetylamino)phenyl]amino}-5-nitropyrimidin-4-yl)amino]benzoate hydrochloride

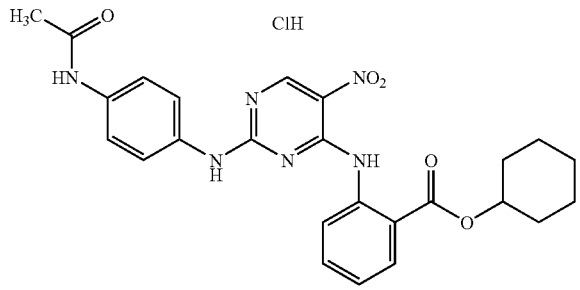

In a similar manner as described in Example 1 from cyclohexyl 2-[(2-chloro-5-nitropyrimidin-4-yl)amino]benzoate (67 mg, 0.178 mmol) and N-(4-aminophenyl)acetamide (28 mg, 0.185 mmol) was obtained cyclohexyl 2-[(2-{[4-(acetylamino)phenyl]amino}-5-nitropyrimidin-4-yl)amino]benzoate hydrochloride (13 mg, 14%) as a yellow solid. $^1$H NMR (DMSO-$d_6$/D$_2$O): δ 9.07 (s, 1H), 8.20 (m, 1 H), 7.98 (d, 1 H), 7.57 (t, 1 H), 7.30-7.46 (m, 5 H), 4.92 (m, 1 H), 2.01 (s, 3 H), 1.20-1.80 (m, 10 H). MS m/z 490 (M+1).

EXAMPLE 22

5-Hydroxy-2-({5-nitro-2-[(3,4,5-trimethoxyphenyl)amino]pyrimidin-4-yl}amino)benzoic acid hydrochloride

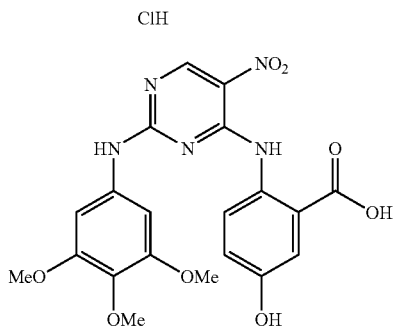

In a similar manner as described in Example 1 from 2-[(2-chloro-5-nitropyrimidin-4-yl)amino]-5-hydroxybenzoic acid (55 mg, 0.178 mmol) was obtained 5-hydroxy-2-({5-nitro-2-[(3,4,5-trimethoxyphenyl)amino]pyrimidin-4-yl}amino)benzoic acid hydrochloride (21 mg, 24%) as a tan solid. $^1$H NMR (DMSO-$d_6$/D$_2$O): δ 9.05 (s, 1H), 8.08 (m, 1H), 7.34 (d, 1 H), 6.85-6.91 (m, 3 H), 3.65 (s, 3 H), 3.59 (s, 6 H). MS m/z 457 (M+1).

EXAMPLE 23

2-[(2-{[4-(Acetylamino)phenyl]amino}-5-nitropyrimidin-4-yl)amino]benzoic acid hydrochloride

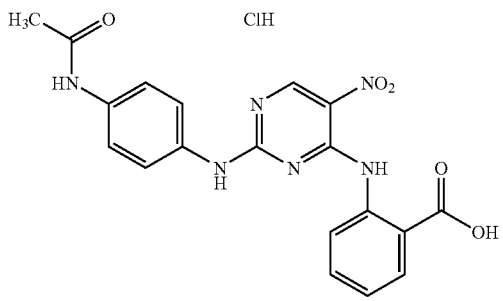

In a similar manner as described in Example 1 from 2-((2-chloro-5-nitropyrimidin-4-yl)amino]benzoic acid (52 mg, 0.178 mmol) and N-(4-aminophenyl)acetamide (28 mg, 0.185 mmol) was obtained 2-[(2-{[4-(acetylamino)phenyl]amino}-5-nitropyrimidin-4-yl)amino]benzoic acid hydrochloride (7 mg, 8%) as a tan solid. $^1$H NMR (DMSO-$d_6$/D$_2$O): δ 9.08 (s, 1H), 8.39 (m, 1H), 7.83 (d, 1 H), 7.42-7.55 (m, 5 H), 7.27 (t, 1 H), 2.02 (s, 3 H). MS m/z 408 (M+1).

EXAMPLE 24

N-[4-({4-[(2-Acetylphenyl)amino]-5-bromopyrimidin-2-yl}amino)phenyl]acetamide hydrochloride

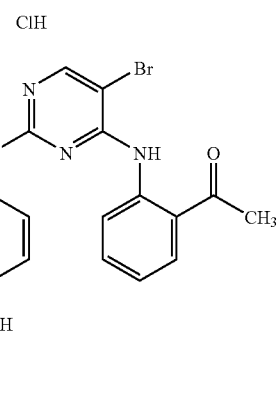

In a similar manner as described in Example 1 from 1-{2-[(5-bromo-2-chloropyrimidin-4-yl)amino]phenyl}ethanone (58 mg, 0.178 mmol) and N-(4-aminophenyl)acetamide (28 mg, 0.185 mmol) was obtained N-[4-({4-[(2-acetylphenyl)amino]-5-bromopyrimidin-2-yl}amino)phenyl]acetamide hydrochloride (72 mg, 85%) as a light tan solid. $^1$H NMR (DMSO-$d_6$/D$_2$O): δ 8.72 (d, 1H), 8.27 (s, 1H), 8.06 (dd, 1 H), 7.53 (m, 1 H), 7.46 (s, 4 H), 7.20 (m, 1 H), 2.65 (s, 3 H), 2.02 (s, 3 H). MS m/z 440 (M+1).

EXAMPLE 25

N-[4-({5-Bromo-4-[(2-morpholin-4-ylphenyl)amino]pyrimidin-2-yl}amino)phenyl]acetamide hydrochloride

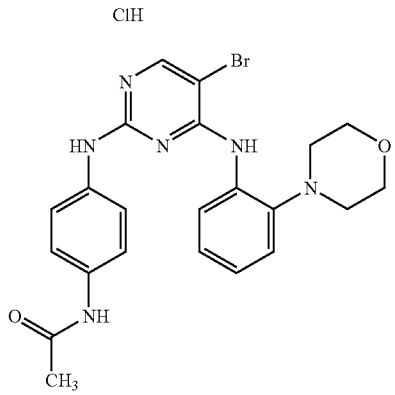

In a similar manner as described in Example 1 from 5-bromo-2-chloro-N-(2-morpholin-4-ylphenyl)pyrimidin-4-amine (66 mg, 0.178 mmol) and N-(4-aminophenyl)acetamide (28 mg, 0.185 mmol) was obtained N-[4-({5-bromo-4-[(2-morpholin-4-ylphenyl)amino]pyrimidin-2-yl}amino)phenyl]acetamide hydrochloride (80 mg, 87%) as a blue grey solid. $^1$H NMR (DMSO-$d_6$/$D_2O$): δ 8.25 (s, 1H), 7.40-7.51 (m, 5H), 7.29 (m, 1 H), 7.1 (m, 2 H), 3.78 (t, 4 H), 2.82 (t, 4 H), 2.03 (s, 3 H). MS m/z 483 (M+1).

EXAMPLE 26

5-[(5-Bromo-4-{[2-(methylthio)phenyl]amino]pyrimidin-2-yl)amino]-1,3-dihydro-2H-benzimidazol-2-one hydrochloride

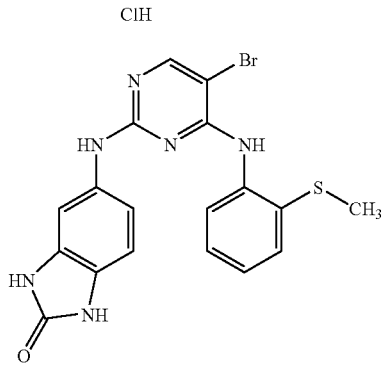

In a similar manner as described in Example 1 from 5-bromo-2-chloro-N-[2-(methylthio)phenyl]pyrimidin-+amine (59 mg, 0.178 mmol) and 5-amino-1,3-dihydro-2H-benzimidazol-2-one (28 mg, 0.185 mmol) was obtained 5-[(5-bromo-4-{[2-(methylthio)phenyl]amino}pyrimidin-2-yl)amino]-1,3-dihydro-2H-benzimidazol-2-one hydrochloride (7 mg, 8%) as an off-white solid. $^1$H NMR (DMSO-$d_6$/$D_2O$): δ 8.20 (s, 1H), 7.82 (m, 1H), 7.47 (m, 1 H), 7.23 (m, 1 H), 6.92-7.05 (m, 3 H), 6.74 (d, 1 H), 2.40 (s, 3 H). MS m/z 443 (M+1).

EXAMPLE 27

5-Bromo-$N^4$-(2-morpholin-4-ylphenyl)-$N^2$-(3,4,5-trimethoxyphenyl)-pyrimidine-2,4-diamine hydrochloride

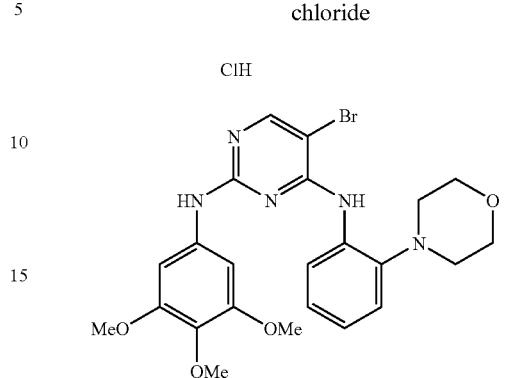

In a similar manner as described in Example 1 from 5-bromo-2-chloro-*(2-morpholin-4-ylphenyl)pyrimidin-4-amine (66 mg, 0.178 mmol) was obtained 5-bromo-$N^4$-(2-morpholin-4-ylphenyl)-$N^2$-(3,4,5-trimethoxyphenyl)pyrimidine-2,4-diamine hydrochloride (88 mg, 90%) as a dark grey solid. $^1$H NMR (DMSO-$d_6$/$D_2O$): δ 8.40-8.44 (m, 1H), 8.26 (s, 1H), 7.28-7.72 (m, 1 H), 7.10 (m, 2 H), 6.94 (s, 2 H), 3.80 (m, 4 H), 3.69 (s, 6 H), 3.66 (s, 3 H), 2.85 (m, 4 H). MS m/z 516 (M+1).

EXAMPLE 28

N-[4-(5-Bromo-4-[(3,4,5-trimethoxyphenyl)amino]pyrimidin-2-yl}amino)phenyl]acetamide hydrochloride

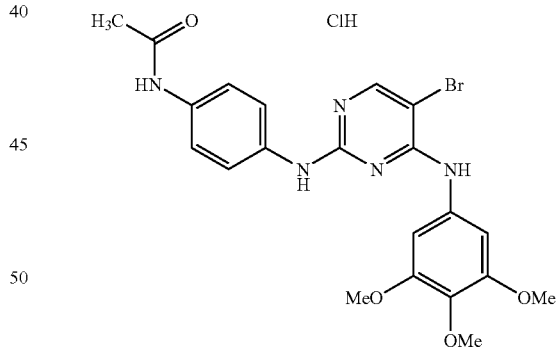

To a mixture of 5-bromo-2-chloro-N-(3,4,5-trimethoxyphenyl)pyrimidin-4-amine (67 mg, 0.178 mmol) and N-(4-aminophenyl)acetamide (28 mg, 0.185 mmol) in 2-propanol (2 mL) was added 1N HCl in diethyl ether (50 uL, 0.05 mmol). The reaction mixture was heated at 90° C. for approx. 36 hours. After the reaction was cooled to room temperature the mixture was taken up in 1:1 acetonitrile/$H_2O$ (60 mL) and lyopholized to give N-[4-({5-bromo-4-[(3,4,5-trimethoxyphenyl)amino]pyrimidin-2-yl}amino)phenyl]acetamide hydrochloride (67 mg, 72%) as a grey solid. $^1$H NMR (DMSO-$d_6$/$D_2O$): δ 8.21 (s, 1H), 7.25-7.67 (m, 4H), 6.87 (s, 2 H), 3.70 (s, 3 H), 3.69 (s, 6 H), 2.00 (s, 3H). MS m/z 488 (M+1).

EXAMPLE 29

Dimethyl 2-[(2-{[4-(acetylamino)phenyl]amino}-5-nitropyrimidin-4-yl)amino]terephthalate hydrochloride

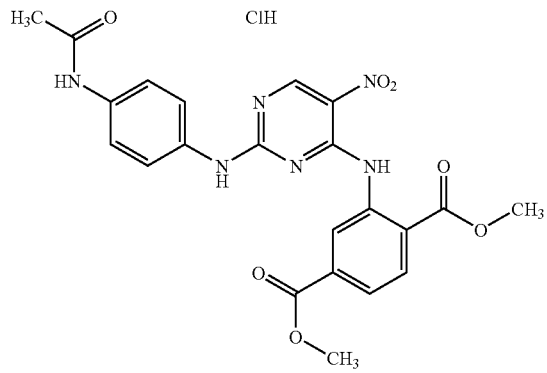

In a similar manner as described in Example 1 from dimethyl 2-[(2-chloro-5-nitropyrimidin-4-yl)amino]terephthalate (65 mg, 0.178 mmol) and N-(4-aminophenyl)acetamide (28 mg, 0.185 mmol) was obtained dimethyl 2-[(2-{[4-(acetylamino)phenyl]amino}-5-nitropyrimidin-4-yl)amino]terephthalate hydrochloride (72 mg, 78%) as an off yellow solid. $^1$H NMR (DMSO-$d_6$/$D_2O$): § 9.12 (s, 1 H), 8.67 (s, 1 H), 8.10 (d, 1 H), 7.88 (dd, 1 H), 7.44 (d, 2 H), 7.33 (d, 2 H), 3.90 (s, 3 H), 3.81 (s, 3 H), 2.03 (s, 3 H). MS m/z 480 (M+1).

EXAMPLE 30

Benzyl 2-[(2-{[4-(acetylamino)phenyl]amino}-5-nitropyrimidin-4-yl)amino]benzoate hydrochloride

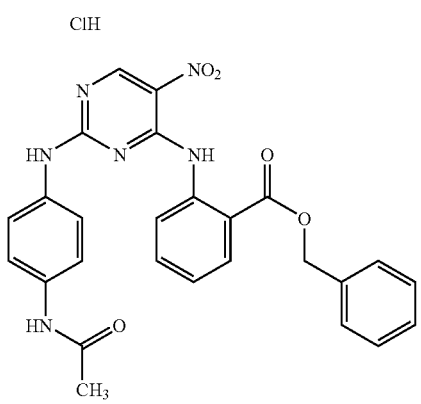

In a similar manner as described in Example 1 from benzyl 2-[(2-chloro-5-nitropyrimidin-4-yl)amino]benzoate (68 mg, 0.178 mmol) and N-(4-aminophenyl)acetamide (28 mg, 0.185 mmol) was obtained benzyl 2-[(2-{[4-(acetylamino)phenyl]amino}-5-nitropyrimidin-4-yl)amino]benzoate hydrochloride (73 mg, 77%) as a yellow solid. $^1$H NMR (DMSO-$d_6$/$D_2O$): § 9.03 (s, 1 H), 8.22 (m, 1 H), 8.01 (d, 1 H), 7.58 (t, 1 H), 7.29-7.45 (m, 10 H), 5.31 (s, 2 H), 2.01 (s, 3 H). MS m/z 498 (M+1).

EXAMPLE 31

Methyl 2-[(2-{[4-(acetylamino)phenyl]amino}-5-nitropyrimidin-4-yl)amino]-6-methylbenzoate hydrochloride

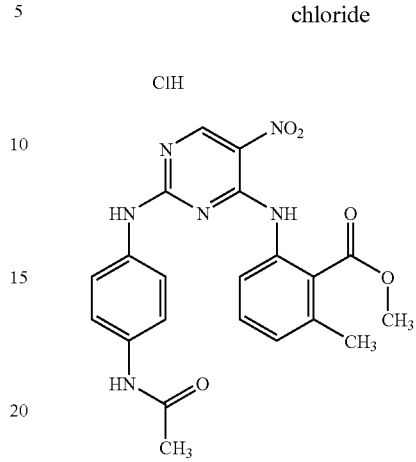

In a similar manner as described in Example 1 from methyl 2-[(2-chloro-5-nitropyrimidin-4-yl)amino]-6-methylbenzoate (57 mg, 0.178 mmol) and N-(4-aminophenyl)acetamide (28 mg, 0.185 mmol) was obtained methyl 2-[(2-{[4-(acetylamino)phenyl]amino}-5-nitropyrimidin-4-yl)amino]-6-methylbenzoate hydrochloride (47 mg, 56%) as a yellow solid. $^1$H NMR (DMSO-$d_6$/$D_2O$): § 9.03 (s, 1 H), 7.73 (m, 1 H), 7.33-7.45 (m, 5 H), 7.22 (d, 1 H), 3.80 (s, 3 H), 2.35 (s, 3 H), 2.00 (s, 3 H). MS m/z 436 (M+1).

EXAMPLE 32

Isobutyl 2-[(2-{[4-(acetylamino)phenyl]amino}-5-nitropyrimidin-4-yl)amino]benzoate hydrochloride

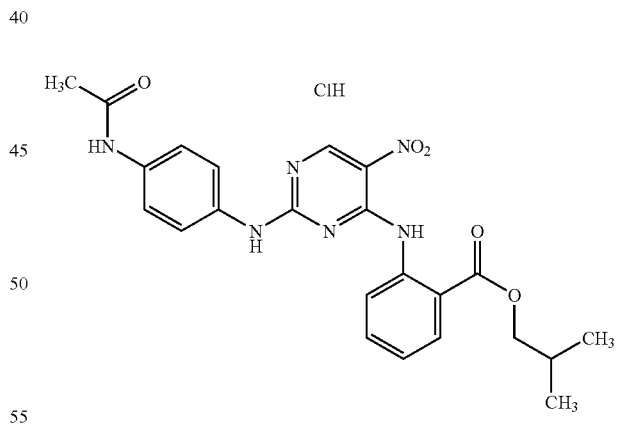

In a similar manner as described in Example 1 from isobutyl 2-[(2-chloro-5-nitropyrimidin-4-yl)amino]benzoate (62 mg, 0.178 mmol) and N-(4-aminophenyl)acetamide (28 mg, 0.185 mmol) was obtained isobutyl 2-[(2-{[4-(acetylamino)phenyl]amino}-5-nitropyrimidin-4-yl)amino]benzoate hydrochloride (17 mg, 19%) as an off yellow solid. $^1$H NMR (DMSO-$d_6$/$D_2O$): § 9.06 (s, 1 H), 8.24 (m, 1 H), 7.99 (dd, 1 H), 7.57 (t, 1 H), 7.28-7.46 (m, 5 H), 4.05 (d, 2 H), 2.01 (s, 3 H), 0.91 (d, 6 H). MS m/z 464 (M+1).

EXAMPLE 33

2-[(2-{[4-(Acetylamino)phenyl]amino}-5-nitropyrimidin-4-yl)amino]-6-methylbenzoic acid hydrochloride

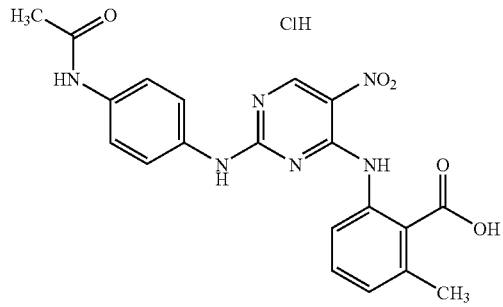

In a similar manner as described in Example 1 from 2-[(2-chloro-5-nitropyrimidin-4-yl)amino]-6-methylbenzoic acid (54 mg, 0.178 mmol) and N-(4-aminophenyl)acetamide (28 mg, 0.185 mmol) was obtained 2-[(2-{[4-(acetylamino)phenyl]amino}-5-nitropyrimidin-4-yl)amino]-6-methylbenzoic acid hydrochloride (25 mg, 30%) as an off yellow solid. $^1$H NMR (DMSO-$d_6$/$D_2O$): § 9.04 (s, 1 H), 7.74 (m, 1 H), 7.34-7.47 (m, 5 H), 7.19 (d, 1 H), 2.39 (s, 3 H), 2.01 (s, 3 H). MS m/z 422 (M+1).

EXAMPLE 34

N-Cyclohexyl-2-({5-nitro-2-[(3,4,5-trimethoxyphenyl)amino]pyrimidin-4-yl}amino)benzamide hydrochloride

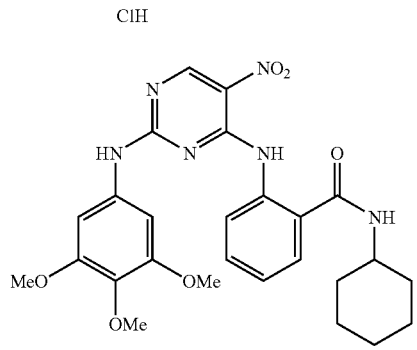

In a similar manner as described in Example 1 from 2-[(2-chloro-5-nitropyrimidin-4-yl)amino]-A-cyclohexylbenzamide (66 mg, 0.178 mmol) was obtained N-cyclohexyl-2-({5-nitro-2-[(3,4,5-trimethoxyphenyl)amino]pyrimidin-4-yl}amino)benzamide hydrochloride (32 mg, 32%) as an off yellow solid. $^1$H NMR (DMSO-$d_6$/$D_2O$): § 9.07 (s, 1 H), 8.15 (m, 2 H), 7.58 (d, 1 H), 7.34 (m, 1 H), 7.21 (t, 1 H), 6.91 (s, 2 H), 3.75 (m, 1 H), 3.64 (s, 3 H), 3.59 (s, 6 H), 1.05-1.84 (m, 10 H). MS m/z 522 (M+1).

EXAMPLE 35

1-[2-({5-Nitro-2-[(3,4,5-trimethoxyphenyl)amino]pyrimidin-4-yl}amino)phenyl]ethanone hydrochloride

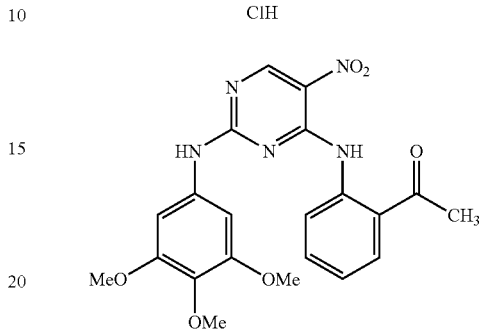

In a similar manner as described in Example 3 from 1-{2-[(2-chloro-5-nitropyrimidin-4-yl)amino]phenyl}ethanone (52 mg, 0.178 mmol) was obtained 1-[2-({5-nitro-2-[(3,4,5-trimethoxyphenyl)amino]pyrimidin-4-yl}amino)phenyl]ethanone hydrochloride (63 mg, 74%) as a tan solid. $^1$H NMR (DMSO-$d_6$/$D_2O$): § 9.09 (s, 1 H), 8.37 (m, 1 H), 8.00 (d, 1 H), 7.44 (t, 1 H), 7.28 (t, 1 H), 6.91 (s, 2 H), 3.65 (s, 3 H), 3.60 (s, 6 H), 2.59 (s, 3 H). MS m/z 439 (M+1).

EXAMPLE 36

[5-Chloro-2-({5-nitro-2-[(3,4,5-trimethoxyphenyl)amino]pyrimidin-4-yl}amino)phenyl](2-fluorophenyl)methanone hydrochloride

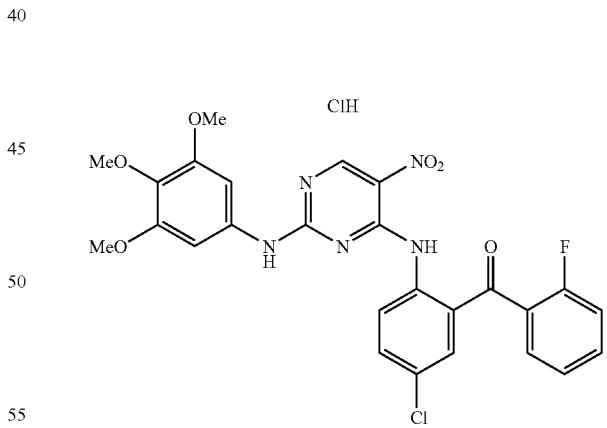

In a similar manner as described in Example 1 from {5-chloro-2-[(2-chloro-5-nitropyrimidin-4-yl)amino]phenyl}(2-fluorophenyl)methanone (72 mg, 0.178 mmol) was obtained [5-chloro-2-({5-nitro-2-[(3,4,5-trimethoxyphenyl)amino]pyrimidin-4-yl}amino)phenyl](2-fluorophenyl)methanone hydrochloride (25 mg, 23%) as brown solid. $^1$H NMR (DMSO-$d_6$/$D_2O$): § 9.00 (s, 1 H), 8.10 (m, 1 H), 7.20-7.65 (m, 6 H), 6.91 (s, 2 H), 3.69 (s, 3 H), 3.62 (s, 6 H). MS m/z 553 (M+1).

EXAMPLE 37

8-({5-Nitro-2-[(3,4,5-trimethoxyphenyl)amino]pyrimidin-4-yl}amino)-2-naphthol hydrochloride

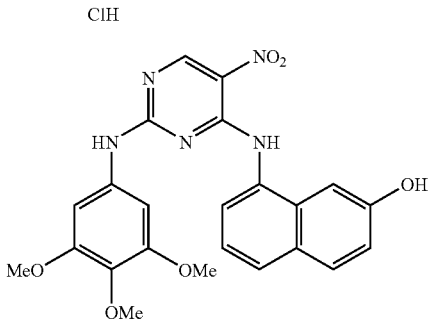

In a similar manner as described in Example 3 from 8-[(2-chloro-5-nitropyrimidin-4-yl)amino]-2-naphthol (56 mg, 0.178 mmol) was obtained 8-({5-nitro-2-[(3,4,5-trimethoxyphenyl)amino]pyrimidin-4-yl}amino)-2-naphthol hydrochloride (32 mg, 36%) as a brown solid. $^1$H NMR (DMSO-$d_6$/$D_2$O): § 9.11 (s, 1 H), 7.66-7.86 (m, 3 H), 7.26 (t, 1 H), 7.09-7.18 (m, 2 H), 6.77 (s, 2 H), 3.55 (s, 3 H), 3.32 (s, 6 H). MS m/z 463 (M+1).

EXAMPLE 38

N-(tert-butyl)-2-({5-methyl ketone-2-[(3,4,5-trimethoxyphenyl)amino]pyrimidin-4-yl}amino) benzamide

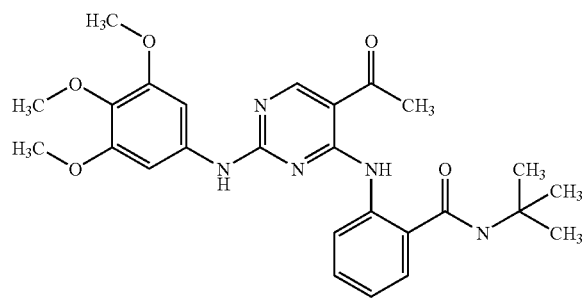

To a heated (100° C.) mixture of N-(tert-butyl)-2-({5-Bromo-2-[(3,4,5-trimethoxyphenyl)amino]pyrimidin-4-yl}amino) benzamide (102 mg, 0.192 mmol), tributyl (1-ethoxyvinyl)tin (85 mg, 0.235 mmol) in dimethylformamide (3 ml) was added tetrakis(triphenylphosphine) palladium (0) (15 mg, 0.013 mmol). The reaction was heated for 18 h. The reaction was poured into a vigorously stirring mixture of 5M potassium fluoride solution:ethyl acetate/1:1 and stirred for 0.5 h. The biphase mixture was flushed through a Celite pad and the pad washed with hot ethyl acetate. The combined organic phase was washed with water, saturated sodium chloride and filtered through Whatman PS 1 paper. The organic phase was concentrated in vacuo to a crude solid. The solid was triturated the diethyl ether and further purified by chromatography to yield N-(tert-butyl)-2-({5-methyl ketone-2-[(3,4,5-trimethoxyphenyl)amino]pyrimidin-4-yl}amino) benzamide (10 mg, 11%) as a cream solid. $^1$H NMR (DMSO-$d_6$): δ 11.52 (br s, 1H), 9.69 (br s, 1H), 8.84 (s, 1H), 7.99 (br s, 1H), 7.86 (s, 1H), 7.62-7.52 (m, 2H), 7.38 (d, 1H, J=7.5 Hz), 7.13 (t, 1H, J=7.4 Hz), 6.95 (br s, 1H), 3.58 (s, 3H), 3.53 (br s, 6H), 2.49 (s, 3H), 1.28 (s, 9H); ES-MS m/z 494 (M+H).

EXAMPLE 39

4-{[2-(4-Methylbenzoyl)phenyl]amino}-2-[(3,4,5-trimethoxyphenyl)amino]pyrimidine-5-carbonitrile

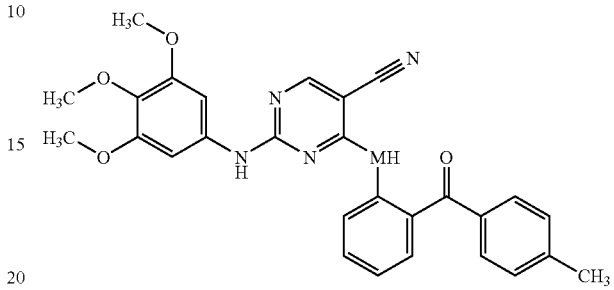

To a mixture of 4-{[2-(4-methylbenzoyl)phenyl]amino}-2-(methylsulfonyl) pyrimidine-5-carbonitrile (54 mg, 0.138 mmol) and 3,4,5-trimethoxyaniline (26 mg, 0.142 mmol) in absolute ethanol (3 ml) was added 1N HCl in diethyl ether (3 drops). The reaction was facilitated using microwave irradiation. The reaction was heated at 180° C. for 600 sec. using Personal Chemistry SmithSynthesizer. On cooling a crude yellow solid was collected by filtration. Pure sample was obtained after chromatography to give 4-{[2-(4-methylbenzoyl)phenyl]amino}-2-[(3,4,5-trimethoxyphenyl)amino]pyrimidine-5-carbonitrile (25 mg, %) as a canary yellow solid. $^1$H NMR (DMSO-$d_6$): δ 10.0 (s, 1H), 9.39 (br s, 1H), 8.39 (s, 1H), 8.04 (d, 1H, J=8.4 Hz), 7.58-7.48 (m, 4H), 7.28 (t, 1H, J=7.6 Hz), 7.22 (d, 2H, J=7.9 Hz), 6.91 (s, 1H), 3.65 (s, 3H), 3.61 (s, 6H), 2.35 (s, 3H); ES-MS m/z 496 (M+H).

EXAMPLE 40

Biological Examples

I. Assay for Inhibition of PLK1

A. Preparation of 6× N-terminal His-tagged PLK Kinase Domain

6× N-terminal His-tagged PLK kinase domain (amino acids 21-346 preceded by MKKGHHHHHHD) was prepared from baculovirus infected T. ni cells under polyhedrin promoter control. All procedures were performed at 4° C. Cells were lysed in 25 mM HEPES, 200 mM NaCl, 25 mM imidazole; pH 8.0. The homogenate was centrifuged at 14K rpm in a SLA-1500 rotor for 40 min and the supernatant filtered through a 1.2 micron filter. The supernatant was loaded onto a Nickel chelating Sepharose (Amersham Pharmacia) column and washed with 25 mM HEPES, 500 mM NaCl, 25 mM imidazole; pH 8.0. The column was then washed with a 16.6% B step where buffer B is 25 mM HEPES, 500 mM NaCl, 300 mM imidazole; pH 8.0. Protein was eluted using a 10-column volume linear gradient from 16.6% B to 100% B. Fractions containing PLK were determined by SDS-PAGE. PLK was concentrated using a 10 kDa molecular weight cutoff membrane and then loaded onto a Superdex 75 gel filtration (Amersham Pharmacia) column equilibrated in 25 mM HEPES, 1 mM DTT, 500 mM NaCl; pH 8.0. Fractions containing PLK were determined by SDS-PAGE. PLK was pooled, aliquoted and stored at −80° C. Samples were quality controlled using mass spectrometry.

B. Enzyme Activity+/−Inhibitors was Determined as Follows:

Compounds were added to the plate (1 μl in 100% DMSO). DMSO (2% final) and EDTA (55.5 mM final) were used as controls. Reaction Mix A is prepared as follows at 4° C.:

Reaction Mix A (substrate Mix):
25 mM HEPES, pH 7.2
15 mM MgCl2
2 μM ATP
0.1 μCi/well $^{33}$P-γ ATP (10 Ci/mMol)
2 μM substrate peptide (Biotin-Ahx-SFNDTLDFD)

Reaction Mix B is prepared as follows at 4° C.:
Reaction Mix B (Enzyme Mix)
25 mM HEPES, pH 7.2
15 mM $MgCl_2$
0.15 mg/ml BSA
2 mM DTT
2-10 nM PLK1 kinase domain Reaction Mix A (20 μl) is added per well. Reaction Mix B (20 μl) is added per well. Incubate 1.5 hrs. at RT. The enzymatic reaction is stopped with 175 μl of SPA/EDTA bead mix (29 mM EDTA, 2.5 mg/ml Streptavidin-coated SPA in Standard Dulbecco's PBS (without $Mg^{2+}$ and $Ca^{2+}$), 60 μM ATP). Plates are sealed spun (after a 1 hr incubation at RT) at 1,000×g for 7 min or settled overnight, then plates counted in Packard TopCount for 30 seconds/well.

C. Results

The data obtained is reported in Table 1 below. In Table 1, +=pIC50 <5; ++=pIC50 5-7; +++=pIC50 >7.

II. Methylene Blue Growth Inhibition Assay

Normal Human foreskin fibroblasts (HFF) and human colon (HCT116, RKO), lung (H460), prostate (PC3), and breast tumor (MCF7) cell lines were cultured in high glucose DMEM (Life Technologies) containing 10% fetal bovine serum (FBS) at 37° C. in a humidified 10% $CO_2$, 90% air incubator. Cells were harvested using trypsin/EDTA, counted using a haemocytometer, and plated in 100 μl of the appropriate media, at the following densities, in a 96-well tissue culture plate (Falcon 3075): HFF 5,000 cells/well, HCT116 3,000 cells/well, RKO 2,500 cells/well, H460 2,000 cells/well, PC3 8,000 cells/well, MCF7 4,000 cells/well. The next day, compounds were diluted in DMEM containing 100 μg/ml gentamicin, at twice the final required concentration, from 10 mM stock solutions in DMSO. 100 μl/well of these dilutions were added to the 100 μl of media currently on the cell plates. Medium containing 0.6% DMSO was added to control wells. Compounds diluted in DMEM were added to all cell lines. The final concentration of DMSO in all wells was 0.3%. Cells were incubated at 37° C., 10% $CO_2$ for 3 days. Medium was removed by aspiration. Cell biomass was estimated by staining cells with 90 μl per well methylene blue (Sigma M9140, 0.5% In 50:50 ethanol:water), and incubation at room temperature for at least 30 minutes. Stain was removed, and the plates rinsed under a gentle stream of water, and air-dried. To release stain from the cells 100 μl of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$. The data obtained reported in Table 1 below. In Table 1, +=10->30 uM; ++=1-10 uM; +++=<1 uM.

TABLE 1

| Example | Ave pIC50 PLK Enzyme Inhibition | MeB Cell Line | IC50 (μM) |
|---|---|---|---|
| 1 | +++ | -- | -- |
| 3 | +++ | H460 | +++ |
|  |  | HCT116 | +++ |
|  |  | HFF | ++ |
|  |  | MCF7 | +++ |
|  |  | PC3 | ++ |
|  |  | RKO | +++ |
| 5 | +++ | H460 | ++ |
|  |  | HCT116 | ++ |
|  |  | HFF | ++ |
|  |  | MCF7 | ++ |
|  |  | PC3 | ++ |
|  |  | RKO | ++ |
| 7 | +++ | H460 | ++ |
|  |  | HCT116 | ++ |
|  |  | HFF | + |
|  |  | MCF7 | ++ |
|  |  | PC3 | ++ |
|  |  | RKO | ++ |
| 9 | +++ | H460 | ++ |
|  |  | HCT116 | ++ |
|  |  | HFF | + |
|  |  | MCF7 | ++ |
|  |  | PC3 | ++ |
|  |  | RKO | ++ |
| 11 | +++ | -- | -- |
| 13 | +++ | -- | -- |
| 15 | +++ | H460 | ++ |
|  |  | HCT116 | ++ |
|  |  | HFF | ++ |
|  |  | MCF7 | ++ |
|  |  | PC3 | ++ |
|  |  | RKO | +++ |
| 17 | +++ | -- | -- |
| 19 | +++ | H460 | ++ |
|  |  | HCT116 | + |
|  |  | HFF | + |
|  |  | MCF7 | ++ |
|  |  | PC3 | + |
|  |  | RKO | ++ |
| 21 | +++ | -- | -- |
| 22 | +++ | H460 | + |
|  |  | HCT116 | + |
|  |  | HFF | + |
|  |  | MCF7 | + |
|  |  | PC3 | + |
|  |  | RKO | + |
| 23 | +++ | -- | -- |
| 24 | +++ | -- | -- |
| 25 | +++ | -- | -- |
| 27 | ++ | -- | -- |
| 28 | + | -- | -- |
| 29 | ++ | -- | -- |
| 30 | ++ | -- | -- |
| 31 | +++ | -- | -- |
| 32 | +++ | -- | -- |
| 33 | +++ | -- | -- |
| 34 | +++ | H460 | ++ |
|  |  | HCT116 | ++ |
|  |  | HFF | ++ |
|  |  | MCF7 | ++ |
|  |  | PC3 | + |
|  |  | RKO | ++ |
| 35 | +++ | -- | -- |
| 36 | +++ | H460 | ++ |
|  |  | HCT116 | ++ |
|  |  | HFF | + |
|  |  | MCF7 | ++ |
|  |  | PC3 | + |
|  |  | RKO | ++ |
| 37 | +++ | -- | -- |
| 38 | +++ | -- | -- |
| 39 | +++ | H460 | ++ |
|  |  | HCT116 | ++ |
|  |  | HFF | + |
|  |  | MCF7 | ++ |

TABLE 1-continued

| Example | Ave pIC50 PLK Enzyme Inhibition | MeB Cell Line | IC50 (µM) |
|---|---|---|---|
| | | PC3 | ++ |
| | | RKO | ++ |

The invention claimed is:

1. A compound of formula (I):

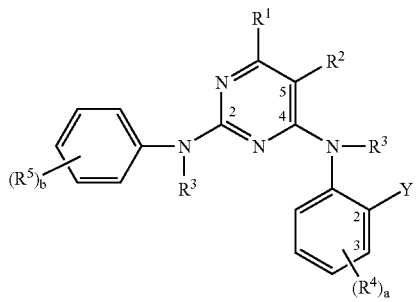

wherein:

$R^1$ is selected from the group consisting of H, halo, alkyl, alkenyl, alkynyl;

$R^2$ is selected from the group consisting of cycloalkyl, cycloalkenyl, $-(R^7)_g-C(O)R^6$, $-(R^7)_g-CO_2R^6$, $-(R^7)_g-C(O)N(R^6)_2$, $-(R^7)_g-OR^6$, $-O-(R^7)_g-Ay$, $-(R^7)_g-S(O)_eR^6$, $-(R^7)_g-N(R^6)_2$, $-(R^7)_g-N(R^6)C(O)R^6$, $-(R^7)_g-CN$, $-(R^7)_g-SCN$, $-NO_2$, $-N_3$, and 5- to 9-membered heteroaryl containing 1 or 2 heteroatoms selected from N, O and S;

each $R^3$ is the same or different and is independently H or alkyl;

Y is selected from the group consisting of $-C(O)R^8$, and $-C(S)R^8$, wherein $R^8$ is selected from the group consisting of alkyl, alkenyl, alkynyl, cycloalkyl, cycloalkenyl, Ay, Het, $-OR^6$, $-O-(R^7)_g-Ay$, $-O-(R^7)_g-Het$, $-N(R^6)_2$, $-N(R^6)-(R^7)_g-Ay$, $-N(R^6)-(R^7)_g-Het$, $-N(R^6)-(R^7)_g-OR^6$, $-N(R^6)-(R^7)_g-C(O)R^6$, $-N(R^6)-(R^7)_g-CO_2R^6$, $-N(R^6)-(R^7)_g-SO_2R^6$, and $-N(R^6)-(R^7)_g-N(R^6)_2$;

a is 0, 1, 2 or 3;

each $R^4$ is the same or different and is independently selected from the group consisting of halo, alkyl, $-(R^7)_g$-cycloalkyl, $-(R^7)_g-C(O)R^6$, $-(R^7)_g-CO_2R^6$, $-(R^7)_g-C(O)N(R^6)_2$, $-(R^7)_g-OR^6$, $-(R^7)_g-S(O)_eR^6$, $-(R^7)_g-N(R^6)_2$ and $-(R^7)_g-N(R^6)C(O)R$;

each e is the same or different and is independently 0, 1 or 2;

b is 0, 1, 2, 3, 4 or 5;

each $R^5$ is the same or different and is a group of formula $(R^7)_g-R^{11}$, each $R^6$ is the same or different and is independently selected from the group consisting of H, alkyl, alkenyl, alkynyl, cycloalkyl and cycloalkenyl;

g is 0 or 1;

$R^7$ is alkylene or alkenylene;

Ay is aryl;

Het is a 5- or 6-membered heterocycle or heteroaryl containing 1, 2 or 3 heteroatoms selected from the group consisting of N, O and S;

$R^{11}$ is selected from the group consisting of halo, alkyl, alkenyl, alkynyl, Ay, Het, $-C(O)$Het, $-CO_2R^6$, $-CO_2Ay$, $-CO_2$Het, $-C(O)N(R^6)_2$, $-C(O)N(R^6)$Ay, $-C(O)N(R^6)$Het, $-C(O)N(R^6)-(R^7)_g-N(R^6)_2$, $-C(O)N(R^6)-(R^7)_g-CO_2R^6$, $-C(O)N(R^6)-(R^7)_g-S(O)_eR^6$, $-OR^6$, $-O-(R^7)_g-Ay$, $-O-(R^7)_g-Het$, $-O-R^7-OR^6$, $-O-R^7-N(R^6)_2$, $-S(O)_eR^6$, $-S(O)_e-(R^7)_g-Het$, $-S(O)_e-(R^7)_g-N(R^6)_2$, —S(O)$_e$—(R$^7$)$_g$—N(R$^6$)Het, —S(O)$_e$N(R$^6$)—(R$^7$)$_g$—C(O)Het, —N(R$^6$)$_2$, —N(R$^6$)—(R$^7$)$_g$-Ay, —N(R$^6$)—(R$^7$)$_g$-Het, —N(R$^6$)—(R$^7$)$_g$—C(O)R$^6$, —N(R$^6$)—C(O)—(R$^7$)$_g$-Het, —N(R$^6$)—C(O)—(R$^7$)$_g$—N(R$^6$)$_2$, —N(R$^6$)—C(O)—(R$^7$)$_g$—N(R$^6$)Het, —N(R$^6$)—C(O)—(R$^7$)$_g$—N(R$^6$)—(R$^7$—O)$_h$—N(R$^6$)—CO$_2$R$^6$, —N(R$^6$)—(R$^7$)$_g$—S(O)$_e$R$^6$, —N(R$^6$)—(R$^7$)$_g$—S(O)$_e$Het, —N(R$^6$)—R$^7$—N(R$^6$)$_2$, —N(R$^6$)—R$^7$—OR$^6$, —CN, and —N$_3$; and h is 1-20;

wherein when R$^1$ is —CH$_3$, R$^2$ is Br or NO$_2$, both R$^3$ are H, a is 0 and b is 0 or 1 wherein R$^5$ is —CO$_2$H, then Y is not —CO$_2$H or a pharmaceutically acceptable salt thereof.

2. The compound according to claim 1, wherein R$^1$ is selected from the group consisting of H, halo and alkyl.

3. The compound according to claim 1, wherein R$^1$ is H.

4. The compound according to claim 1, wherein R$^2$ is selected from the group consisting of —(R$^7$)$_g$—C(O)R$^6$, —(R$^7$)$_g$—C(O)N(R$^6$)$_2$, —(R$^7$)$_g$—CN and —NO$_2$.

5. The compound according to claim 1, wherein R$^2$ is —NO$_2$.

6. The compound according to claim 1, wherein each R$^3$ is the same or different and is independently H or methyl.

7. The compound according to claim 1, wherein each R$^3$ is H.

8. The compound according to claim 1, wherein Y is —C(O)R$^8$.

9. The compound according to claim 1, wherein a is 0 or 1.

10. The compound according to claim 1, wherein b is 0, 1, 2 or 3.

11. The compound according to claim 1, wherein each R$^{11}$ is the same or different and is independently selected from the group consisting of alkyl, Het, —OR$^6$, —S(O)$_e$R$^6$, —S(O)$_e$—(R$^7$)$_g$—N(R$^6$)$_2$, —N(R$^6$)$_2$, —N(R$^6$)—(R$^7$)$_g$—C(O)R$^6$ and —N(R$^6$)—C(O)—(R$^7$)$_g$—N(R$^6$)$_2$.

12. A compound according to claim 1 selected from the group consisting of:

2-({5-nitro-2-[(3,4,5-trimethoxyphenyl)amino]pyrimidin-4-yl}amino)benzoic acid hydrochloride;

2-({5-nitro-2-[(3,4,5-trimethoxyphenyl)amino]pyrimidin-4-yl}amino)benzamide hydrochloride;

N-(tert-butyl)-2-({5-nitro-2-[(3,4,5-trimethoxyphenyl)amino]pyrimidin-4-yl}amino)benzamide hydrochloride;

N-[4-({4-[(2-benzoylphenyl)amino]-5-nitropyrimidin-2-yl}amino)phenyl]acetamide hydrochloride;

8-({5-nitro-2-[(3,4,5-trimethoxyphenyl)amino]pyrimidin-4-yl}amino)-3,4-dihydronaphthalen-1(2H)-one hydrochloride;

1-[2-({5-bromo-2-[(3,4,5-trimethoxyphenyl)amino]pyrimidin-4-yl}amino)phenyl]ethanone hydrochloride;

2-[(2-{[4-(acetylamino)phenyl]amino}-5-nitropyrimidin-4-yl)amino]-N-methylbenzamide hydrochloride;

N$^4$-(1H-indol-4-yl)-5-nitro-N$^2$-(3,4,5-trimethoxyphenyl)pyrimidine-2,4-diamine hydrochloride;

Methyl 2-({5-nitro-2-[(3,4,5-trimethoxyphenyl)amino]pyrimidin-4-yl}amino)benzoate hydrochloride;

N$^4$-(2,3-dihydro-1,4-benzodioxin-5-yl)-5-nitro-N$^2$-(3,4,5-trimethoxyphenyl)pyrimidine-2,4-diamine hydrochloride;

Cyclohexyl 2-[(2-{[4-(acetylamino)phenyl]amino}-5-nitropyrimidin-4-yl)amino]benzoate hydrochloride;

5-Hydroxy-2-({5-nitro-2-[(3,4,5-trimethoxyphenyl)amino]pyrimidin-4-yl}amino)benzoic acid hydrochloride;

2-[(2-{[4-(Acetylamino)phenyl]amino}-5-nitropyrimidin-4-yl)amino]benzoic acid hydrochloride;

N-[4-({4-[(2-Acetylphenyl)amino]-5-bromopyrimidin-2-yl}amino)phenyl]acetamide hydrochloride;

N-[4-({5-Bromo-4-[(2-morpholin-4-ylphenyl)amino]pyrimidin-2-yl}amino)phenyl]acetamide hydrochloride;

5-[(5-Bromo-4-{[2-(methylthio)phenyl]amino}pyrimidin-2-yl)amino]-1,3-dihydro-2H-benzimidazol-2-one hydrochloride;

5-Bromo-N$^4$-(2-morpholin-4-ylphenyl)-N$^2$-(3,4,5-trimethoxyphenyl)pyrimidine-2,4-diamine hydrochloride;

N-[4-({5-Bromo-4-[(3,4,5-trimethoxyphenyl)amino]pyrimidin-2-yl}amino)phenyl]acetamide hydrochloride;

Dimethyl 2-[(2-{[4-(acetylamino)phenyl]amino}-5-nitropyrimidin-4-yl)amino]terephthalate hydrochloride;

Benzyl 2-[(2-{[4-(acetylamino)phenyl]amino}-5-nitropyrimidin-4-yl)amino]benzoate hydrochloride;

Methyl 2-[(2-{[4-(acetylamino)phenyl]amino}-5-nitropyrimidin-4-yl)amino]-6-methylbenzoate hydrochloride;

Isobutyl 2-[(2-{[4-(acetylamino)phenyl]amino}-5-nitropyrimidin-4-yl)amino]benzoate hydrochloride;

2-[(2-{[4-(Acetylamino)phenyl]amino}-5-nitropyrimidin-4-yl)amino]-6-methylbenzoic acid hydrochloride;

N-Cyclohexyl-2-({5-nitro-2-[(3,4,5-trimethoxyphenyl)amino]pyrimidin-4-yl}amino)benzamide hydrochloride;

1-[2-({5-Nitro-2-[(3,4,5-trimethoxyphenyl)amino]pyrimidin-4-yl}amino)phenyl]ethanone hydrochloride;

[5-Chloro-2-({5-nitro-2-[(3,4,5-trimethoxyphenyl)amino]pyrimidin-4-yl}amino)phenyl](2-fluorophenyl)methanone hydrochloride;

8-({5-Nitro-2-[(3,4,5-trimethoxyphenyl)amino]pyrimidin-4-yl}amino)-2-naphthol hydrochloride;

N-(tert-butyl)-2-({5-methyl ketone-2-[(3,4,5-trimethoxyphenyl)amino]pyrimidin-4-yl}amino)benzamide;

4-{[2-(4-Methylbenzoyl)phenyl]amino}-2-[(3,4,5-trimethoxyphenyl)amino]-pyrimidine-5-carbonitrile; and pharmaceutically acceptable salts thereof.

13. A pharmaceutical composition comprising a compound according to claim 1 and a pharmaceutically acceptable carrier, diluent or excipient.

14. The pharmaceutical composition according to claim 13 further comprising a chemotherapeutic agent.

* * * * *

SEQUENCE LISTING

<160> NUMBER OF SEQ ID NOS: 2

<210> SEQ ID NO 1
<211> LENGTH: 11
<212> TYPE: PRT
<213> ORGANISM: baculovirus infected T.ni cells

<400> SEQUENCE: 1

Met Lys Lys Gly His His His His His His Asp
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: optimized PLK peptide substrate

<400> SEQUENCE: 2

Ser Phe Asn Asp Thr Leu Asp Phe Asp
 1               5